United States Patent
Fan et al.

(10) Patent No.: US 11,716,992 B2
(45) Date of Patent: Aug. 8, 2023

(54) 5A5B6C TRICYCLIC SPIROLACTONE DERIVATIVE, PREPARATION METHOD THEREFOR AND USE THEREOF

(71) Applicant: NANKAI UNIVERSITY, Tianjin (CN)

(72) Inventors: Zhijin Fan, Tianjin (CN); Yujie Zhu, Tianjin (CN); Lai Chen, Tianjin (CN); Shuang Zhou, Tianjin (CN); Xiaofeng Guo, Tianjin (CN); Haixia Wang, Tianjin (CN); Bin Yu, Tianjin (CN); Nailou Zhang, Tianjin (CN); Qifan Wu, Tianjin (CN); Dongyan Yang, Tianjin (CN); Bin Zhao, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 234 days.

(21) Appl. No.: 16/755,162

(22) PCT Filed: Mar. 14, 2018

(86) PCT No.: PCT/CN2018/079046
§ 371 (c)(1),
(2) Date: Apr. 10, 2020

(87) PCT Pub. No.: WO2019/071911
PCT Pub. Date: Apr. 18, 2019

(65) Prior Publication Data
US 2021/0289783 A1    Sep. 23, 2021

(30) Foreign Application Priority Data
Oct. 13, 2017 (CN) .......................... 201710963432.6

(51) Int. Cl.
| | |
|---|---|
| *A01N 43/12* | (2006.01) |
| *A01N 43/90* | (2006.01) |
| *A01N 55/00* | (2006.01) |
| *C07D 307/93* | (2006.01) |
| *C07D 493/04* | (2006.01) |
| *C07F 7/18* | (2006.01) |

(52) U.S. Cl.
CPC ............. *A01N 43/12* (2013.01); *A01N 43/90* (2013.01); *A01N 55/00* (2013.01); *C07D 307/93* (2013.01); *C07D 493/04* (2013.01); *C07F 7/188* (2013.01)

(58) Field of Classification Search
CPC .............................. C07D 307/93; A01N 43/12
See application file for complete search history.

(56) References Cited

PUBLICATIONS

Zhu. Organic Biomolecular Chemistry, 2018, 16(7), 1163-66, STN record thereof, entered online Jun. 23, 2018 (Year: 2018).*

* cited by examiner

*Primary Examiner* — Noble E Jarrell

(57) ABSTRACT

A $5_A5_B6_C$ tricyclic spironolactone derivative is provided with a formula XI:

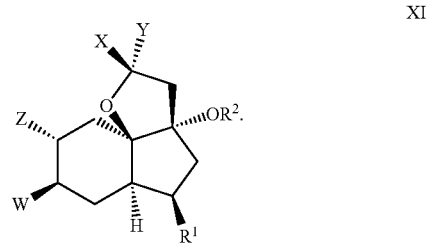

The present invention also relates to its preparation method and its applications in the areas of insecticide, nematicide, fungicide and anti-viral agent. The $5_A5_B6_C$ tricyclic spironolactone derivatives in the present invention are high-performance, broad-spectrum, low-toxicity and low-ecological risk compounds with a wide range of applications in the areas of agriculture, horticulture, forestry and health.

2 Claims, No Drawings

5A5B6C TRICYCLIC SPIROLACTONE DERIVATIVE, PREPARATION METHOD THEREFOR AND USE THEREOF

BACKGROUND OF THE PRESENT INVENTION

Field of Invention

The technical scheme of the present invention relates to a spiral compound, in particular to a $5_A5_B6_C$ tricyclic spironolactone compound.

Description of Related Arts

Spirocyclic compounds are the core active centers of the important chiral catalysts (S-F. Zhu, Q-L. Zhou. Spiro ligands for asymmetric catalysis. *Ligand Design in Metal Chemistry.* 2016, 66-103), which have broad-spectrum of biological activities (S. Kotha, N. R. Panguluri, R. Ali. Design and synthesis of spirocycles. *Eur. J. Org. Chem.* 2017.). Spirodiclofen (Bristow, James Timothy. Novel form of spirodiclofen, a process for its preparation and use the same. PCT Int. Appl. (2017), WO 2017101515A1, 20170622) and spirotetramat (Li, Qianmin; Ji, Qingwei; Liu, Minjie. Insecticide composition containing dinotefuran and spirotetramat for controlling *Bemisia tabaci* in cotton. CN 107125259A, 20170905) are commercialized pesticides. (K)-Histrionicotoxin and Horsfdine are pharmaceutical lead compounds with antibacterial, antifungal and anti-tumor activities (R. Pradhan, M. Patra, A. K. Behera, B. K. Mishra, R. K. Behera. A synthon approach to spiro compounds. *Tetrahedron.* 2006, 62, 779-828; G. T. Zitouni, O. Ozdemir, K. Guven. Synthesis of some 1-[(N,N-di substituted thiocarbamoylthio) acetyl]-3-(2-thienyl)-5-aryl-2-pyrazoline derivatives and investigation of their antibacterial and antifungal activities. *Arch. Pharm.* (Weinheim) 2005, 338, 96-104). Bicyclic spirocyclic derivatives are relatively common, tricyclic spiro structure mainly exists in natural products such as Alliacol A, Alliacolide, Teucrolivine F and Abyssomicin E, et al. Because of its compact chemical structure and distinct biological activity, its synthesis is particularly challenging, and thus attracts the interests of many chemists (Y. W. Liu, Y-B. Cheng, C.-C. Liaw, C.-H. Chen, J.-H. Guh, W.-S. Hwang, J.-S. Tsai, W.-B. Wang, Y. C. Shen. Bioactive diterpenes from *Callicarpa longissima*. *J. Nat. Prod.* 2012, 75, 689-693). $5_A5_B6_C$ is the most compact structure among all the tricyclic spiro compounds (T. Efferth, F. Herrmann, A. Tahrani, M. Wink. Cytotoxic activity of secondary metabolites derived from *Artemisia annua* L. towards cancer cells in comparison to its designated active constituent artemisinin. *Phytomedicine,* 2011, 18, 959-969). The core skeleton of $5_A5_B6_C$ tricyclic spironolactone is mainly obtained by $I_2$/Sm(II)- and $I_2$/Pd(0) mediated cyclization reaction (V. Valerio, Y. Mostinski, R. Kotikalapudi, D. Tsvelikhovsky. Stereo- and regioselective synthesis of tricyclic spirolactones by diastereoisomeric differentiation of a collective key precursor. *Chem. Eur. J.* 2016, 22, 2640), the synthetic reaction conditions are relatively harsh.

In order to seek and find more highly active pesticidal and pharmaceutical lead compounds with broad-spectrum, low-toxicity and low-ecological risks, a $5_A5_B6_C$ tricyclic spironolactone skeleton was constructed under mild conditions for lead derivation in this invention. A series of structural derivatives were synthsized for biological activity screening and evaluation, especially the safety evaluation against environmental biology such as honeybee. The present invention is expected to provide more highly active pesticide candidate with environment compatibility and low resistance risk for novel agrochemical development.

SUMMARY OF THE PRESENT INVENTION

The technical problem needs to be solved by the present invention is to provide a novel $5_A5_B6_C$ tricyclic spironolactone derivative and its preparation methods, its bioactivity in regulating and controlling of pests and pathogens damaging plants and its determination methods in the areas of agriculture, horticulture, forestry and hygiene. The technical solution schems of the present invention is that the $5_A5_B6_C$ tricyclic spironolactones with insecticidal, nematicidal, acaricidal, fungicidal, anti-viral activity and plant induced disease resistance in the areas of agriculture, horticulture, forestry and hygiene have a general formula of XI described below:

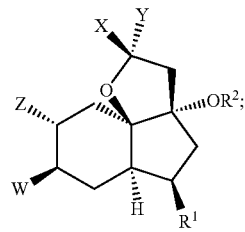

XI wherein:
$R^1$ is hydrogen, $C_1$-$C_6$ alkyl, $C_1$-$C_6$ haloalkyl, $C_1$-$C_6$ alkoxyl, $C_1$-$C_6$ haloalkoxyl, $C_2$-$C_6$ alkenyl, $C_2$-$C_6$ haloalkenyl, $C_2$-$C_6$ alkynyl, $C_2$-$C_6$ haloalkynyl, hydroxyl, $C_3$-$C_6$ cycloalkyl, substituted piperidin-1-yl, substituted morpholin-1-yl, substituted tetrahydropyrrole-1-yl, phenyl or halogen substituted phenyl or $C_1$-$C_6$ alkyl substituted phenyl or $C_1$-$C_6$ haloalkyl substituted phenyl or $C_3$-$C_6$ cycloalkyl substituted phenyl or nitro substituted phenyl or $C_2$-$C_6$ enyl substituted phenyl or $C_2$-$C_6$ haloalkenyl substituted phenyl or $C_3$-$C_6$ cycloalkenyl substituted phenyl or $C_2$-$C_6$ alkynyl substituted phenyl or $C_2$-$C_6$ haloalkynyl substituted phenyl or $C_3$-$C_6$ cycloalkynyl substituted phenyl, pyridinyl or halogen substituted pyridinyl, or $C_1$-$C_6$ alkyl substituted pyridinyl or $C_1$-$C_6$ haloalkyl substituted pyridinyl or $C_3$-$C_6$ cycloalkyl substituted pyridinyl or nitro substituted pyridinyl, or $C_2$-$C_6$ alkenyl substituted pyridinyl or $C_2$-$C_6$ haloalkenyl substituted pyridinyl or $C_3$-$C_6$ cycloalkenyl substituted pyridinyl or $C_2$-$C_6$ alkynyl substituted pyridinyl or $C_2$-$C_6$ haloalkynyl substituted pyridinyl or $C_3$-$C_6$ cycloalkynyl substituted pyridinyl, pyrimidinyl, or halogen substituted pyrimidinyl or $C_1$-$C_6$ alkyl substituted pyrimidinyl or $C_1$-$C_6$ haloalkyl substituted pyrimidinyl or $C_3$-$C_6$ cycloalkyl substituted pyrimidinyl or nitro substituted pyrimidinyl or $C_2$-$C_6$ alkenyl substituted pyrimidinyl or $C_2$-$C_6$ haloalkenyl substituted pyrimidinyl or $C_3$-$C_6$ cycloalkenyl substituted pyrimidinyl or $C_2$-$C_6$ alkynyl substituted pyrimidinyl or $C_2$-$C_6$ haloalkynyl substituted pyrimidinyl or $C_3$-$C_6$ cycloalkynyl substituted pyrimidinyl, substituted five- or six-membered heteroaryl containing one or two N atoms, substituted five- or six-membered heteroaryl containing one or two S atoms, substituted five- or six-membered heteroaryl containing one or two O atoms, substituted five- or six-membered heteroaryl containing one S atom and one N atom, substituted five- or six-membered heteroaryl containing one N atom and one O atom, substituted five- or six-membered heteroaryl containing two N atom and one S atom, or substituted five- or six-membered heteroaryl containing two N atom and one O atom; the aforementioned five- or six-membered heteroaryl is substituted furanyl, thienyl, pyrrolyl, imidazolyl, pyrazolyl, thiazolyl, isothiazolyl, oxazolyl, isoxazolyl, oxadiazolyl, thiadiazolyl, pyridinyl, pyridazinyl, pyrimidinyl, pyrazinyl, triazinyl, tetrazinyl, indolyl, benzothienyl, benzofuryl, benzimidazolyl, indazolyl, benzotriazolyl, benzothiazolyl, benzothiadiazolyl, benzoxazolyl, isomerized quinolinyl, isomerized isoquinolinyl, phthalazinyl, quinoxalinyl, quinazolinyl, misolinyl or naphthyridinyl, alkyl or alkenyl substituted silica-based substituent group; $R^1$ and W constitute

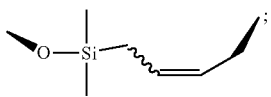

$R^2$ is hydrogen, $C_1$-$C_6$ alkyl, $C_1$-$C_6$ haloalkyl, $C_1$-$C_6$ alkoxyl, $C_1$-$C_6$ haloalkoxyl, $C_2$-$C_6$ alkenyl, $C_2$-$C_6$ haloalkenyl, $C_2$-$C_6$ alkynyl, $C_2$-$C_6$ haloalkynyl, hydroxyl, $C_3$-$C_6$ cycloalkyl, substituted piperidin-1-yl, substituted morpholin-1-yl, substituted tetrahydropyrrole-1-yl, phenyl or halogen substituted phenyl or $C_1$-$C_6$ alkyl substituted phenyl or $C_1$-$C_6$ haloalkyl substituted phenyl or $C_3$-$C_6$ cycloalkyl substituted phenyl or nitro substituted phenyl, or $C_2$-$C_6$ alkenyl substituted phenyl or $C_2$-$C_6$ haloalkenyl substituted phenyl or $C_3$-$C_6$ cycloalkenyl substituted phenyl or $C_2$-$C_6$ alkynyl substituted phenyl or $C_2$-$C_6$ haloalkynyl substituted phenyl or $C_3$-$C_6$ cycloalkynyl substituted phenyl, pyridinyl or halogen substituted pyridinyl, or $C_1$-$C_6$ alkyl substituted pyridinyl or $C_1$-$C_6$ haloalkyl substituted pyridinyl or $C_3$-$C_6$ cycloalkyl substituted pyridinyl or nitro substituted pyridinyl, or $C_2$-$C_6$ alkenyl substituted pyridinyl or $C_2$-$C_6$ haloalkenyl substituted pyridinyl or $C_3$-$C_6$ cycloalkenyl substituted pyridinyl or $C_2$-$C_6$ alkynyl substituted pyridinyl or $C_2$-$C_6$ haloalkynyl substituted pyridinyl or $C_3$-$C_6$ cycloalkynyl substituted pyridinyl, pyrimidinyl, or halogen substituted pyrimidinyl or $C_1$-$C_6$ alkyl substituted pyrimidinyl or $C_1$-$C_6$ haloalkyl substituted pyrimidinyl or $C_3$-$C_6$ cycloalkyl substituted pyrimidinyl or nitro substituted pyrimidinyl or $C_2$-$C_6$ alkenyl substituted pyrimidinyl or $C_2$-$C_6$ haloalkenyl substituted pyrimidinyl or $C_3$-$C_6$ cycloalkenyl substituted pyrimidinyl or $C_2$-$C_6$ alkynyl substituted pyrimidinyl or $C_2$-$C_6$ haloalkynyl substituted pyrimidinyl or $C_3$-$C_6$ cycloalkynyl substituted pyrimidinyl, substituted five- or six-membered heteroaryl containing one or two N atoms, substituted five- or six-membered heteroaryl containing one or two S atoms, substituted five- or six-membered heteroaryl containing one or two O atoms, substituted five- or six-membered heteroaryl containing one S atom and one N atom, substituted five- or six-membered heteroaryl containing one N atom and one O atom, substituted five- or six-membered heteroaryl containing two N atom and one S atom, or substituted five- or six-membered heteroaryl containing two N atom and one O atom; the aforementioned five- or six-membered heteroaryl is substituted furanyl, thienyl, pyrrolyl, imidazolyl, pyrazolyl, thiazolyl, isothiazolyl, oxazolyl, isoxazolyl, oxadiazolyl, thiadiazolyl, pyridinyl, pyridazinyl, pyrimidinyl, pyrazinyl, triazinyl, tetrazinyl, indolyl, benzothienyl, benzofuryl, benzimidazolyl, indazolyl, benzotriazolyl, benzothiazolyl, benzothiadiazolyl, benzoxazolyl, isomerized quinolinyl, isomerized isoquinolinyl, phthalazinyl, quinoxalinyl, quinazolinyl, misolinyl or naphthyridinyl, alkyl or alkenyl substituted silica-based substituent group; $R^2$ and W constitute

wherein: X is hydrogen, $C_1$-$C_6$ alkyl, $C_1$-$C_6$ haloalkyl, $C_1$-$C_6$ alkoxyl, $C_1$-$C_6$ haloalkoxyl, $C_2$-$C_6$ alkenyl, $C_2$-$C_6$ haloalkenyl, $C_2$-$C_6$ alkynyl, or $C_2$-$C_6$ haloalkynyl; Y is hydrogen, $C_1$-$C_6$ alkyl, $C_1$-$C_6$ haloalkyl, $C_1$-$C_6$ alkoxyl, $C_1$-$C_6$ haloalkoxyl, $C_2$-$C_6$ alkenyl, $C_2$-$C_6$ haloalkenyl, $C_2$-$C_6$ alkynyl, or $C_2$-$C_6$ haloalkynyl;

is C=O or C=S; Z is hydrogen, hydroxyl, or halogen; W is hydrogen, hydroxyl, or halogen;

in the above definition of XI, halogen is fluorine, chlorine, bromine or iodine; the above mentioned alkyl, alkenyl or alkynyl are linear or branched;

the alkyl group itself or as part of other substituent is methyl, ethyl, propyl, butyl, pentyl, hexyl or its isomers; its isomer is selected from isopropyl, isobutyl, sec-butyl, tert-butyl, isopentyl or tert-pentyl;

the haloalkyl group choses from the groups contain one or more of the same or different halogen atoms, and the haloalkyl described above is $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$;

the cycloalkyl group itself or as part of other substituent is cyclopropyl, cyclobutyl, cyclopentyl or cyclohexyl;

the alkenyl group itself or as part of the other substituent is vinyl, allyl, 1-propenyl, buten-2-yl, butene-3-yl, pentene-1-yl, penten-3-yl, hexen-1-yl or 4-methyl-3-pentenyl.

The alkyne group itself or as part of the other substituent is ethynyl, propyn-1-yl, propyn-2-yl, butyn-1-yl, butyn-2-yl, 1-methyl-2-butynyl, hexyn-1-yl, or 1-ethyl-2-butynyl;

the formula XI $5_A5_B6_C$ tricyclic spironolactone derivatives in the form of optical isomers and their mixtures including the optical isomers as described as above comprised enantiomers;

the formula XI $5_A5_B6_C$ tricyclic spironolactone derivatives in the form of geometric isomers, that is, (R)-(S) isomers and their mixtures;

the formula XI $5_A5_B6_C$ tricyclic spironolactone derivatives in the form of atropisomers and their mixtures;

although the chemical bonds of three rings in $5_A5_B6_C$ tricyclic spironolactone derivatives of formula XI are described as single bonds, they may also be double bonds; the backbones are described below:

XI

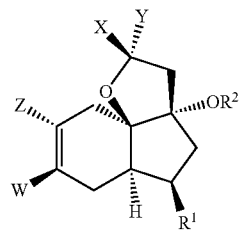

-continued

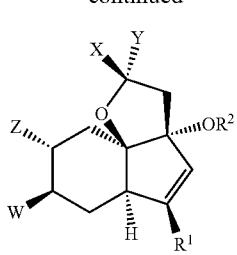

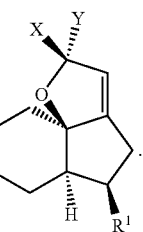

The substituted group described above, the preferred structures are listed bedescribed as follows:

$R^1$ is H, allyl, propargyl, Ac, AcO, t-BuOO—, methoxy, —CH$_2$CO$_2$Et or isopropenyl; $R^2$ is H, allyl, propargyl, Ac, AcO, t-BuOO—, methoxy, —CH$_2$CO$_2$Et or isopropenyl; X is H, OH, OAc, allyl, propargyl; Y is H, OH, OAc, allyl, propargyl;

XI is C=O or C=S; Z is H or OH; W is H or OH; $R^1$ and W constitute

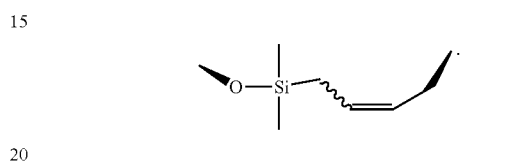

The general synthesis method of the $5_A5_B6_C$ tricyclic spironolactone derivative XI of the present invention is described below:

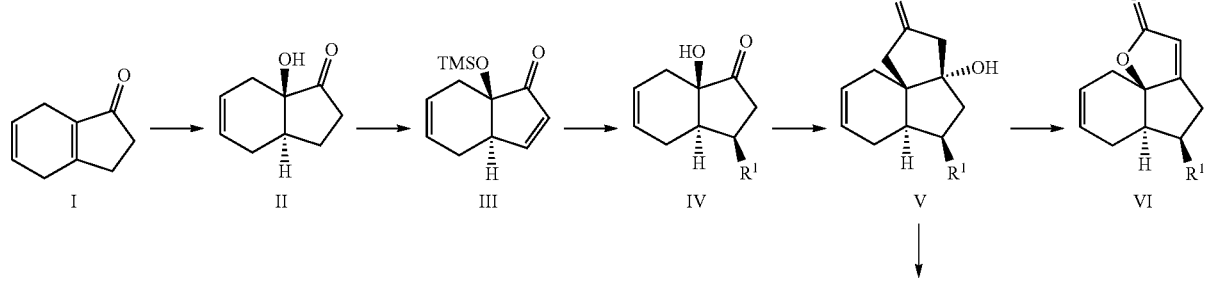

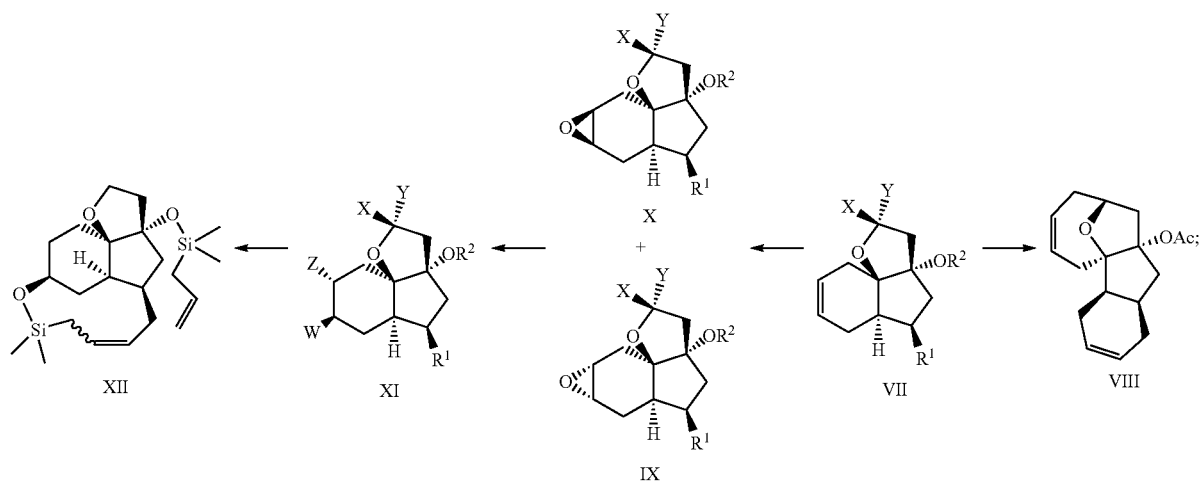

wherein: the definition of the preferred substituted group is as previously described.

$R^1$ is H, allyl, propargyl, Ac, AcO, t-BuOO—, methoxy, —$CH_2CO_2Et$ or isopropenyl; $R^2$ is H, allyl, propargyl, Ac, AcO, t-BuOO—, methoxy, —$CH_2CO_2Et$ or isopropenyl; X is H, OH, OAc, allyl, propargyl; Y is H, OH, OAc, allyl, propargyl;

is C=O or C=S; Z is H or OH; W is H or OH; $R^1$ and W constitute

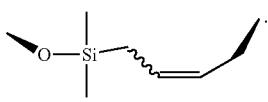

The general synthesis method of $5_A5_B6_C$ tricyclic spironolactone derivative of the present invention and its biological activity determination is described as follows.

(A) General Procedure for the Synthesis of Compound II and II-A

The specific steps of the synthesis of compound II are described below:

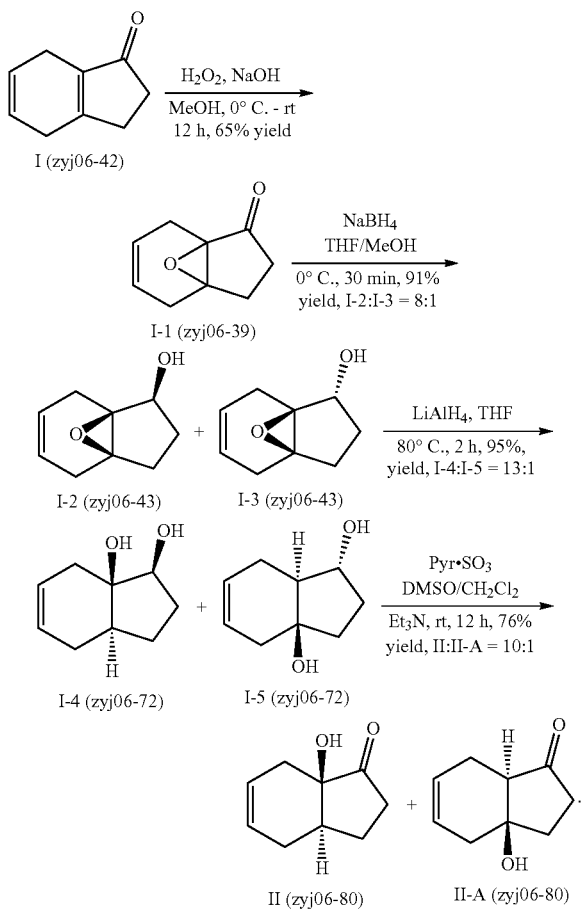

General Procedure for the Synthesis of Compound I-1

The compound I with test code: Zyj06-42) 6 g, 44.72 mmol was dissolved in methanol. Then 30% hydrogen peroxide of 10.14 g, 89.44 mmol was added to the flask drop wisely in an ice bath. The mixture was stirred for 10 minutes. And then 0.5 equivalent sodium hydroxide solution of 1 mol/L, 22.36 mmol was slowly added to the flask drop wisely. The mixture was stirred for another 30 minutes in an ice bath. Then the ice bath was removed at room temperature overnight. Proper amount of saturated sodium bicarbonate solution was added to the mixture. Then the mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate by 15:1 of v/v as eluent to obtain compound I-1 with test code as Zyj06-39 of 3.9 g in the yield of 65%. The amount of compound I-1 and the volume of each reactor are appropriately increased or decreased according to the specific conditions.

General Procedure for the Synthesis of Compound I-2 and Compound I-3

The compound I-1 of 2.5 g, 16.65 mmol with test code: Zyj06-39 was dissolved in the mixed solution of tetrahydrofuran and methanol (v/v=10:1). Then sodium borohydride of 0.63 g, 16.65 mmol was added to the flask in batches in an ice bath. The mixture was stirred for 30 minutes in an ice bath. After the reaction was completed, the mixture was dissolved in saturated sodium bicarbonate solution. Then it was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 6:1 of v/v as eluent to obtain a mixture of inseperable isomers compound I-2 with test code: Zyj06-43 and compound I-3 with test code: Zyj06-43, the I-2:I-3=8:1, 2.3 g, yield: 91%. The amount of the mixture of isomers compound I-2 and compound I-3 and the volume of each reactor are appropriately increased or decreased according to the specific conditions.

General Procedure for the Synthesis of Compound I-4 and Compound I-5

Lithium aluminum hydride of 1 g, 26.28 mmol was added to a 100 mL two-necked flask. The mixture of compound I-2 with test code: Zyj06-43 and compound I-3 with test code: Zyj06-43 of 2 g, 13.14 mmol was dissolved in 30 mL of THF. And then under the nitrogen atmosphere, the solution was dropped to the flask in an ice bath. The mixture was stirred for 15 minutes in an ice bath and then the ice bath was removed. The mixture was heated to reflux for 2 hours at 80° C. After the reaction was completed, water was added to the flask in an ice bath. Then it was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 4:1 of v/v as eluent to obtain a mixture of inseperable isomers compound I-4 with test code: Zyj06-72 and compound I-5 with test code: Zyj06-72, and I-2:I-3=13:1, 2 g, yield: 95%. The amount of the mixture of isomers compound I-4 and compound I-5 and the volume of each reactor are appropriately increased or decreased according to the specific conditions.

General Procedure for the Synthesis of Compound II and Compound II-A

The mixture of isomers compound I-4 with test code: Zyj06-72 and compound I-5 with test code: Zyj06-72 of 2 g, 12.97 mmol was dissolved in the mixture of anhydrous DCM and DMSO with v/v=1:1. Then TEA of 3.94 g, 38.91 mmol and sulfur trioxide pyridine complex of 3.10 g, 19.46 mmol were added to the flask in sequence. The mixture was stirred at room temperature overnight. And excess saturated ammonium chloride solution was added to the flask. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 10:1 of v/v as eluent to obtain a mixture of inseperable isomers compound II and compound II-A, we used the same test code Zyj06-80 to label the mixture of both II and II-A, the ratio of II:II-A=10: 1, 1.5 g, yield: 76%.

The amount of the mixture of isomers compound II and compound II-A and the volume of each reactor are appropriately increased or decreased according to the specific conditions.

(B) General Procedure for the Synthesis of Compound III and III-A

The specific steps of the synthesis of compound III and compound III-A are described below:

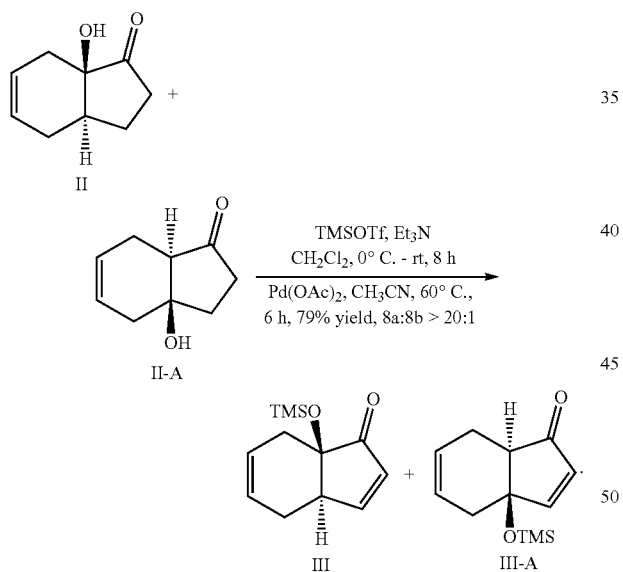

The mixture of isomers compound II with test code: Zyj06-80 and compound II-A with test code: Zyj06-80 of 2 g, 13.14 mmol was dissolved in anhydrous DCM. And then under the nitrogen atmosphere, TEA of 6.65 g, 65.71 mmol and trimethylsilyl trifluoromethanesulfonate of 7.30 g, 32.85 mmol were added in sequence to the flask drop wisely in an ice bath. The mixture was stirred in an ice bath for 30 minutes and then the ice bath was removed. The mixture was stirred at room temperature overnight. And saturated sodium bicarbonate solution was added to the flask. The mixture was extracted with DCM and the combined organic layers were washed with saturated brine, dried over anhydrous sodium sulfate. After filtration and concentration under vacuum, the solvent was removed to obtain the crude product which can be directly used in the next step without purification.

The crude product was dissolved in acetonitrile. Palladium acetate 2.95 g, 13.14 mmol was added to the mixture. The mixture was stirred at 60° C. for 6 hours. After filtration and concentration under vacuum, the solvent was removed. The residue was purified by column chromatography on silica gel with 200~300 mesh and a mixture of petroleum ether with 60-90° C. fraction and ethyl acetate with 100:1 of v/v as eluent to obtain compound III with test code: Zyj06-82 and compound III-A with test code: Zyj06-82, III:III-A>20:1, 2.3 g, yield: 79%. The amount of compound III and the volume of each reactor are appropriately increased or decreased according to the specific conditions.

(C) General Procedure for the Synthesis of Compound IV

The specific steps of the synthesis of compound IV are described below:

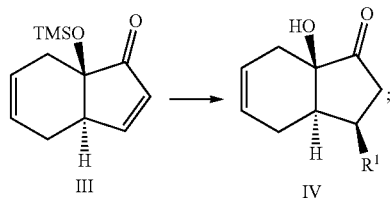

wherein: $R^1$ is allyl, t-BuOO—, methoxy, —CH(CO$_2$Et)$_2$, isopropenyl.

When $R^1$ is allyl, the synthesis method of the compound IV is described as follows:

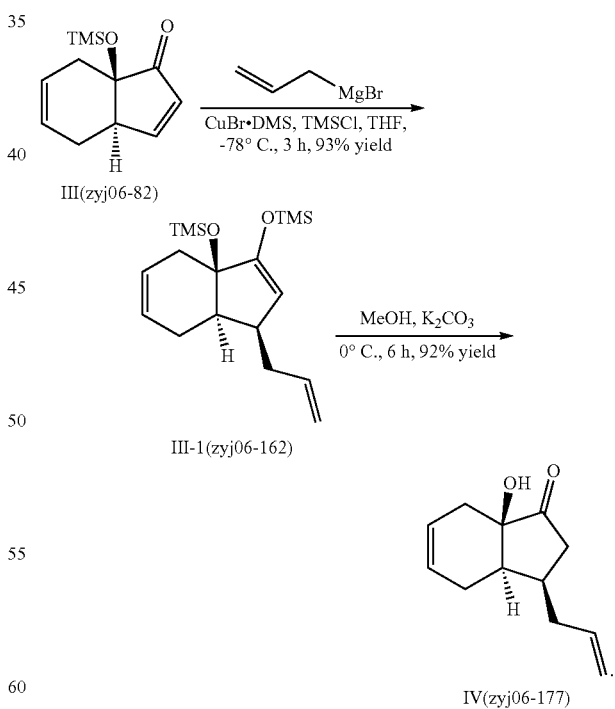

General Procedure for the Synthesis of the Compound III-1 with Test Code: Zyj06-162

To a 100 mL two-necked flask, bromo[thiobis(methane)] copper of 2 g, 9.81 mmol and anhydrous lithium chloride of 0.42 g, 0.81 mmol were added. And then under the nitrogen atmosphere, 20 mL of anhydrous THF was added to the flask. The mixture was stirred for 10 minutes at room temperature. Allylmagnesium bromide of 8.92 mmol was added to the flask droppwisely at −78° C. After stirring for 10 minutes, trimethylsilyl chlorosilane (1.07 g, 9.81 mmol) and compound III with test code: Zyj06-82) (1 g, 4.46 mmol) were dropped step by step to obtain a mixture and the mixture was stirred at −78° C. for 3 hours. After completion the reaction, saturated ammonium chloride solution was added to the mixture and the mixture was extracted with ethyl acetate and the combined ethyl acetate layers were washed with saturated brine, dried with anhydrous sodium sulfate. After filtration and concentration under vacuum, the solvent was removed. The residue was purified by column chromatography on silica gel with 200~300 mesh and petroleum ether with 60-90° C. fraction and ethyl acetate with 15:1 of v/v as eluent to obtain compound III-1 with test code: Zyj06-162 1.4 g, yield: 93%. The amount of compound III-1 and the volume of each reactor are appropriately increased or decreased according to the specific conditions.

General Procedure for the Synthesis of the Compound IV with Test Code: Zyj06-177

The compound III-1 of 2.3 g, 6.84 mmol with test code: Zyj06-162 was dissolved in 20 mL of anhydrous methanol. Then anhydrous potassium carbonate of 1.89 g, 13.67 mmol was added to the flask in an ice bath. The mixture was stirred for 2 hours. Then the ice bath was removed and the mixture was stirred for 4 hours at room temperature until the reaction was completed. And then 10 mL of saturated brine was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 15:1 of v/v as eluent to obtain compound IV with test code: Zyj06-177, 1.2 g, yield: 92%. The amount of compound IV and the volume of each reactor are appropriately increased or decreased according to the specific conditions.

When $R^1$ is t-BuOO—, the synthesis method of the compound IV described as follows is described below:

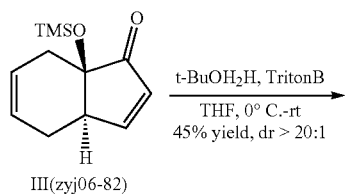

III(zyj06-82)

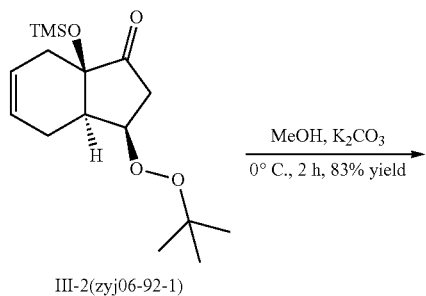

III-2(zyj06-92-1)

-continued

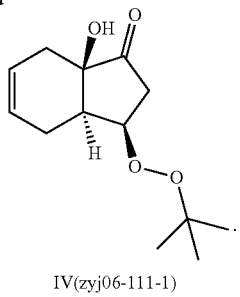

IV(zyj06-111-1)

General Procedure for the Synthesis of the Compound III-2 with Test Code: Zyj06-82

The compound III of 100 mg, 0.45 mmol with test code: Zyj06-82 was dissolved in 15 mL of THF. Then TBHP of 120 mg, 0.9 mmol and tetrabutylammonium hydroxide of 94 mg, 0.22 mmol were added in sequence to the flask in an ice bath. The mixture was stirred for 2 hours in an ice bath until the reaction was completed. And then 15 mL of water was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 100:1 of v/v as eluent to obtain compound III-2 with test code: Zyj06-92-1, 63 mg, yield: 45%. The amount of compound III-2 and the volume of each reactor are appropriately increased or decreased according to the specific conditions.

General Procedure for the Synthesis of the Compound IV with Test Code: Zyj06-11-1)

The compound III-2 (100 mg, 0.32 mmol) with test code: Zyj06-92-1 was dissolved in 20 mL of anhydrous methanol. Then anhydrous potassium carbonate of 8.8 g, 0.64 mmol was added to the flask in an ice bath. The mixture was stirred for 2 hours in an ice bath. Then the ice bath was removed and the mixture was stirred at room temperature for 4 hours until the reaction was completed. And then 10 mL of saturated brine was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 6:1 of v/v as eluent to obtain compound IV with test code: Zyj06-111-1 1.2 g, yield: 83%. The amount of compound IV and the volume of each reactor are appropriately increased or decreased according to the specific conditions.

When $R^1$ is methoxy, the synthesis method of the compound IV described as follows is described below:

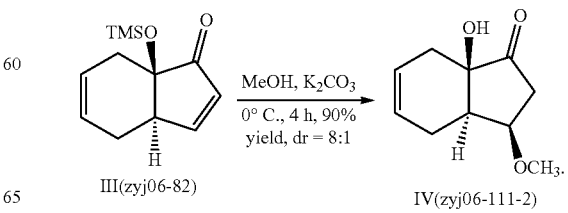

III(zyj06-82)     IV(zyj06-111-2)

The compound III (300 mg, 1.35 mmol) with test code: Zyj06-82 was dissolved in 20 mL of anhydrous methanol. Then anhydrous potassium carbonate (372 mg, 2.70 mmol) was added to the flask in an ice bath. The mixture was stirred for 4 hours in an ice bath until the reaction was completed. And then 15 mL of saturated brine was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 5:1 of v/v as eluent to obtain compound IV with test code: Zyj06-111-2, 221 mg, yield: 90%. The amount of compound IV and the volume of each reactor are appropriately increased or decreased according to the specific conditions.

When $R^1$ is —CH(CO$_2$Et)$_2$, the synthesis method of the compound IV is described as follows:

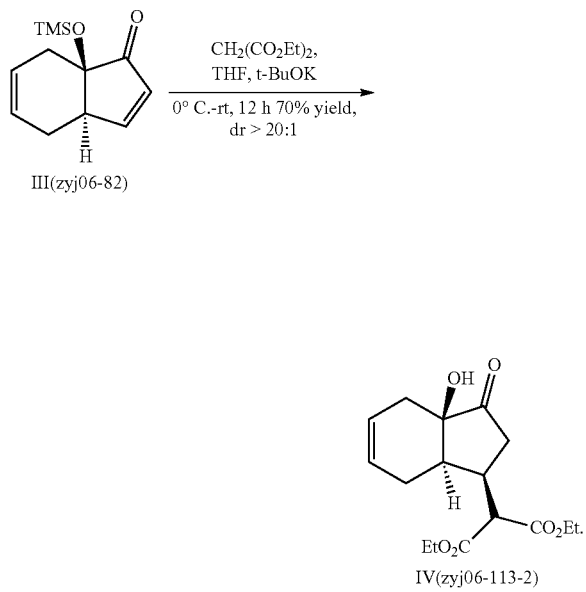

The potassium tert-butoxide of 101 mg, 0.9 mmol was dissolved in 10 mL of anhydrous THF. Then diethyl malonate of 114 mg, 0.9 mmol was dropped to the flask in an ice bath. And then compound III with test code: Zyj06-82, 100 mg, 0.45 mmol was dissolved in anhydrous THF and the solution was dropped to the flask in an ice bath. The mixture was stirred for 30 minutes in an ice bath and then the ice bath was removed at room temperature overnight. And 15 mL of saturated sodium bicarbonate solution was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 6:1 of v/v as eluent to obtain compound IV with test code: Zyj06-113-2, 98 mg, yield: 70%. The amount of compound IV and the volume of each reactor are appropriately increased or decreased according to the specific conditions.

When $R^1$ is isopropenyl, the synthesis method of the compound IV is described as follows:

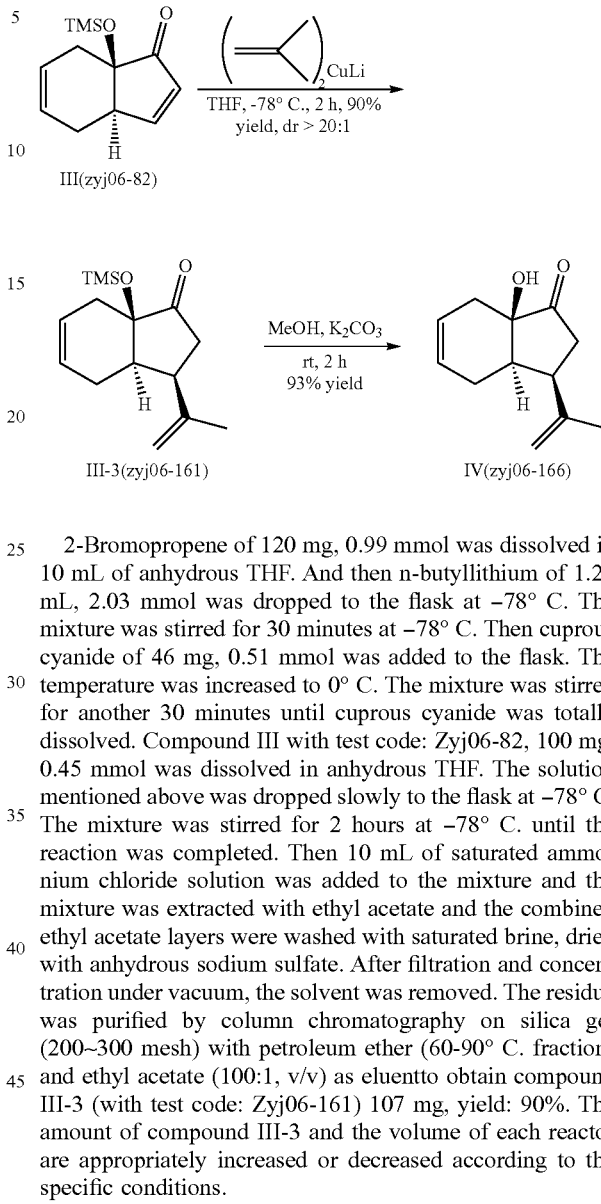

2-Bromopropene of 120 mg, 0.99 mmol was dissolved in 10 mL of anhydrous THF. And then n-butyllithium of 1.26 mL, 2.03 mmol was dropped to the flask at −78° C. The mixture was stirred for 30 minutes at −78° C. Then cuprous cyanide of 46 mg, 0.51 mmol was added to the flask. The temperature was increased to 0° C. The mixture was stirred for another 30 minutes until cuprous cyanide was totally dissolved. Compound III with test code: Zyj06-82, 100 mg, 0.45 mmol was dissolved in anhydrous THF. The solution mentioned above was dropped slowly to the flask at −78° C. The mixture was stirred for 2 hours at −78° C. until the reaction was completed. Then 10 mL of saturated ammonium chloride solution was added to the mixture and the mixture was extracted with ethyl acetate and the combined ethyl acetate layers were washed with saturated brine, dried with anhydrous sodium sulfate. After filtration and concentration under vacuum, the solvent was removed. The residue was purified by column chromatography on silica gel (200~300 mesh) with petroleum ether (60-90° C. fraction) and ethyl acetate (100:1, v/v) as eluentto obtain compound III-3 (with test code: Zyj06-161) 107 mg, yield: 90%. The amount of compound III-3 and the volume of each reactor are appropriately increased or decreased according to the specific conditions.

The compound III-3 of 100 mg, 0.38 mmol with test code: Zyj06-161 was dissolved in 15 mL of anhydrous methanol. Then anhydrous potassium carbonate (105 mg, 0.76 mmol) was added to the flask in an ice bath. The mixture was stirred for 4 hours in an ice bath until the reaction was completed. And then 15 mL of saturated brine was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 5:1 of v/v as eluent to obtain compound IV with test code: Zyj06-166) 68 mg, yield: 93%. The amount of compound IV and the volume of each reactor are appropriately increased or decreased according to the specific conditions.

(D) General Procedure for the Synthesis of Compound V

The specific steps of the synthesis of compound V are described below:

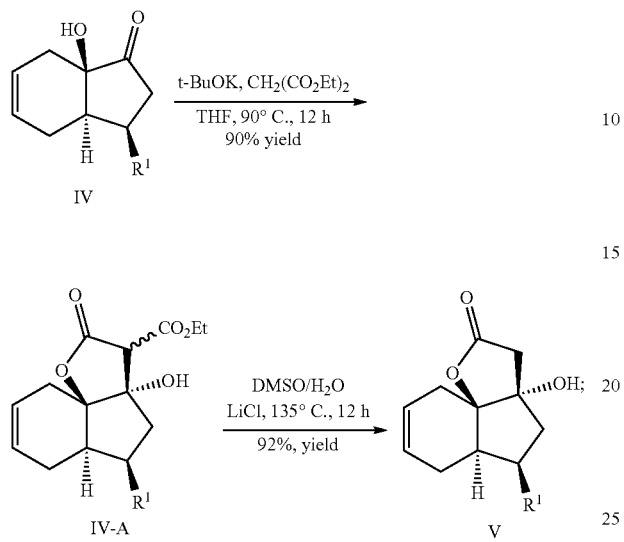

wherein: R$^1$ is allyl, t-BuOO—, methoxy, —CH$_2$CO$_2$Et or isopropenyl.

Potassium tert-butoxide (160 mg, 1.46 mmol) was dissolved in 10 mL of anhydrous THF. Diethyl malonate (230 mg, 1.46 mmol) was dropped to the flask in an ice bath and the mixture was stirred for 5 minutes in an ice bath. Then compound IV (140 mg, 0.73 mmol) was dissolved in THF and the solution was dropped to the flask. The ice bath was removed and the mixture was heated to reflux at 90° C. for 12 hours. When the reaction was completed, 10 mL of saturated sodium bicarbonate solution was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 6:1-3:1 of v/v as eluent to obtain compound IV-A 201 mg, yield: 90%. The amount of compound IV-A and the volume of each reactor are appropriately increased or decreased according to the specific conditions.

Compound IV-A (100 mg, 0.33 mmol) was dissolved in 5.5 mL of DMSO/H$_2$O (v/v=10:1). Then anhydrous lithium chloride (7 mg, 0.17 mmol) was added to the flask. The mixture was heated at 135° C. for 12 hours until the reaction was completed. And then 20 mL of H$_2$O was added to the flask. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 3:1 of v/v as eluent to obtain compound V, 71 mg, yield: 92%. The amount of compound V and the volume of each reactor are appropriately increased or decreased according to the specific conditions.

(E) General Procedure for the Synthesis of Compound VI

The specific steps of the synthesis of compound VI are described below:

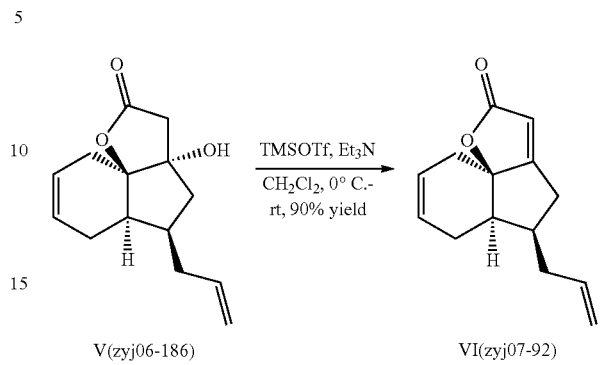

The compound V (100 mg, 0.43 mmol) with test code: Zyj06-186) was dissolved in anhydrous dichloromethane. Then triethylamine (170 mg, 1.71 mmol) and trimethylsilyl trifluoromethanesulfonate (190 mg, 0.85 mmol) were added dropwise in sequence to obtain a mixture in an ice bath. The mixture was stirred in an ice bath for 10 minutes. The ice bath was removed at room temperature overnight. And then 20 mL of saturated sodium bicarbonate solution was added to the flask. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 40:1 of v/v as eluent to obtain compound VI with test code: Zyj07-92 84 mg, yield: 90%.

The amount of compound VI and the volume of each reactor are appropriately increased or decreased according to the specific conditions.

(F) General Procedure for the Synthesis of Compound VII

The specific steps of the synthesis of compound VII are described below:

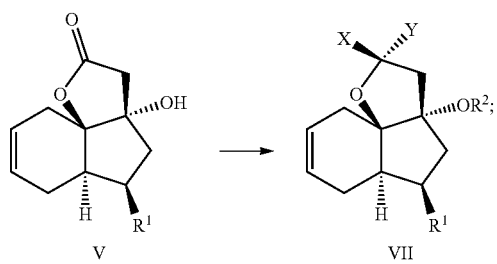

wherein: X is hydrogen, hydroxyl, acetyl or allyl; Y is hydrogen, hydroxyl, acetyl or allyl; R$^1$ is allyl; R$^2$ is hydrogen or hydroxyl.

When X is hydrogen, Y is hydrogen, and $R^2$ is hydrogen, the specific steps of the synthesis of compound VII are described below:

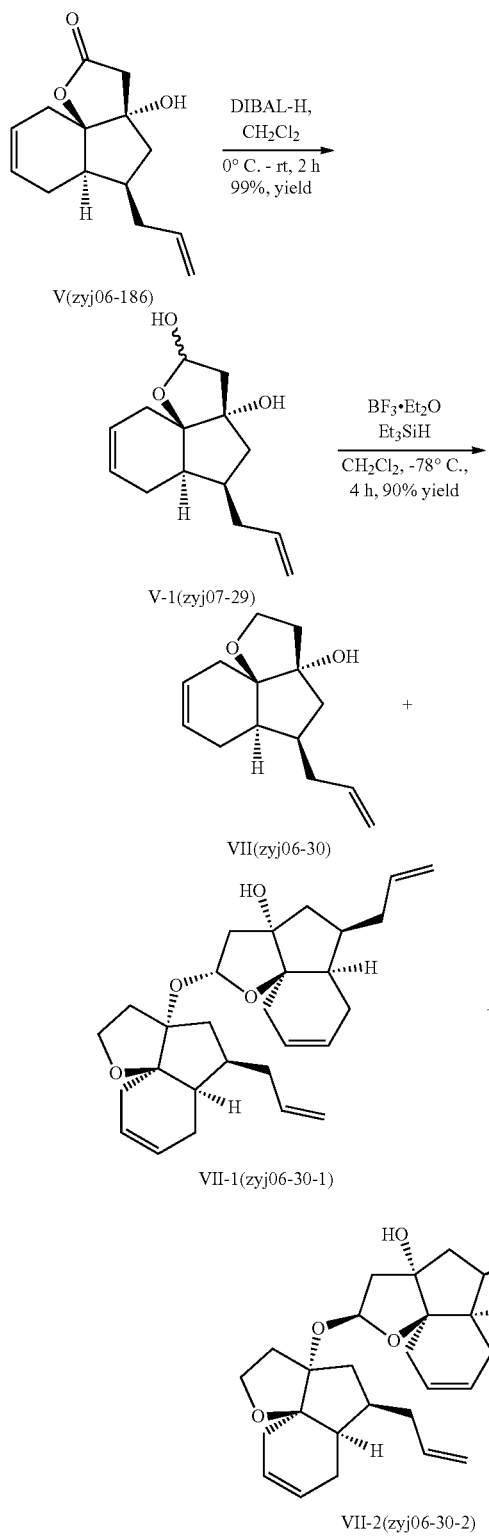

The compound V (100 mg, 0.43 mmol) with test code: Zyj06-186 was dissolved in 20 mL of anhydrous dichloromethane. Then diisobutylaluminum hydride (0.86 mL, 0.86 mmol) was dropped slowly to the flask in an ice bath. The mixture was stirred in an ice bath for 30 minutes. Then the ice bath was removed and the mixture was stirred at room temperature for an hour. When the reaction was completed, 5 mL of methanol was added to the mixture. Then 30 mL of saturated potassium sodium tartrate solution was added to the flask and the mixture was stirred for an hour.

The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 2:1 of v/v as eluent to obtain compound V-1 with test code: Zyj07-29 100 mg, yield: 99%. The amount of compound V-1 and the volume of each reactor are appropriately increased or decreased according to the specific conditions.

The compound V-1 (100 mg, 0.42 mmol) with test code: Zyj06-29 was dissolved in 20 mL of anhydrous dichloromethane. Then tri ethyl silane (98 mg, 0.85 mmol) was dropped to the flask. Boron trifluoride etherate (84 mg, 0.59 mmol) was dropped slowly to the flask at −78° C. The mixture was stirred at −78° C. for 2 hours. Then 10 mL of saturated sodium bicarbonate solution was added to the mixture. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 10:1 of v/v as eluent to obtain compound VII with test code: Zyj07-30 60 mg, compound VII-1 with test code: Zyj07-30-1 15 mg and compound VII-2 with test code: Zyj07-30-2 1.5 mg, yield: 65%. The amount of compound VII and the volume of each reactor are appropriately increased or decreased according to the specific conditions.

When X is allyl, Y is H and $R^2$ is Ac, the specific steps of the synthesis of compound VII are described below:

-continued

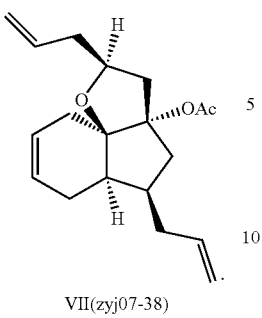

VII(zyj07-38)

-continued

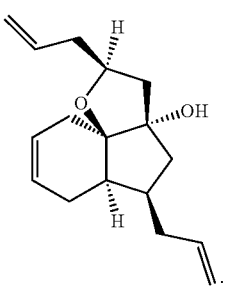

VII(zyj07-98)

Compound V-1 with test code: Zyj07-29 (200 mg, 0.85 mmol) was dissolved in 10 mL of pyridine. Then DMAP (0.21 g, 1.7 mmol) and acetic anhydride (0.86 g, 8.47 mmol) were added to the flask in sequence. The mixture was stirred at room temperature overnight until the reaction was completed. Then 1 mol/L HCl aqueous solution was added to the mixture. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 4:1 of v/v as eluent to obtain compound V-2 with test code: Zyj07-37 200 mg, yield: 74%. The amount of compound V-2 and the volume of each reactor are appropriately increased or decreased according to the specific conditions.

The compound V-2 (100 mg, 0.31 mmol) with test code: Zyj07-37 was dissolved in anhydrous dichloromethane. Then under the atmosphere of nitrogen, allyltrimethylsilane (180 mg, 1.56 mmol) was dropped to the flask. The mixture was stirred at −78° C. for 15 minutes. Boron trifluoride etherate (88 mg, 0.62 mmol) was dropped slowly to the flask at −78° C. The mixture was stirred at −78° C. for 4 hours until the reaction was completed. Then saturated sodium bicarbonate solution was added to the mixture. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 40:1 of v/v as eluent to obtain compound VII with test code: Zyj07-38 93 mg, yield: 97%. The amount of compound VII and the volume of each reactor are appropriately increased or decreased according to the specific conditions.

When X is allyl, Y is H and $R^2$ is H, the specific steps of the synthesis of compound VII are described below:

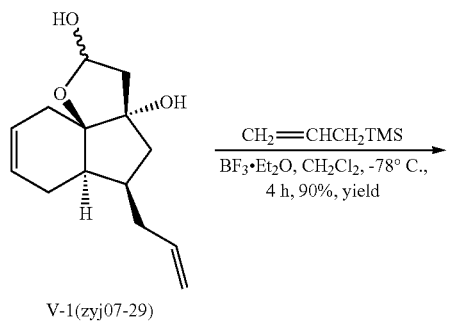

V-1(zyj07-29)

CH$_2$=CHCH$_2$TMS
―――――――――――――→
BF$_3$·Et$_2$O, CH$_2$Cl$_2$, −78° C.,
4 h, 90%, yield The compound V-1 (100 mg, 0.42 mmol) with test code: Zyj07-29 was dissolved in anhydrous dichloromethane. Then under the atmosphere of nitrogen, allyltrimethylsilane (240 mg, 2.1 mmol) was dropped to the flask. The mixture was stirred at −78° C. for 15 minutes. Boron trifluoride etherate (119 mg, 0.84 mmol) was dropped slowly to the flask at −78° C. The mixture was stirred at −78° C. for 4 hours until the reaction was completed. Then saturated sodium bicarbonate solution was added to the mixture. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 10:1 of v/v as eluent to obtain compound VII with test code: Zyj07-98 98 mg, yield: 90%. The amount of compound VII and the volume of each reactor are appropriately increased or decreased according to the specific conditions.

(G) The specific steps of the synthesis of compound VIII are described below:

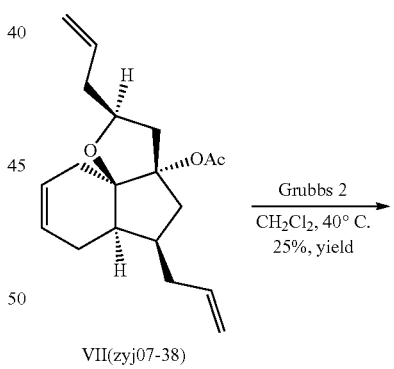

VII(zyj07-38)

Grubbs 2
―――――――→
CH$_2$Cl$_2$, 40° C.
25%, yield

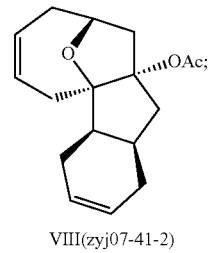

VIII(zyj07-41-2)

wherein: X is allyl; Y is H; $R^1$ is allyl; $R^2$ is Ac.

Compound VII with test code: Zyj07-38 (50 mg, 0.19 mmol) was dissolved in anhydrous DCM. Grubbs 2 (16 mg, 0.019 mmol) was added as a catalyst to the flask under the nitrogen atmosphere. The mixture was heated to reflux at 40° C. for 24 hours. After filtration and concentration under vacuum, the solvent was removed. The residue was purified by column chromatography on silica gel with 200~300 mesh and a mixture of petroleum ether with 60-90° C. fraction and ethyl acetate with 200:1 of v/v as eluent to obtain compound VIII with test code: Zyj07-41-2 13 mg, yield: 25%. The amount of compound VIII and the volume of each reactor are appropriately increased or decreased according to the specific conditions.

(H) General Procedure for the Synthesis of Compound IX, Compound X and Compound XI The specific steps of the synthesis of compound IX, compound X and compound XI are described below:

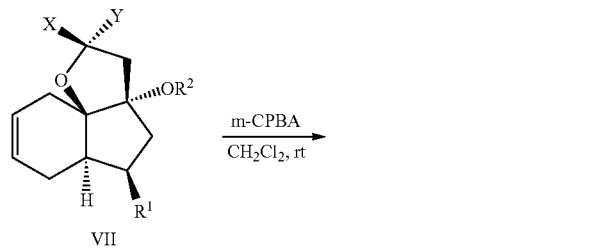

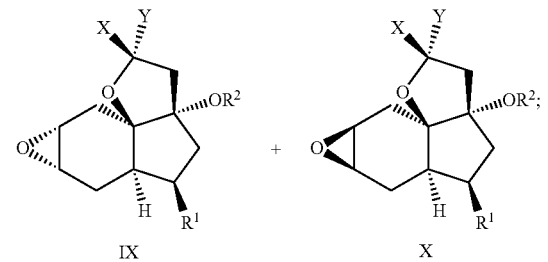

wherein: X is hydrogen, hydroxyl, acetyl or allyl; Y is hydrogen, hydroxyl, acetyl or allyl;

is C=O; $R^1$ is hydrogen or allyl; $R^2$ is hydrogen or Ac.

Compound VII (100 mg, 0.45 mmol) was dissolved in DCM. Then 85% 3-chloroperoxybenzoic acid (0.1 g, 0.5 mmol) was added to the flask in an ice bath and the mixture was stirred for an hour. Then the ice bath was removed and the mixture was stirred at room temperature overnight. Saturated sodium bicarbonate solution was added to the flask and the mixture was stirred for 30 minutes. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 4:1-1:1 of v/v as eluent to obtain separable compounds IX and X, yield: 60%70%. The amount of compound IX and compound X and the volume of each reactor are appropriately increased or decreased according to the specific conditions.

The specific steps of the synthesis of compound XI are described below:

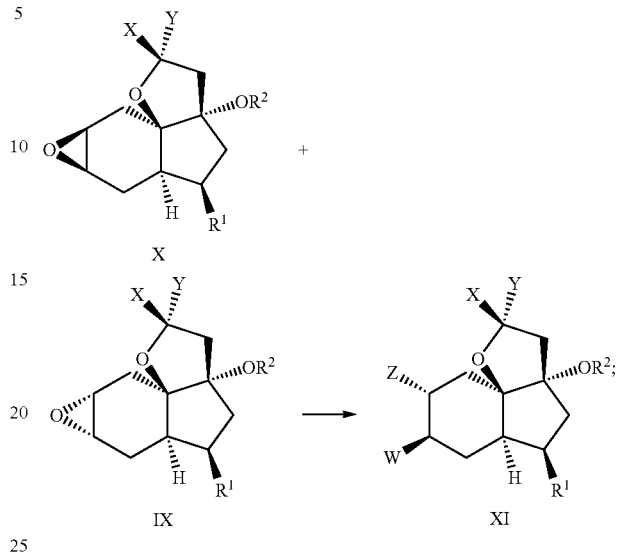

wherein: X is H or allyl; Y is H or allyl;

is C=O; $R^1$ is H or allyl; $R^2$ is H; Z is H, OH or Cl; and W is H, OH or Cl.

When X is H or allyl, Y is H or allyl,

is C=O, $R^1$ is H or allyl, $R^2$ is H, Z is OH or Cl, and W is OH or Cl, the specific steps of the synthesis of compound XI are described below:

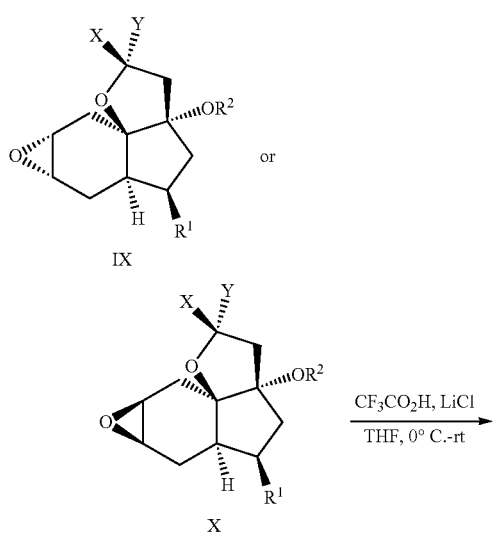

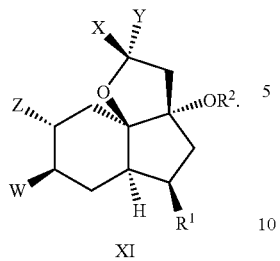

XI

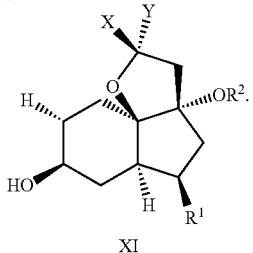

XI

Compound X (70 mg, 0.28 mmol) or compound IX (120 mg, 2.8 mmol) was dissolved in 10 mL of anhydrous THF. TFA (96 mg, 0.84 mmol) was added dropwise to the flask in an ice bath and the mixture was stirred for 15 minutes. Then the ice bath was removed and the mixture was stirred for an hour until the reaction was completed. Saturated sodium bicarbonate solution was added to the flask. The mixture was extracted with DCM and the combined organic layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 2:1-1:2 of v/v as eluent to obtain compound XI, yield: 90%95%. The amount of compound XI and the volume of each reactor are appropriately increased or decreased according to the specific conditions.

When X is H or allyl, Y is H or allyl, $R^1$ is allyl, $R^2$ is H, Z is OH or H, and W is OH or H, the specific steps of the synthesis of the two isomers of compound XI are described below:

Compound X or compound IX (100 mg, 0.42 mmol) was dissolved in anhydrous THF. Under the atmosphere of nitrogen, lithium aluminum hydride (32 mg, 0.84 mmol) was added to the flask in an ice bath. The mixture was stirred in an ice bath for 5 minutes and then the ice bath was removed. The mixture was heated to reflux at 78° C. for 2 hours. When the reaction was completed, water was added slowly to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 2:1-1:2 of v/v as eluent to obtain compound XI, yield: 90%-95%. The amount of compound XI and the volume of each reactor are appropriately increased or decreased according to the specific conditions.

(I) General Procedure for the Synthesis of Compound XII

The specific steps of the synthesis of compound XII are described below:

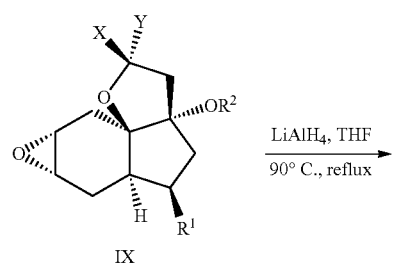

IX

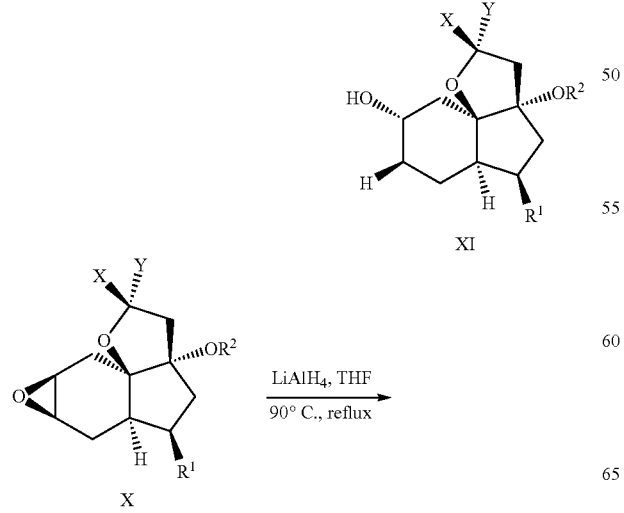

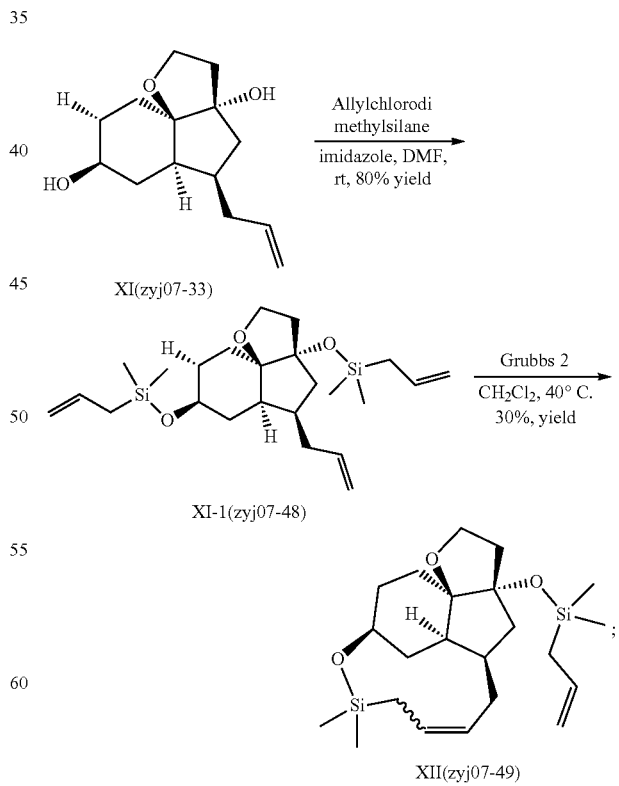

wherein: X is H; Y is H; $R^1$ is allyl; $R^2$ is H; Z is H; W is OH. Compound XI (100 mg, 0.42 mmol) with test code:

Zyj07-33 and imidazole (171 mg, 2.52 mmol) was dissolved in 5 mL of anhydrous DMF. Allylchlorodimethylsilane (170 mg, 1.26 mmol) was added dropwise to the flask and the mixture was stirred at room temperature overnight. Then 20 mL of water was added to the flask. The mixture was extracted with ethyl acetate and the combined ethyl acetate layers were washed with saturated brine, dried over anhydrous sodium sulfate. After filtration and concentration under vacuum, the solvent was removed. The residue was purified by column chromatography on silica gel with 200~300 mesh and a mixture of petroleum ether with 60-90° C. fraction and ethyl acetate with 100:1 of v/v as eluent to obtain compound XI-1 with test code: Zyj07-48 146 mg, yield: 80%. The amount of compound XI-1 and the volume of each reactor are appropriately increased or decreased according to the specific conditions.

Compound (40 mg, 0.12 mmol) was dissolved to the flask in anhydrous DCM, Grubbs 2 (10 mg, 0.012 mmol) was added as a catalyst under the nitrogen atmosphere. The mixture was heated to reflux at 40° C. for 24 hours. After filtration and concentration under vacuum, the solvent was removed. The residue was purified by column chromatography on silica gel with 200~300 mesh and a mixture of petroleum ether with 60-90° C. fraction and ethyl acetate with 200:1 of v/v as eluent to obtain compound XII with test code: Zyj07-49 15 mg, yield: 30%. The amount of compound XII and the volume of each reactor are appropriately increased or decreased according to the specific conditions.

(J) Determination of Fungicidal Activity of the $5_A5_B6_C$ Tricyclic Spironolactone Derivative XI of the Present Invention The fungicidal or fungi growth inhibition activity of the $5_A5_B6_C$ tricyclic spironolactone derivative XI of the present invention is determined by a fungicide growth rate method. The specific steps are: Weigh 1.8 mg of the sample and dissolve it in two drops of dimethylformamide, and then dilute it to 500 μg/mL with a certain amount of aqueous solution containing Tween 20 as an emulsifier. Put 1 mL of the test compound under sterile conditions into the petri dish, and then add 9 mL of PDA culture medium, shake it to make 50 μg/mL drug-containing plate, and use a plate with 1 mL of sterilized water as a blank control. Use a punch with a hole diameter of 4 mm to cut the mycelium disc along the outer edge of the mycelium, move it to the medicine-containing PDA culture plate, and place it in an equilateral triangle. Repeat each treatment for 3 times. Place the petri dish in an incubator with 24±1 Celsius degree condition. After the diameter of the control colony has expanded to 2-3 cm, measure the expanded diameter of each treated fungicide dish and calculate the average value. Calculate the relative fungicidal inhibition rate as compared with the blank control. The test fungi are the species of most typical plant pathogens that actually occur in the field in Chinese agricultural production. Their codes and names are described as follows: AS: *Alternaria solani*, BC: *Botrytis cinerea*, CA: *Cercospora arachidicola*, GZ: wheat *Gibberella zeae*, PI: *Phytophthora infestarts* (Mont.) de Bary, PP: *Physalospora piricola*, PS: *Pellicularia sasakii*, RC: *Rhizoctonia cerealis*, SS: *Sclerotinia sclerotiorum*.

(K) Determination of Insecticidal Activity of the $5_A5_B6_C$ Tricyclic Spironolactone Derivative XI of the Present Invention The pesticidal activity screening of $5_A5_B6_C$ tricyclic spironolactone derivative XI in the present invention was carried out according to the standard operating procedures of Nankai University. The selected insects were *Mythimna separate* (Walker), *Helicoverpa armigera* (Hübner), *Ostrinia furnacalis* and *Caenorhabditis elegans*.

(L) Determination of the Anti-Virus Inactivation Mode Activity of the $5_A5_B6_C$ Tricyclic Spironolactone Derivative XI in the Present Invention Methods of activity screening for the $5_A5_B6_C$ tricyclic spironolactone derivative XI are described as follows and TMV is short expression for Tobacco Mosaic Virus.

Screening method for the anti-TMV inactivation activity of $5_A5_B6_C$ tricyclic spironolactone derivative XI: The in vivo inactivation activity determined by dividing 3 pots of the normal tobacco plants with the same seedling age in one group, and the compound was mixed with the TMV virus solution for 30 minutes. Then the mixture was inoculated to tobacco leaves by rubbing method. The tobacco plants were cultivated in favorable environment with optimal temperature and sunlight. Check the disease lesions occurred three days later. The antiviral effect of the tested compound against TMV was calculated according to the comprehensive number of lesions by the following formula. Each treatment was repeated for 3 times. Use water as a blank control:

$$R = \frac{CK - I}{CK} \times 100;$$

wherein: R is the antiviral effect of the tested compound against TMV, unit: %; CK is the average number of the lesions on the leaves of the control by water treatment, unit: lesion numbers; I is the average number of the lesions on the leaves after the test compound treatment, unit: lesion numbers.

Those descriptions above provided here are examples only. The substituents of the specific compounds are defined as above.

The beneficial effect of the present invention: lead optimization and derivation of the $5_A5_B6_C$ tricyclic spironolactone derivative XI is conducted for the fungicidal activity and anti-virus inducing activity screening.

DETAILED DESCRIPTION OF THE PREFERRED EMBODIMENT

The present invention explained the synthesis, biological activities and applications of $5_A5_B6_C$ tricyclic spironolactone derivative XI more specifically through specific preparation and biological activity measurement examples. The examples are only used to specifically illustrate the present invention and not to limit the present invention; especially biological activities are only illustration and not the limitation of the present invention. Specific examples are described below.

Example 1: Synthesis Methods of the $5_A5_B6_C$ Tricyclic Spironolactone Derivative XI and its Intermediates of the Present Invention The specific methods and steps of the synthesis of the $5_A5_B6_C$ tricyclic spironolactone derivative XI and its intermediates are described in A-I. The amount of $5_A5_B6_C$ tricyclic spironolactone derivative XI and its intermediates, and the volume of each reactor are appropriately increased or decreased according to the specific conditions. The physicochemical properties and structural parameters of the $5_A5_B6_C$ tricyclic spironolactone derivative XI and its intermediates are shown in Table 1.

Example 2: The Insecticidal Activity Measurement Results of the $5_A5_B6_C$ Tricyclic Spironolactone Derivative XI and its Intermediates of the Present Invention The results of the insecticidal activity are shown in Table 2. Table 2 shows that at 100 μg/mL, for *Mythimna separate* (Walker), the insecticidal activity of compound Zyj06-43, compound Zyj06-72, compound Zyj06-161, compound Zyj06-111-2, compound Zyj07-95, compound Zyj07-96, compound Zyj07-29, compound Zyj07-65-2, compound Zyj07-31-2, compound Zyj07-103, compound Zyj07-101 and compound Zyj07-33 were all higher than 30%. The insecticidal activity of compound Zyj06-111-2 was 100% comparable to that of the positive control agent Ryanodine. For *Helicoverpa armigera* (Hübner), the insecticidal activity of Zyj06-111-2 was 50%. For *Ostrinia furnacalis*, the insecticidal activity of Zyj06-111-2 was 40%. For *Caenorhabditis elegans*, the insecticidal activity of compound Zyj06-39, compound Zyj06-177, compound Zyj06-111-2, compound Zyj07-96, compound Zyj06-128, compound Zyj07-29, compound Zyj07-38, compound Zyj07-102, compound Zyj07-67-1 and compound Zyj07-3 0-2 were all higher than 30%. The insecticidal activity of compound Zyj06-177, compound Zyj07-29, compound Zyj07-102 and compound Zyj07-67-1 were all higher than 50%. The positive control agent Ryanodine exhibited no insecticidal activity.

Example 3: The Results of the Fungicidal Activity Determination of the $5_A5_B6_C$ Tricyclic Spironolactone Derivative XI of the Present Invention The code and name of the common phytopathogenic fungi tested in the present invention are described described as follows: AS: *Alternaria solani*, BC: *Botrytis cinerea*, CA: *Cercospora arachidicola*, GZ: wheat *Gibberella zeae*, PI: *Phytophthora infestans* (Mont.) de Bary, PP: *Physalospora piricola*, PS: *Pellicularia sasakii*, RC: *Rhizoctonia cerealis*, SS: *Sclerotinia sclerotiorum*. These strains are very well represented the species of most common pathogens that occurred in the field in the Chinese agricultural production.

The results of the growth inhibition rates are shown in Table 2. Table 2 shows that at 50 μg/mL, all the $5_A5_B6_C$ tricyclic spironolactone derivatives XI synthesized by the present invention have different degrees of fungicidal activity.

For AS: Compound Zyj06-39, compound Zyj06-43, compound Zyj06-92-2, compound Zyj06-166, compound Zyj07-95, compound Zyj06-113-3, compound Zyj06-167, compound Zyj07-96, compound Zyj06-128, compound Zyj06-175, compound Zyj07-98, compound Zyj07-64, compound Zyj07-103, compound Zyj07-32, compound Zyj07-92 and compound Zyj07-49 all had a fungicidal activity higher than 60%, they were more higher with over 35% of inhibition than that of positive control Ryanodine.

For BC: Compound Zyj06-72, compound Zyj06-82, compound Zyj06-113-2, compound Zyj07-95, compound Zyj06-180, compound Zyj06-113-3, compound Zyj06-189, and compound Zyj07-37-1, compound Zyj07-98, compound Zyj07-13, compound Zyj07-67-1, compound Zyj07-67-2, compound Zyj07-14, compound Zyj07-101, compound Zyj07-33, compound Zyj07-48, compound Zyj07-46 all exhibited a fungicidal activity higher than 50%, they all were higher for over 25% than that of positive control Ryanodine.

For CA: compound Zyj06-39, compound Zyj06-43, compound Zyj06-72, compound Zyj06-92-2, compound Zyj06-111-2, compound Zyj06-166, compound Zyj07-95, and compound Zyj06-187, compound Zyj06-113-3, compound Zyj07-96, compound Zyj07-38, compound Zyj07-98, compound Zyj07-64, compound Zyj07-32, compound Zyj07-92, compound Zyj07-3 0-2, compound Zyj07-49 and compound Zyj07-41-2 all exhibited a fungicidal activity higher than 50%, they all showed more than 40% higher than that of positive control Ryanodine.

For GZ: compound Zyj06-39, compound Zyj06-43, compound Zyj06-92-2, compound Zyj07-95, and compound Zyj06-187, compound Zyj07-96, compound Zyj06-128, compound Zyj07-98, compound Zyj07-92 and compound Zyj07-49 all exhibited a fungicidal activity higher than 50%, they all showed more than 30% higher than that of positive control Ryanodine.

For PI: compound Zyj07-101 and compound Zyj07-32 exhibited a fungicidal activity higher than 60%, they all showed more than 30% higher than that of positive control Ryanodine.

For PP: compound Zyj06-39, compound Zyj06-43, compound Zyj06-92-2, compound Zyj06-111-2, compound Zyj07-95, compound Zyj06-187, compound Zyj06-113-3, compound Zyj07-96, compound Zyj06-189, compound Zyj07-37-1, compound Zyj07-98, compound Zyj07-64, compound Zyj07-31-1, compound Zyj07-103 and compound Zyj07-101 compound Zyj07-33, compound Zyj07-32, compound Zyj07-92, compound Zyj07-3 0-1, compound Zyj07-49, compound Zyj07-41-2 all exhibited a fungicidal activity higher than 50%, they all showed more than 30% higher than that of positive control Ryanodine. Most compounds listed above exhibited a fungicidal activity of 80%-90%.

For PS, compound Zyj06-39, compound Zyj07-96 and compound Zyj07-64 all exhibited a fungicidal activity higher than 60%, they all showed more than 30% higher than that of positive control Ryanodine.

For RC: compound Zyj06-3 9, compound Zyj06-43, compound Zyj06-92-2, compound Zyj07-95, compound Zyj07-96, compound Zyj06-128, compound Zyj07-98, compound Zyj07-64, compound Zyj07-92, compound Zyj07-49 and compound Zyj07-41-2 all exhibited a fungicidal activity higher than 70%, they all showed more than 30% higher than that of positive control Ryanodine. Most compounds exhibited a fungicidal activity of higher than 90%.

For SS, compound Zyj06-39, compound Zyj06-43, compound Zyj06-72, compound Zyj06-82, compound Zyj06-161, compound Zyj06-177, compound Zyj07-95, compound Zyj06-180, compound Zyj06-127 and compound Zyj06-113-3 compound Zyj07-96, compound Zyj06-186, compound Zyj07-29, compound Zyj07-37-1, compound Zyj07-37-2, compound Zyj07-98, compound Zyj07-30, compound Zyj07-13, compound Zyj07-67-1, compound Zyj07-67-2, compound Zyj07-31-2, compound Zyj07-103, compound Zyj07-14, compound Zyj07-100, compound Zyj07-101, compound Zyj07-68, compound Zyj07-32, compound Zyj07-48, compound Zyj07-46, compound Zyj07-3 0-1, compound Zyj07-3 0-2, compound Zyj07-49 and compound Zyj07-41-2 all exhibited a fungicidal activity higher than 50%, they all showed more than 30% higher than that of positive control Ryanodine.

As described above, the target compounds of the present invention and the most intermediates have relatively broader spectrum of fungicidal activity.

Example 4: The Anti-Tobacco Mosaic Virus (TMV) Activity of the $5_A5_B6_C$ Tricyclic Spironolactone Derivative XI of the Present Invention Described as Follows The results of anti-TMV activities were shown in Table 2. Table 2 shows: under the activation condition, compound Zyj06-39, compound Zyj06-72, compound Zyj06-80, compound Zyj06-82, compound Zyj06-177, compound Zyj06-92-2, compound Zyj06-166, compound Zyj07-95, compound Zyj06-127, compound Zyj06-187, compound Zyj06-113-3, compound Zyj06-167, compound Zyj06-186, compound Zyj06-189, compound Zyj06-175, compound Zyj07-29, compound Zyj07-38, compound Zyj07-98, compound Zyj07-30, compound Zyj07-64, compound Zyj07-65-1, compound Zyj07-103, compound Zyj07-100, compound Zyj07-101, compound Zyj07-68, compound Zyj07-69, compound Zyj07-48, compound Zyj07-46 and compound Zyj07-92 all exhibited a over 30% of anti-TMV activity higher, they were equivalent to that of positive control virazole. While, the positive control Ryanodine exhibited no anti-TMV activity.

Example 5: The Toxicity of the $5_A5_B6_C$ Tricyclic Spironolactone Derivative XI and its Intermediates Against Honey Bees in the Present Invention The $5_A5_B6_C$ tricyclic cyclolactone derivative XI and its intermediates of the present invention are safe against beneficial insect *Apis mellifera* ligustica Spin. The mortality rate of most compounds is 0 at 10 μg a.i./bee, and only a few compounds showed 5% or 10% of death rate. The determination results are shown in Table 3. The expected $LC_{50}$ of these compounds are far higher than the $LC_{50}$ of low-toxicity compounds issued by The Ministry of Agriculture and Rural Affairs of the People's Republic of China. Due to the structural modification as compared with Ryanodine, the compound of the present invention exhibited an unexpected improvement advantage in safety, the effects of our studies got unexpectedly effects.

The target compounds of the present invention have excellent biological activity. Therefore, anyone of these compounds can form a pesticide composition containing a $5_A5_B6_C$ tricyclic spironolactone derivative XI as an active ingredient. The pesticide composition generally contains 0.1% to 99% of an active ingredient by weight, 99.9% to 1% of a solid or liquid pesticidal adjuvant by weight, and 0 to 25% of a surfactant by weight.

The target compound of the present invention can also form a pesticide mixture comprising anyone of the $5_A5_B6_C$ tricyclic spironolactone derivatives XI and other insecticides, acaricides, fungicides or antiviral agents as an active ingredient, wherein a ratio of the $5_A5_B6_C$ tricyclic spironolactone derivatives XI to the other insecticides, acaricides, fungicides or antiviral agents ranging from 1%: 99% to 99%: 1%, and a mass percentage of the active ingredients is 0.1% to 99%, a mass percentage of a solid or liquid pesticidal adjuvant is 99.9% to 1%, and a mass percentage of surfactant is 0 to 25%. The pesticide mixture can be used to control pests, mite, phytopathogen and plant viruses in agriculture, forestry, and horticulture. The specific examples are described as follows.

Example 6: Application of Pesticide Compositions Containing $5_A5_B6_C$ Tricyclic Spironolactone Derivative XI in the Present Invention in the Protection of Agriculture, Forestry and Horticultural Plants The present invention also relates to a pesticide composition containing a $5_A5_B6_C$ tricyclic spironolactone derivative XI as an active ingredient. The above-mentioned pesticide composition generally comprises 0.1% to 99% by weight, preferably 0.1% to 95% by weight of a compound of formula XI, 99.9% to 1% by weight, preferably 99.8% to 5% by weight of a solid or liquid pesticidal adjuvant, and 0 to 25% by weight, preferably 0.1% to 25% by weight of a surfactant. For the pesticide composition containing the $5_A5_B6_C$ tricyclic spironolactone derivative XI as an active ingredient, the suitable formulation was selected from the group consisting of a seed treatment emulsion, an aqueous emulsion, a large granule, a microemulsion, a water-soluble granule, a soluble concentrate, and a water-dispersible granule. Poison valley, aerosol, block bait, slow-release block, concentrated poison bait, capsule granules, microcapsule suspension, dry seed powder, emulsifiable concentrate, wettable powder electrostatic spray, water-in-oil emulsion, oil-in-water emulsions, aerosol cans, fine granules, aerosol candles, aerosol cans, aerosol sticks, seed treatment suspensions, aerosol tablets, aerosol pills, granular poisonous baits, thermal aerosols, paints, fine particles, oil suspensions, oil-dispersible powder, flake bait, thick glue, pouring agent, seed coating agent, spreading agent, suspension emulsion, film-forming oil agent, soluble powder, water soluble powder for seed treatment, ultra-low capacity suspension agent, tracking powder, ultra-low capacity liquid agent, or a water-dispersible powder for wet dressing.

Although commercial product formulations are preferably as concentrates, however, end users typically use the dilute formulations.

The $5_A5_B6_C$ tricyclic spironolactone derivative XI of the present invention is in combination with a commercial insecticide as a mixture for controlling plant insects in agriculture, forestry and horticulture.

The $5_A5_B6_C$ tricyclic spironolactone derivative XI of the present invention is in combination with agriculturally acceptable adjuvants and one or more of the following commercial insecticides for preparing insecticide mixtures.

The commercial insecticide was at least one member selected from the group consisting of chlorpyrifos, diazepam, acetamiprid, methylaminoavermectin, mibemycin, avermectin, spinosyn, fenvalerate, esfenvalerate, cypermethrin, beta-cypermethrin, cyhalothrin, deltamethrin, fenpropathrin, cyfluthrin, permethrin, permethrin, S-Bioallethrin, bifenthrin, permethrin, etofenprox, flumethrin, fluvalinate, imidacloprid, acetamiprid, nitenpyram, chlorothiazoline, thiacloprid, thiamethoxam, clothianidin, dinotefuran, clonidine, dinotefuran, diflubenzuron, chlorfenuron, flubendicarb, diflubenzuron, flubenzuron, flufludicarb, acetamiprid, fenflubenzuron, chlorflubenzuron, fluflubenzuron, Noviflumuron (CAS No. 121451-02-3), flufenazone, novaluron, fluoxuron, Bay sir 6874 {1-[(3,5-dichloro-4) 4-nitrophenoxyphenyl 3-3-(2-chlorobenzene)-urea], Bay SIR-8514 {1-(4-trifluoromethoxyphenyl)-3-(2-chlorobenzene)-urea}, pyraclostrobin, bistrifluron, fufenozide, tebufenozide, halofenozide, methoxyfenozide, chromafenozide, dimethoate, omethoate, dichlorvos, methamidophos, triazophos, quintiophos, pyridaphenthion, isazophos, isoprocarb, tricarnam, pirimicarb, tsumacide, isoprocarb, carbendazim, fenobucarb, N-methyl 2,3-dimethylphenyl carbamate, carbaryl, benfuracarb, carbosulfan, fenitrothion, bromopropylate, hexythiazox, fenpyroximate, pyridaben, tetrabenazine, propargite, diafenthiuron, benfuracarb, pymetrozine, spirodiclofen, spiromesifen, spirotetramat, butenaflpronil, aza cyclotin, buprofezin, ethoprophos, Fipronil, monosultap, bisultap, chlorantraniliprole, flubendiamide, tetraniliprole, cyantraniliprole, tolfenpyrad, tebufenpyrad, chlorfenapyr, pyrazinone, etoxazole, tebufenpyrad, pyridone, pyriproxyfen, and emamectin.

The mass percentage of the $5_A5_B6_C$ tricyclic spironolactone derivative XI of the present invention in the insecticide mixture is 1%-90%, and the mass ratio of the $5_A5_B6_C$ tricyclic spironolactone derivative XI to the above described commercial insecticides was from 1%:99% to 99%:1%.

The formulation suitable for the insecticide mixture was selected from a seed treatment emulsion, water emulsion, large granule, microemulsion, water-soluble granule, soluble concentrate, water-dispersible granule, poisonous valley, aerosol, and block poison bait, slow-release blocks, concentrated poison bait, capsule granules, microcapsule suspensions, dry seed powders, emulsifiable concentrates, wettable powders, electrostatic sprays, water-in-oil emulsions, oil-in-water emulsions, smoke cans, fine granules, smoke candles, smoke tube, smoke stick, seed treatment suspension agent, smoke tablet, smoke pill, granular poison bait, hot aerosol, medicinal paint, fine particles, oil suspension, oil dispersible powder, flake poison bait, thick glue, splash pouring Agent, seed coating agent, spreading agent, suspension emulsion, film-forming oil agent, soluble powder, seed treatment water-soluble powder, ultra-low-capacity suspending agent, tracking powder, ultra-low-volume liquid agent, or wet-seed water-dispersible powder.

The plant suitable for the pesticide mixture was selected from rice, wheat, barley, oats, corn, sorghum, sweet potato, potato, cassava, soybean, pea, broad bean, pea, mung bean, adzuki bean, cotton, silkworm, peanut, rape, sesame, Sunflower, beet, sugar cane, coffee, cocoa, *ginseng*, fritillary, rubber, coconut, oil palm, sisal, tobacco, tomato, pepper, radish, cucumber, cabbage, celery, mustard, shallot, garlic, watermelon, melon, cantaloupe, *papaya*, apple, citrus, peach tree, tea, wild vegetables, bamboo shoots, hops, pepper, banana, *papaya*, orchid, or bonsai.

Insects controlled by the above mentioned insecticide mixture were selected from astatic migratory locusts, *Gastrimargus marmoratus*, *Oxya chinensis* Thun berg, *Patanga japonca bolivar*, *Gryllotlp unispin sussure*, *Gryllotalpa orientalis burmeister*, *Chloethrips oryzae*, *Thrips alliorum* (Priesner), *Hercinothrips femoralis*, *Haplothrips aculeatus*, *Haplothrips tritici*, *Trialeurodes vaporariorum* (Westwood), *Bemisia tabaci*, *Nephotettix bipunctatus* (fabricius), *Cicadella viridis*, *Empoasca biguttula* (Ishida), *Lycorma delicatula*, *Nilaparvata lugens* (Stal), *Sogatella furcifera* (Horvath), *Laodelphax striatellus* (Fallén), *Perkinsiella saccharicida* (Kirkaldy), *Aphis gossypii Glover*, *Schizaphisgraminum*, *Sitobion avenae* (fabricius), *Myzus persicae* (Sulzer), *Melanaphis sacchari*, *Lipaphis erysimi*, *Icerya purchasi*, *Pseudaulacaspis pentagona*, *Unaspis yanonensis*, *Quadraspidiotus pemiciosus* (Comstock), *Ericerus pela Chavannes*, *Ceroplastes rubens* (Masked), *Didesmococcus koreanus Borchsenius*, *Stephanitis nashi Esaki et Takeya*, *Slephanitis typical* (Distant), *Lyctocoris*, *Oriu minuius Linnaeus*, *Ochrochira camelina*, *Leptocorisa acuta* (Thunberg), *Niphe elongata*(Dallas), *Scotinophara lurida* (Burmeister), *Nezara viridula Linnaeus*, *Lygocoris lucorum* (Meyer-Dur.), *Adelphocoris suturalis*, *Chrysopa septempunctata*, *Chrysopaformosa Brauer*, *Chrysoperla sinica* Tjeder, Tineidae, *Tinea pellionella*, *Cnidocampa flavescens* (Walker), *Setora postornata*, *Thosea sinensis*, *Sitotroga cerealella* Olivier, *Pectinophora gossypiella*, *Brachmia macroscopa*, *Plutella xylostella*, *Carposina niponensis* Walsingham, *Leguminivora glycinivorella* (Matsumura), *Carposina niponensis* Walsingham, *Spilonota lechriaspis*, *Hornona coffearia* (Meyrick), *Adoxophyes cyrtosema*, *Chilo suppressalis*, *Etiella zinckenella*, *Ostrinia nubilalis*, *Tryporyza incertulas*, *Hellula undalis fabricius*, *Cnaphalocrocis medinalis*, *Proceras venosatum* (W alker), *Sylepta derogata fabricius*, *Dichocrocis punctiferalis*, *Mythimna separata* (W alker), *Spodoptera litura* (fabricius), *Naranga aenescens* Moore, *Anomis flava* (fabricius), Asparagus caterpillar, *Sesamia inferens*, *Helicoverpa armigera*, *Eanas cupreoviridis* W alker, *Agrotis ipsilon*, *Agrotis tokionis*, *Agrotis segetum*, *Porthesia similis* (Fueszly), *Lymantria dispar*, *Agrius convolvuli*, *Clanis bilineata*, *Parnara guttata* Bremer et Grey, *Pelopidas mathias* (Fabrieius), *Papilio xuthus*, *Papilio polytes*, *Pieris rapae*, *Pyrameis indica* Herbst, *Acraca issorie* (Hubner), *Epicauta gorhami*, *Calosoma auropunctatum*, *Cychrus convexus*, *Anisodactylus signatus*, *Pleonomus canaliculatus*, *Agriotes subrittatus* Motschulsky, *Trogoderma granarium*, *Attagenus minutus* Olivier, *Citrus* gilding bug, *Lampra limbata* Gebler, *Tenebrio molitor*, *Tenebrio obscurus*, *Tribolium castaneum*, *Tribolium conjusum*, *Verdigris aureus*, *Holotrichia parallela*, *Holotrichia oblita*, *Apriona germari*, *Anoplophora chinensis*, *Nadezhdilla cantori* (Hope), *Aromia bungii*, *Colaphellus bowringi* Baly, *Phaedon brassicae*, *Aulacophora femoralis*, *Phyllotreta striolata*, *Callosobruchus chinensis*, *Bruchus pisorum* (Linnaeus), *Bruchus rufimanus*, *Sitophilus zeamais* Motschusky, *Sitophilus oryzae*, *Dolerus tritici*, *Hoplocampa pyricola*, *Pterocormus generosus*, *Vulgichneumon leucaniae* Uchida, *Charops* bicolor (Szepligeri), *Campoletis chorideae* Uchida, *Xanthopimpla stemmator* Thunberg, mosquitoe, fly, horsefly, *Sitodiplosis mosellana* Gehiri, *Contarinia tritici*, *Orseoia oryzae*, *Tetradacus citri*, *Bactrocera cucurbitae*, *Agromyza cinerascens* Macquart *Liriomyza sativae*, *Melanagromyza sojae*, *Meromyza saltatrix*, *Hylemyia platura* Meigeri, *Delia antigua* Meigeri, *Phorbia brassicae*, *Exorista emits*, *Lydella grisescens*, or *Mythimna seperata* (W alker). The $5_A5_B6_C$ tricyclic spironolactone derivative XI of the present invention is in combination with a commercial acaricide to fome an acricide mixture for controlling phytophagous mites in agriculture, forestry and horticulture.

The $5_A5_B6_C$ tricyclic spironolactone derivative XI of the present invention is combined with any agriculturally acceptable pesticidal adjuvant agent and any one or more of the following commercial acaricides to prepare an acaricide mixture and to be applied to control plant mites.

The commercial acaricide was selected from aza cyclotin, cyhexatin, fenbutatin, phos cyclotin, chlorfenvinphos, dimethylvinphos, crotoxyphos, dichlorvos, heptenophos, mevinphos, monocrotophos, orthodibrom, chlorpyrifos, pyrimithate, chloromethimthion, omethoate, dioxathion, ethionphos, malathion, methacrifos, fenthion, phoxim, silesan, quinalphos, sulfotep, triazophos, aphid, vamidothion, isocarbophos, methamidophos, amiprophos, chloroimidophos, imithion, acrinathrin, bifenthrin, cyfluthrin, gamma cyhalothrin, fenpropathrin, flucythrinate, flumethrin, fluvalinate, brofluthrinate, bifenazate, fenothiocarb, aldicarb, butocarboxim, oxamyl, thiocarboxime, thiofanox, benomyl, carbanolate, carbofuran, carbosulfan, tsumacide, promacyl, formetanate, semiamitraz, formetanate, amitraz, chlordimeform, benzyl benzoate, bromopropylate, cyflumetofen, acequinocyl, acarioquinone, fluoroaphis acari, fluorozorea, liuyangmycin, abamectin, doramectin, eprinomectin, ivermectin, seramin, moxidectin, pyrethrin, nicotine, matrine, azadirachtin, rotenone, tebufenpyrad, pyridaben, fenpyroximate, clofentezine, propargite, hexythiarizonaox, spirodiclofen, fluacrypyrim, chlorfenson, propargite, or pyridaben.

The mass percentage of the $5_A5_B6_C$ tricyclic spironolactone derivative XI of the present invention in the mixed acaricide is 1%-90%, and the mass ratio of the $5_A5_B6_C$ tricyclic spironolactone derivatives XI to the above described commercial acaricide was from 1%:99% to 99%:1%.

The formulation of the acaricide mixture was selected from wettable powder, microcapsule suspension, dispersible liquid preparation, dispersible solid preparation, seed treatment emulsion, water emulsion, large granule, microemulsion, oil suspension agent, pesticide package coated seeds, water-soluble granules, soluble concentrates, water-dispersible granules, poison valley, aerosol, block poison bait, slow-release block, concentrated poison bait, capsule granules, dry seed powder, emulsifiable concentrate, wettable powder electrostatic spray, water-in-oil emulsion, oil-in-water emulsion, aerosol cans, fine granules, aerosol candles, aerosol cans, aerosol sticks, seed treatment suspensions, aerosol tablets, aerosol pills, granular poisonous bait, hot aerosols, medicines Lacquer, seed treatment liquid, granules, oil-dispersible powder, flake poison bait, thickening agent, pouring agent, spreading agent, suspension emulsion, film-forming oil agent, soluble powder, seed treatment water-soluble powder, ultra-low capacity suspending agent, tracking powder, ultra-low-volume liquid, or water-dispersible powder for wet dressing.

The plant suitable for the acaricide mixture was selected from rice, wheat, barley, oats, corn, sorghum, sweet potato, potato, cassava, soybean, pea, broad bean, pea, mung bean, adzuki bean, cotton, silkworm, peanut, rape, sesame, Sunflower, beet, sugar cane, coffee, cocoa, ginseng, fritillary, rubber, coconut, oil palm, sisal, tobacco, tomato, pepper, radish, cucumber, cabbage, celery, mustard, shallot, garlic, watermelon, melon, cantaloupe, papaya, apple, citrus, peach tree, tea, wild vegetables, bamboo shoots, hops, pepper, banana, papaya, orchid, or bonsai.

The mites suitable for the acaricide mixture were selected from Tetranychidae, Tenuipalpidae, *Trichofurus funis*, Eriophyidae, *Tetranychus*, or Eriophyidae, which were worldwide agricultural spider mites, forestry spider mites, horticultural spider mites and health spider mites.

The $5_A5_B6_C$ tricyclic spironolactone derivative XI of the present invention is in combination with a commercial fungicide to form a fungicidal mixture for controlling plant diseases in agriculture, forestry and horticulture.

The $5_A5_B6_C$ tricyclic spironolactone derivative XI of the present invention is in combination with any one or more of agriculturally acceptable adjuvants and the following commercially fungicides for preparing a fungicide mixture.

The commercial fungicide was selected from benzothiadiazole, tiadinil, methiadinil, 4-methyl-1,2,3-thiadiazole-5-carboxylic acid, sodium 4-methyl-1,2,3-thiadiazole-5-carboxylate, ethyl 4-methyl-1,2,3-thiadiazole-5-carboxylate, ethyl 4-bromomethyl-1,2,3-thiadiazole-5-carboxylate, ethyl 4-iodomethyl-1,2,3-thiadiazole-5-carboxylate, 4-bromomethyl-5-methyl-1,2,3-thiadiazole, 4-iodomethyl-5-methyl-1,2,3-thiadiazole, ethyl 4,4-dibromomethyl-1,2,3-thiadiazole-5-carboxylate, 3,4-dichloroisothiazole-5-carboxylic acid, sodium 3,4-dichloroisothiazol-5-carboxylate, ethyl 3,4-dichloroisothiazol-5-carboxylate, DL-β-aminobutyric acid, isotianil, ribavirin, antofin, ningnanmycin, methionil, salicylic acid, cytosinpeptidemycin, dichloroisonicotinic acid, probenazole, cymoxanil, formex, ziram, mancozeb, aliette, methylthiocarb, chlorothalonil, fenaminosulf, procymidone, fenpropidin, thiophanate methyl, topsin, mefenoxam, salicylic acid, flumorph, dimethomorph, metalaxyl-M, benalaxyl-M, diclocymet, flusulfamide, tolylfluanid, thifluzamide, flutolanil, tecloftalam, carpropamid, cyflufenamid, fenhexamid, fenoxanil, silthiopham, furametpyr, penthiopyrad, mandipropamid, zoxamide, fenfuram, carboxin, chlozolinate, iprodione, azoxystrobin, dimoxystrobin, fluoxastrobin, kresoxim-methyl, metominostrobin, orysastrobin, picoxystrobin, pyraclostrobin, trifloxystrobin, enestroburin, fenaminstrobin, azaconazole, bromuconazole, cyproconazole, difenoconazole, diniconazole, diniconazole-M, epoxiconazole, fenbuconazole, fluoroquinazole, flusilazole, flutriafol, hexaconazole, imidazole, ipconazole, metconazole, myclobutanil, penconazole, propiconazole, prothioconazole, simeconazole, tebuconazole, tetraconazole, triadimenol, triticonazole, bitertanol, thiabendazole, furidazol, imazalil, imazalil-M, prochloraz, triflumizole, cyazofamid, fenamidone, oxpoconazole, pefurazoate, famoxadone, pyrisoxazole, hymexazol, oxadixyl, ethaboxam, etridiazole, octhilinone, benthiazole, dodemorph, fenpropimorph, tridemorph, fenpiclonil, fludioxonil, fluazinam, pyrifenox, boscalid, fluopicolide, cyprodinil, diflumetorim, ferimzone, mepanipyrim, pyrimethanil, fenarimol, chinomethionate, dithianon, ethoxyquinoline, hydroxyquinoline, proquinazid, quinoxyfen, diethofencarb, iprovalicarb, benthiavalicarb-isopropyl, propamocarb, methasulfocarb, ediphenphos, Iprobenfos, pyrazophos, tolclofos-methyl, blastidin, kasugamycin, polyoxins, polyoxin, validamycin, validamycin, streptomycin, metalaxyl, furaxyl, benalaxyl, furamide, Mepronil, carbendazim, benomyl, methylthiocarb, triazolone, bupirimate, dimethirimol, ethellorimol, captafol, captan, folpet, vinclozolin, Fluorochlorine *sclerotium*, dimethachlon, isoprothiolane, kitazin, bismerthiazol, quintozene, mancozeb, propineb, phosethyl-al, Sulphur, Bordeaux solution, copper sulfate, copper oxychloride, cuprous oxide, copper hydroxide, metrafenone, pencycuron, diclomezine, phthalide, pyroqmlon, spiroxamine, tricyclazole, triforine, dofidine, guazatine, guazatine, dicloran, elvaron, tolylfluanid, indoxyl ester, fenaminosulf, oxolinic acid, probenazole, bronopol, iodomethane, metham, methyl isothiocyanate, dazomet, Nemamort, lythidathion, cadusafos, fensulfothion, weibaimu, dilinyl ester, cotton wool, dichloroisopropyl ether, thiazol, thiophosphine, fossophos, thionazin, fenamiphos, ethoprophos, dichlofenthion, isazofos, fosthietan, oxamyl, aldicarb, carbofuran, sulfuryl fluoride, dichloropropene, dichloroisonicotinic acid, or probenazole.

The mass percentage of the $5_A5_B6_C$ tricyclic spironolactone derivative XI of the present invention in the fungicide mixture was 1%-90%, and the mass ratio of the $5_A5_B6_C$ tricyclic spironolactone derivatives XI to the above described commercially fungicide was from 1%:99% to 99%:1%.

The formulation suitable for the fungicide mixture was selected from wettable powder, microcapsule suspension, dispersible liquid preparation, dispersible solid preparation, seed treatment emulsion, water emulsion, large granule, microemulsion, oil suspensions, pesticide-coated seeds, water-soluble granules, soluble concentrates, water-dispersible granules, poison valleys, aerosols, block poison baits, slow-release blocks, concentrated poison baits, capsule granules, dry seed dressing powder, emulsifiable concentrate, electrostatic spray of wettable powder, water-in-oil emulsion, oil-in-water emulsion, aerosol cans, fine granules, aerosol candles, aerosol cans, aerosol sticks, seed treatment suspensions, aerosol tablets, aerosol pills, granular poison bait, hot aerosol, medicinal lacquer, seed treatment liquid, fine particles, oil-dispersible powder, flake poison bait, thick glue, pouring agent, spreading agent, suspension emulsion, film-forming oil agent, soluble powder, seed treated with water-soluble powders, ultra-low-volume suspensions, tracking powders, ultra-low-volume liquids, or water-dispersed powders for wet dressing.

The plant suitable for the fungicide mixture was selected from rice, wheat, barley, oats, corn, sorghum, sweet potato, potato, cassava, soybean, pea, broad bean, pea, mung bean, adzuki bean, cotton, silkworm, peanut, rape, sesame, Sunflower, beet, sugar cane, coffee, cocoa, ginseng, fritillary, rubber, coconut, oil palm, sisal, tobacco, tomato, pepper, radish, cucumber, cabbage, celery, mustard, shallot, garlic, watermelon, melon, cantaloupe, papaya, apple, citrus, peach tree, tea, wild vegetables, bamboo shoots, hops, pepper, banana, papaya, orchid, or bonsai.

The disease controlled by the fungicide mixture was selected from *Puccinia striiformis* West; *Fusarium graminearum* Sehw. or *F. ardenaceum* (Fr.) Sacc.; *Blumeria graminis* F. sp. *tritici*; Wheat yellow mosaic virus, WYMV; *Gerlachia nivalis; Bipolaris sorokiniana* (Sacc. ex Sorok.) Shoem.; *Tilletia caries* or *Toilletia foetida; Gaeumannomyces graminis* var; *Rhizoctonia cereadis* van der Hoeven apud. Boerema & Verhoeven; *Sclerophthora macrospora* (Sacc.) Thrium., Shaw et *Narasimhan* var. *triticina* Wang & Zhang, J. Yunnan Agr.; *Phytophthora infestans* (Mont.) de Bary; *Synchytrium endobioticum* (Schilberszky) percivadl; *Streptomyces scabies* (Thaxter) Waks. et Henvici; *Alternaria solani*. Sorauer; *Clavibacter michiganensis* subsp. *sepedonicus; Ralstonia solanacearum* E. F. Smith; *Erwinia carotovora* subsp. *Atroseptica* (Van Hall) Dye; Potato virus and viroid disease including Pottao Virus Y, PVY; *Pectobacterium carotovorum* subsp. *carotovorum, P. atrosepticum* or *Dickeya chrysanthemi; Fusarium* spp., *Fusarium sambicinum, Fusarium solani, Fusarium solani* var. *coeruleum, Fusarium avenaceum, Fusarium sulphureum, Fusarium oxysporum, Fusarium equiseti, Fusarium acuminatum, Fusarium graminearum, Fusarium scirpi, Fusarium crookwellense, Fusarium trichothecioides, Fusarium sporotrichioides, Fusarium redolens, Fusarium moniliforme, Fusarium moniliforme* var. *intermedium, F. moniliforme* var. *zhejiangense, Fusarium culmorum, Fusarium tricinctum* or *Fusarium semitectum; Verticillium dahliae* Kleb.; *Rhizoctonia solanikuhn; Ralstonia solanacearum* E. F. Smith; *Clavibacter michiganense* subsp. *sepedonicum* (Spieckermann & Kotthoff) Davis, Gillaspie, Vidaver and Harris; *Erwinia carotovora* subsp. *atroseptica* (Van Hall) Dye; *Erwinia carotovora* subsp. *carotovora* (Jones) Bergeyetal., *Erwinia carotovora* subsp. *atroseptica* (VanHall) Dye or *Erwinia chrysanthemi* Burkholder, McFaddenet Dimock; *Fusarium oxysporum* f. sp. *vesinfectum* (Atk.) Snyder et Hansen; *Verticillium dahliae* Kleb. or *Verticillium alboatrum* Reinke et Berthold; *Xanthomonas campestris* pv *malvacearum* (E F Smith) Dowson; Cotton red leaf blight disease; *Rhizoctonia solani* Kohn; *Fusarium* spp., or Phythium *aphanidermatum* (Eds.) Fitzp.; *Colletotrichum gossypii* South W.; *Fusarium oxysporum* f. sp. *vesinfectum* (Atk.) Snyder et Hansen, *Verticillium dahliae* Kleb.; *Mygnaporthe grasea; Rhizoctonia solani* Kuhn; *Bipolaris oryzae; Sclerotium oryzae; Gibberella fujikuroi; Sclerophthora macrospora* (Saccardo) Thirumalachar, Shaw & *Narasimhan* var. *oryzae* Zhang & Liu; *Ustilaginoidea virens* (Cooke) P. Henn); *Sarocladium oryzae* (Sawada) W. Gams, et Webster; *Xanthomonas oryzae* pv. *oryzae; Xanthomonas oryzae* pv. *oryzicola; Erwinia chrysanthemi* pv. *zeae* (Sabet) Victria, Arboleda et Munoz.; Rice stripe virus, RSV; Rice black streaked dwarf virus, RBSDV; *Helminthosporium sigmoideum* var. Irregulare Crall. EtTull.; *Setosphaeria turcica; Bipolaris maydis* Nisik & Miyake; *Bipolaris carbonum* Wilson; *Physoderma maydis* Miyabe; *Rhizoctonia solani* Kühn; *Puccinia sorghi* Schw.; *Sphacelotheca reiliana* (Kuhn) Clint.; *Fusarium* spp. or *Pythium* spp.; *Ustilago maydis* (DC.) Corda.; *Stenocarpell maydis* (Berk) Sutton, *Macrospora* (Earle) Sutton or *Diplodia frumenti* Ell. et Ev.; Maize rough dwarf virus and *Fusarium moniliforme; Sclerotinia sclerotiorum* (Lib.) de Bary; Rape virus diseases caused by TuMV, CMV, YoMV; *Hyaloperonospora parasitica; Albugo candida* (Pers.) Kuntze; *Phytophthora sojae, Fusarium* spp., *Pythium* spp. or *Rhizoctoni solani; Sclerotinia sclerotiorum* (Lib.) de Bary; *Cercospora sojina*; Soybean mosaic virus, SMV; *Heterodera glycines* Ichinohe; *Heferodera glycines* Inhinohe, *Meloidogyne* spp., *Rotylenchulus reniformis, Belonolaimus gracilis B. longicaudatus*, Hoplolaimus Columbus, Pratylenchus or *Tylenchorhynchus* spp.; *Phakopsora pachyrhizi* Sydow; *Glomerella glycines* (Hori) Lehman et Wolf; *Xanthomonas campestris* pv; *Septoria glycines* Hemmi; *Peronospora manschurica* (Naum.) Syd.; *Pseudomonas solanacearum* (Smith); *Diplodia gossypina* Cooke; *Fusarium* spp.; *Mycosphaerella arachidicola* (Hori) Jenk; *Phoma arachidicola* Marass; *Mesocriconema ornata; Sphaceloma arachidis* Bitaucourtet Jenkins; *Ralstonia solanacearum* Yabuuhi et al; *Pseudomonas syringae* pv. tabacy *Erwinia carotovora* subsp. *carotovora; Pseudomonas angulata; Phytophthora parasitica* var. *nicotianae* (Breda de Hean) Tucker; *Alter aria alternata* (Fries) Keissler; *Cercospora nicotianae* Ell. & Ev.; *Colletotrichum micotianae averna; Thielaviopsis basicola* (Berk. & Br.) Ferr.; *Fusarium oxyporum, F. solani; Pythium* spp.; *Rhizoctonia solani* Kuhn; *Ascochyta gossyph* Syd.; *Erysiphe cichoracearum* DC.; *Sclerotium rolfsii* Sacc; *Sclerotium rolfsii* Sacc.; Tobacco mosaic virus, TMV; Cucumber mosaic virus, CMV; Tobacco etch virus, TEV; *Peronospora parasitica* (Persoon: Fries) Fries; *Erwinia carotovora* subsp. *Carotovora*; Heart disease caused by dried cabbage; Cabbage virus disease caused by TuMV, CMV, TMV; *Alternaria brassicae* (Berk.) Sace.; *Xanthomonas campestris* pv. *campestris; Colletotrichum higginsianum* Sacc.; *Plasmodiophora brassicae* Woron; *Pseudomonas syringae* pv. tomato; *Phytophthora infestans*; Tomato st alk rot; *Leveillula taurica* (Lev.); Arn. *Oidium lycopersici* Cooke et Mass.; *Pythium* spp., *Phytophthora capsici* Leonian; Tomato spotted wilt virus, TSWV; *Pseudomonas syringae* pv. tomato; Tomato yellow leaf curl China virus, TYLCCNV; *Fulvia fulva* (Cooke) Cif; Tomato virus disease caused by TMV, ToMV, CMV; *Phytophthora infestans; Rhizoctonia solani, Phytophthora parasitica* Dast.; Tomato fruit deformation disease; Tomato perforator disease; Tomato black ring nepovirus, TBRV; *Ditylenchus* destructor Thome; *Phytophthora nicotianae* van Breda de Haan; *Colletotrichum atramentarium* (Berkeley et Broome) Taubenhaus; *Colletotrichum atramentarium* (Berkeley et Broome) Taubenhaus; *Rhizopus stolonifera* (Ehrenb.) Lind; Tomato heart rot disease; *Rhizopus stolonifer* (Ehrenb.) Lind; Tomato hypothermia disorder disease; Tomato giant bud disease; Tomato Physiological leaf curling disease; Tomato cataplexy disease; Tomato falling flower and fruit disease; Tomato bud blight disease; *Pectobacterium carotovorum* subsp. *carotovorum; Fusarium solani; Rhizoctonia colani* Kuhn.; Tomato sunburn disease; *Xanthomonas gardnen; Trichothecium roseurn* Link; Tomato dehiscence disease; *Clavibater michiganensis* (Smith) Davis et al., subsp. *michiganensis* (Smith) Davis et al.; Tomato navel rot disease; *Helminthosporium carposaprum; Pseudomonas syringae* pv. tomato (Okabe) Young, Dye & Wilkie; TMV, CMV; Tomato Yellow Leaf Curl Disease, TYLCD; *Phytophthora capsid* or *Phytophthora parasitica; Sclerotinia sclerotiorum* (Lib.) De Bary.; *Ralstonia solanacearum; Phomopsis vexans* (Sacc. Et Syd.) Harter.; *Verticillium dahliae* Kleb.; *Corynespora cassiicola; Alternaria solani* (Ell. et Mart.) Jones et Grout; Eggplant mosaic virus, EMV; *Phyllosticta melongenae* Sawada; Fulviafulva (Cooke) Cif.; *Sphaerotheca fuliginea* (Schlecht) Poll.; *Phyllosticta melongenae* Sawada; *Pseudocercospora deightonii* Minter; *Cercospora solani-melongenae* Chupp or *C. melongenae* Welles; *Corynespora cassiicola* (Berk, et Curt.) Wei.; *Phytophthora infestans* de Bary; *Colletotrichum truncatum* (Schw.) Andrus et Moore; *Rhizopus nigricans* Ehrenb.; *Fusarium* oxysporum f. sp. melongenae Matuo et Ishigami Schlecht.; *Botrytis cinerea* Per.; *Rhizoctonia solani* Kuhn; *Capsicum* mottle virus, CaMV; *Alternaria solani* (Ell. Et Mart.) Jones et Grout; *Stemphylium lycopersici* (Enjoji) Yamamoto; *Phyllosticta* capsid Speg.; *Phaeoramularia capsidcola* (Vassiljevskiy) Deighton; *Fusarium* sp., *Alternaria alternata* or *Penidllium* sp.; *Cladosporium* capsid (March et Stey.) Kovachersky; *Fusarium oxysporum* f. sp. *Vasinfectum* (Atk.) Synder et Hansen; *Sclerotinia sclerotiorum* (Libert) de Bery; Hot pepper sunburn; *Capsicum* mottle virus; *Capsicum* malformed fruit disease; Pepper navel rot disease; *Erwinia carotovora* subsp.; *Xanthomonas campestris* pv. *vesicatoria*; *Capsicum* mottle virus; *Pythium aphanidermatum* (Eds.) Fitzp.; *Drechslera ellisii* Danguah; *Septoria lycopersici* Speg; *Alternaria alternata*; *Verticillium dahliae* Kleb; *Pseudomonas syringae* pv. *aptata* Young. Dye & wilkie; *Choanephora manshurica* (Saito. et Nagamoto) Tai; *Fusarium vasinfectum* Atk.; *Rhizoctonia solani*; *Colletotrichum acutatum*; *Cercospora capsica* HealdetWolf; *Peronospora capsid* Tao et Li sp. nov.; *Botrytis cinerea* Pers or *Sclerotinia fuckeliana* (de Bary) Whetzel; *Stemphylium solani* Weber; *Fulvia fulva* (Cooke) Cif.; *Pythium aphanidermatum*; *Phytophthora capsici* Leonian; *Plasmopara viticola* (Berk, dt Curtis) Berk Et de Toni; *Undnula necator*; *Phaeoisariopsis vitis* (Lev.); Grapevine leafroll Iassociated virus, GLRaVs; Grapevine fan leaf disease, GFLV; *Phakopsora ampelopsidis* Diet, et Syd.; *Acrospermum viticola* IKata; *Septoria ampelina* Berk & Curt; *Cercospora roesle, Cercospora truncata*; *Acrospermun viticola*; *Cristulariella moricola*; Grape new shoot wasting disease; Grape spotted wilt virus, GSWV; Grape wasting disease, GSV; Grape stripe disease; Grapevine flavescence doree virus, GFDV; Grape infection necrosis disease; Grape yellow spot disease; Grapevine enation disease virus, GEDV; Grape veinal necrosis; Grapevine fleck virus, GFkV; Grapecine asteroid mosaic virus, GAMV; *Xyllela fastidiosa*, Wells et al; *Coniothyrium diplodiella* (Speq.) Sacc; *Colletotrichum gloeosporioides* Penz; *Guignardia baccae* (Cav.) Trcz; *Botrytis cinereal* Pers.; *Elsinoe ampelina* (de Bary) Shear; *Guignardia bidwellii*; *Pestalotia uvicola* Speg; *Leptothyrium pomi* Sacc.; *Cladosporium herbarum*; *Leptoth triumpomi*; *Melanoconium fuligineum* (Schr. et viala) Cavara; Grape *cladosporium* rot disease; *Penicillium*; *Alternaria viniferae*; *Valsa mali* Miyabe et Yamada, *Cytospora mandshurica* Miura; *Botryosphaeria berengeriana* (Moug. ex fr) Ces. etdeNot; *Botryospuaeria berengeriana* de Not. t. sp. *piricola* (Nose) Kogonezawa et Sukuma; *Nectria galligena*; *Nummularia discreta* (Schw.) Tub; *Corticium salmonicolor* Berk, et Br.; *Diaporthe eres* Nitschke; *Lasiodiplodia pseudotheobromae*; *Colletotrichum gloeosporioides* (Penz.) Penz. et Sacc.; *Alternaria* alternate, *Trichothecium roseum*; *Gymnosporangium yamadai* Miyabe; *Monilinia mali* (Takab.) Whetzel; *Monilinia fructigena*; *Physalospora obtuse* Schw. Cooke; *Phytophthora cactorum* (Leb. et Cohn.) Schrot.; *Gloeodes pomigina* (Schw) Colby; *Diplocarpon mali* Y. Harada & Sawamura or *Marssonina coronaria* (Ell. & J. J. Davis) J. J. Davis, syn. *Marssonina mali* (Henn) S. Ito) Davis, *Diplocarpon mali* Harada et Sawamura; *Alternaria alternaria* f. sp *mali*; *Alternaria mali* Roberts; *Phyllosticta pirina* Sacc., *Coryneum foliicolum*; *Podosphaera leucotricha* (Eli. et Ev.) Salm; *Fusicladium dendriticum* (wallr.) Fuck.; *Chondrosiereum pur-puteum* (Pers. Fr.) Pougar; *Fusarium solani* (Mart.) App. Et, *Fusarium camptoceras*; Apple *Armillariella* root rot disease; *Armillariella tabescens* (Scop., Fr.) Sing.; *Sclerotium rolfsii* Sacc.; *Heliocobasidium brebissonini*; *Rosellinia necatrix*; *Agrobacterium tumefaciens*; Stem pitting virus, SPV; Apple scar skin viroid, ASSVd; Apaya ring spot virus, PRSV); Apple green crinkle virus, APCV; Apple fruit shrink disease; Apple little leaf disease; Apple yellow leaf disease; Apple bitter rot disease; Apple water heart disease; Apple Superficial Scald disease; Hongyu apple spot disease; Golden delicious rust disease; *Penicillium expansum* (Link) Thom; *Rhizopus oryzae*; Apple sarcocarp pink disease; Apple sarcocarp flesh browning disease; Apple brown heart disease; *Venturia piritna* Aderh or *Venturia nashicola* Tanak et Yamamota or *Fusicladium plrinum* (Lib) Fuck; *Physalospora piricola* Nose, *Macrophoma kuwatsukai* Hara; *Valsa mali Miyabe* et Yamada var. *pyri* Y. J. Lu; *Athelia rolfsii* Tu et Kim.; *Fomes truncatospora* (Lloyd) Teng, *Fomes marginatus* (Eers. ex Fr) Gill, *Phellinus pomacens* (Pers. es Grag) Quel or *Pyropolyporus fomentarius* (L. ex Fr.) Teng; *Bacillus atrophaeus*; *Gymnosporangium asiaticum* Miyabe ex Yamada; *Alternaria kikuchiana* Tanaka; *Phyllosticta pirina* Sacc.; *Mycosphaerella sentina* (Fr.) Schr ter or *Septoria piricola* Desm.; *Gloeodes pomigena* (Schw)Colby; Pear top rot disease; Pear shrink disease; Pear yellow-leaf disease; *Colletotrichum gloeosporioides*; *Phomopsis amygdalina* Canonaco; *Macrophoma kawatsukai* Hara; *Aspergillus aculeatus*; *Phomopsis amygdali*; *Podosphaera tridactyta*, *Sphaerotheca pannosa*; *Monilinia laxa*; *Cladosporium carpophilum*; *Eriophyes catacardiae* Keifer; *Clasdosporium hergbrum*; *Taphrina deformans*; *Clasterosporium carpophilum* and *Pseudocercospora circumscissa*; *Xanthomonas arboricola* pv. *pruni*; Peach leaf spot; *Puccinia* sin for mis; Peach mosaic-associated virus, PMV; *Prunus* necrotic ringspot virus; *Valsa leucostoma*; *Botryosphaeria dothidea*; *Fomes fulvus*, *Trametes hispida* or *Polystictus unicolor*; *Cytospora leucostma* Sace.; *Agrobacterium tumefaciens*; *Fusarium solani* (Mart.) APP. et wollenw.; *Meloidogyne* spp.; *Candidatus Liberibacter* spp.; *Citrus excocortis* virus; *Citrus* tatter leaf virus, CTLV; *Citrus tristeza* virus, CTV; Satsuma dwarf virus, SDV; *Xanthomonas citri* subsp. *citri*; Elsinoefewcettj; *Colletotrichum gloeosporioides* Penz; *Phytophthora parasitica* (Dastur); *Diaporthe medusaea* (Nitsehke); *Phytophthora* sp., *Fusarium* sp., *Diplodia* sp.; *Capnodium citri* (Mont.); *Mycosphaerlla citri*; *Mycosphaerella citri* Whit.; *Mycosphaerella citri* Whit.; *Corticum salmonicolor* Berk.; *Helicobasidium* sp.; *Rhizoctonia solani*; *Phytophthora* spp.; Banana bunchy top virus, BBTV; Heart rot disease of banana leaves and flowers; *Fusariun oxysporun* f. sp. *Cubense*; *Cercsproa musae*; *Mycosphaerella. musicola* J. L. Mulder; *Helminthosporium torulosum* (Syd.) Ashby; *Marcophoma musae* (Cooke) Berk et Vogl; *Pyricularia grise*; *Colletotrchum musae* (Berk. etCurt) v. Arx; *Fusarium semitectum*; *Pseudomonas symngae* pv. *maculicola* (McCulloch) Young; *Sclerotinia sclerotiorum* (Libert) de Bery; *Xanthomonas canpestris* (Panmmel) Dowson; *Alternaria brassicae* (Berk.) Sacc; *Alternaria brassicae* Sacc; Cabbage split ball disease; Cabbage virus disease caused by TuMV, CMV, TMV; *Erwinia carotovora* pv. *carotovora* Dye; Cabbage early bolting; *Hyaloperonospora parasitica*; *Colletotrichum truncatum*; *Phoma lingam* (Tode ex Schw.) Desm.; *Ceratocystis paradoxa* Moreau; *Sporisorium scitamineum* (Syd.); *Clavibacter xyli* subsp *xyli* Davis et al); *Cochliobolus stenospilus* (Drechs) Mats et Yam and *Bipolaris stenospila* (Drechs) Shoemaker; *Puccinia melanocephala* Sydow or *Puccinia kuehnii* Butl.; *Sphaceclootheca cruenta* (Kudhn) Potter; *Mycosphaerella hold* Tehon; *Colletotrichum graminicola* (Cesati) Wilson.; *Setosphaeria turcica* (Luttr.) Leonard & Suggs; Sugarcane mosaic virus, SMV.

The $5_A5_B6_C$ tricyclic spironolactone derivative XI of the present invention is in combination with a commercial antiviral agent to form an antiviral agent mixture for controlling agricultural, forestry and horticultural plant virus diseases.

The $5_A5_B6_C$ tricyclic spironolactone derivative XI of the present invention is in combination with any agriculturally acceptable pesticidal adjuvant agent and any one or more of the following commercially antiviral agents for preparing an antivirus agent mixture and a plant activator mixture.

The commercial antiviral agent was selected from benzothiadiazole, tiadinil, methiadinil, 4-methyl-1,2,3-thiadiazole-5-carboxylic acid, sodium 4-methyl-1,2,3-thiadiazole-5-carboxylate, ethyl 4-methyl-1,2,3-thiadiazole-5-carboxylate, ethyl 4-bromomethyl-1,2,3-thiadiazole-5-carboxylate, ethyl 4-iodomethyl-1,2,3-thiadiazole-5-carboxylate, 4-bromomethyl-5-methyl-1,2,3-thiadiazole, 4-iodomethyl-5-methyl-1,2,3-thiadiazole, ethyl 4,4-dibromomethyl-1,2,3-thiadiazole-5-carboxylate, 3,4-dichloroisothiazole-5-carboxylic acid, sodium 3,4-dichloroisothiazole-5-carboxylate, ethyl 3,4-dichloroisothiazole-5-carboxylic acid, DL-β-aminobutyric acid, virazole, antofine, ningnanmycin, methiadinil, salicylic acid, cytosinpeptidemycin, dichloroisonicotinic acid, probenazole, validoxylamine, or validamycin.

The mass percentage of the $5_A5_B6_C$ tricyclic spironolactone derivative XI of the present invention in the antivirus agent mixture or plant activator mixture was 1%-90%, and the mass ratio of the $5_A5_B6_C$ tricyclic spironolactone derivative XI to the above described commercial antivirus agent was from 1%: 99% to 99%: 1%.

The formulation of the antivirus agent mixture and plant activator mixture was selected from wettable powder, microcapsule suspension, dispersible liquid preparation, dispersible solid preparation, seed treatment emulsion, water emulsion, large granule, microemulsion, oil suspension Agents, pesticide-coated seeds, water-soluble granules, soluble concentrates, water-dispersible granules, poisonous grains, aerosols, block poison bait, slow-release block, concentrated poison bait, capsule granules, dry seed powder, emulsifiable concentrate, electrostatic spray for wettable powder, water-in-oil emulsion, oil-in-water emulsion, aerosol can, fine granules, smoke candle, smoke tube, smoke stick, seed treatment suspension agent, smoke flake, smoke pill, granular poisonous bait, Thermal mist, paint, seed treatment liquid, microparticle, oil-dispersible powder, flake poison, thick glue, pouring agent, spreading agent, suspension emulsion, film-forming oil agent, soluble powder, seed treatment water-soluble powder, ultra-low-capacity suspending agent, tracking powder, ultra-low capacity liquid, or water-dispersible powder for wet dressing.

The plant suitable for the antivirus agent mixture and plant activator mixture was selected from rice, wheat, barley, oats, corn, sorghum, sweet potato, potato, cassava, soybean, pea bean, broad bean, pea, mung bean, adzuki bean, cotton, silkworm, Peanut, rapeseed, sesame, sunflower, beet, sugar cane, coffee, cocoa, ginseng, fritillary, rubber, coconut, oil palm, sisal, tobacco, tomato, pepper, radish, cucumber, cabbage, celery, mustard, shallot, garlic, watermelon, melon, cantaloupe, papaya, apple, citrus, peach tree, tea, wild vegetables, bamboo shoots, hops, pepper, banana, papaya, orchid, or bonsai.

The virus disease controlled by the antivirus agent mixture and the plant activator mixture was rice dwarf disease, yellow dwarf disease, stripe leaf blight, tomato fern leaf virus disease, pepper mosaic virus disease, tobacco vein necrosis virus disease, corn dwarf mosaic vims, cauliflower mosaic vims, citrus virus disease, orchid flower mosaic vims, or orchid ring spot vims.

TABLE 1

Structure and physicochemical parameters of the 5,5,6-tricyclic spirolactone derivatives XI and its intermediates of the present invention

| No | Code | Structure | $^1$H NMR (δ, Solvent: CDCl$_3$); $^{13}$C NMR (100 MHz, CDCl$_3$); HRMS Mp/° C. | Dr value cis/trans | Shape |
|---|---|---|---|---|---|
| 1 | Zyj06-39 | 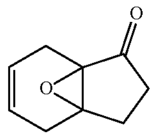 [SMILES: O=C1CCC23CC=CCC12O3] | $^1$H NMR (400 MHZ, CDCl$_3$) δ 5.60-5.46 (m, 2H), 2.87-2.77 (m, 1H), 2.72-2.65 (m, 2H), 2.48-2.39 (m, 1H), 2.16-2.08 (m, 1H). $^{13}$C NMR (101 MHz, CDCl$_3$) δ 211.25, 121.14, 121.02, 66.67, 62.59, 31.75, 28.48, 26.91, 20.82. | | Yellow liquid |
| 2 | Zyj06-43 | 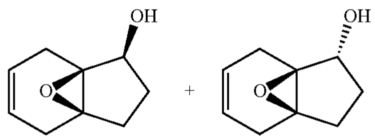 [SMILES: O[C@H]1CC[C@]23CC=CC[C@]12O3 ; O[C@@H]1CC[C@]23CC=CC[C@]12O3] | 119-120 $^1$H NMR (400 MHZ, CDCl$_3$) δ 5.55 (d, J = 10.4 Hz, 1H), 5.49 (d, J = 11.0 Hz, 1H), 4.15 (q, J = 7.8 Hz, 1H), 2.74 (d, J = 19.2 Hz, 1H), 2.61 (d, J = 19.1 Hz, 1H), 2.46 (d, J = 19.4 Hz, 1H), 2.35 (d, J = 19.2 Hz, 1H), 2.23-2.07 (m, 2H), 2.02-1.97 (m, 1H), 1.62-1.54 (m, 1H). $^{13}$C NMR (101 MHz, CDCl$_3$) δ 121.73, 76.58, 66.20, 64.81, 29.16, 28.70, 28.16, 25.49. HRMS (ESI-TOF) m/z calcd for C$_9$H$_{13}$O$_2$ [M + H $^+$] 153.0916, found 153.0910. | 8:1 | White solid |
| 3 | Zyj06-72 | 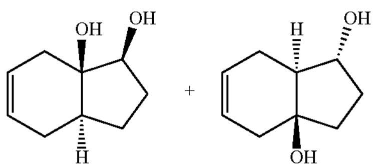 [SMILES: O[C@H]1CC[C@H]2CC=CC[C@@]21O ; O[C@@H]1CC[C@]2(O)CC=CC[C@@H]12] | 46-48 $^1$H NMR (400 MHZ, CDCl$_3$) δ 5.69-5.54 (m, 1H), 3.99 (d, J = 6.6 Hz, 1H), 3.62 (br, 1H), 2.48-2.18 (m, 4H), 2.0-1.96 (m, 1H), 1.90-1.72 (m, 3H), 1.60-1.48 (m, 1H). $^{13}$C NMR (101 MHz, CDCl$_3$) δ 124.64, 124.31, 79.95, 78.77, 49.83, 36.29, 35.20, 31.91, 26.80. HRMS (ESI-TOF) m/z calcd for C$_9$H$_{14}$NaO$_2$ [M + Na $^+$] 177.0891, found 177.0884. | | White powder |
| 4 | Zyj06-80 | 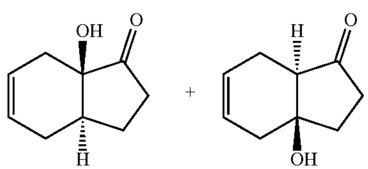 [SMILES: O=C1CC[C@H]2CC=CC[C@]12O ; O=C1CC[C@]2(O)CC=CC[C@@H]12] | $^1$H NMR (400 MHZ, CDCl$_3$) δ 5.82-5.76 (m, 1H), 5.70-5.61 (m, 1H), 2.68 (br, 1H), 2.61-2.45 (m, 1H), 2.29-2.19 (m, 3H), 2.18-2.06 (m, 1H), 2.03-1.74 (m, 3H). $^{13}$C NMR (101 MHz, CDCl$_3$) δ 216.87,127.00, 123.34, 73.82, 41.32, 35.20, 32.28, 26.65, 24.29. | | Yellow liquid |
| 5 | Zyj06-82 | 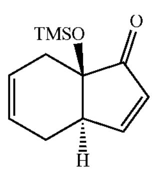 | $^1$H NMR (400 MHZ, CDCl$_3$) δ 7.35 (d, J = 5.4 Hz, 1H), 6.05 (dd, J = 6.0, 2.9 Hz, 1H), 5.73-5.70 (m, 1H), 5.61-5.59 (m, 1H), 2.62-2.59 (m, 1H), 2.42-2.12 (m, 4H), 0.00 (s, 9H). $^{13}$C NMR (101 MHz, CDCl$_3$) δ 205.25, 159.59, 130.29, 126.23, 123.52, 76.12, 46.72, 30.13, 23.46. HRMS (ESI-TOF) m/z calcd for C$_{12}$H$_{19}$O$_2$Si [M + H $^+$] 223.1154, found 223.1147. | | Yellow liquid |

TABLE 1-continued

Structure and physicochemical parameters of the 5,5,6C tricyclic spirolactone derivatives XI and its intermediates of the present invention

| No | Code | Structure | $^1$H NMR (δ, Solvent: CDCl$_3$); $^{13}$C NMR (100 MHz, CDCl$_3$); HRMS Mp/° C. | Dr value cis/trans | Shape |
|---|---|---|---|---|---|
| 6 | Zyj06-162 | (structure) | $^1$H NMR (400 MHZ, CDCl$_3$) δ 5.82-5.57 (m, 2H), 5.56-5.37 (m, 1H), 5.02-4.85 (m, 2H), 4.77 (d, J = 3.0 Hz, 1H), 2.44-1.96 (m, 6H), 1.88-1.76 (m, 2H), 0.17 (s, 9H), 0.00 (m, 9H). $^{13}$C NMR (101 MHz, CDCl$_3$) δ 158.54, 138.93, 128.59, 124.32, 114.76, 108.74, 79.95, 46.92, 42.55, 36.35, 36.13, 24.34, 1.98, −0.00. | | Yellow liquid |
| 7 | Zyj06-161 | (structure) | $^1$H NMR (400 MHz, CDCl$_3$) δ 5.85-5.79 (m, 1H), 5.72-5.66 (m, 1H), 4.87 (s, 2H), 2.97-2.88 (m, 1H), 2.72 (dd, J = 19.3, 8.1 Hz, 1H), 2.35-2.24 (m, 3H), 2.22-2.04 (m, 2H), 1.93 (s, 1H), 1.84-1.71 (m, 5H). $^{13}$C NMR (101 MHz, CDCl$_3$) δ 212.89, 143.05, 125.67, 121.80, 110.10, 44.97, 43.31, 39.38, 30.52, 23.76, 18.33. HRMS (ESI-TOF) m/z calcd for C$_{17}$H$_{23}$O$_5$ [M + H $^+$] 307.1545, found 307.1537. | 15:1 | Yellow liquid |
| 8 | Zyj06-177 | (structure) | $^1$H NMR (400 MHz, CDCl$_3$) δ 5.84-5.78 (m, 1H), 5.77-5.68 (m, 1H), 5.64-5.58 (m, 1H), 5.05-4.99 (m, 2H), 2.55-2.24 (m, 8H), 2.20-2.01 (m, 4H). $^{13}$C NMR (101 MHz, CDCl$_3$) δ 217.62, 137.85, 127.48, 123.19, 116.07, 74.26, 43.57, 41.05, 35.48, 35.03, 33.95, 23.52. HRMS (ESI-TOF) m/z calcd for C$_{12}$H$_{16}$NaO$_2$ [M + Na $^+$] 215.1048, found 215.1039. | >20:1 | Yellow liquid |
| 9 | Zyj06-92-2 | (structure) | $^1$H NMR (400 MHz, CDCl$_3$) δ 5.80-5.77 (m, 1H), 5.64-5.58 (m, 1H), 4.72-4.66 (m, 1H), 2.99 (dd, J = 19.5, 7.7 Hz, 1H), 2.61-2.51 (m, 1H), 2.43-2.13 (m, 4H), 1.88-1.80 (m, 1H), 1.22 (s, 9H). $^{13}$C NMR (101 MHz, CDCl$_3$) δ 210.33, 125.94, 121.81, 81.39, 79.46, 75.52, 44.62, 40.38, 31.41, 25.34, 24.42. HRMS (ESI-TOF) m/z calcd for C$_{13}$H$_{24}$NO$_4$ [M + NH$_4$ $^+$] 258.1705, found 258.1699. | >20:1 | Yellow liquid |
| 10 | Zyj06-111-2 | (structure) | $^1$H NMR (400 MHz, CDCl$_3$) δ 5.83-5.75 (m, 1H), 5.67-5.59 (m, 1H), 4.08-3.96 (m, 1H), 3.38 (s, 3H), 3.00 (dd, J = 19.1, 7.4 Hz, 1H), 2.56-2.46 (m, 1H), 2.35-2.25 (m, 2H), 2.20-2.03 (m, 2H), 1.84-1.74 (m, 1H). $^{13}$C NMR (101 MHz, CDCl$_3$) δ 211.63, 126.86, 122.91, 80.25, 76.31, 58.05, 47.29, 42.15, 32.49, 24.94. HRMS (ESI-TOF) m/z calcd for C$_{10}$H$_{15}$O$_3$ [M + H $^+$] 183.1021, found 183.1015. | 8:1 | Yellow liquid |

TABLE 1-continued

Structure and physicochemical parameters of the 5₅5₆6_C tricyclic spirolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 11 | Zyj06-113-2 | (structure) | ¹H NMR (400 MHZ, CDCl₃) δ 5.75-5.65 (m, 1H), 5.61-5.53 (m, 1H), 4.27-4.09 (m, 4H), 3.41 (d, J = 6.7 Hz, 1H), 2.96-2.73 (m, 2H), 2.26-2.12 (m, 6H), 1.29-1.17 (m, 6H). ¹³C NMR (101 MHz, CDCl₃) δ 213.56, 168.54, 168.06, 126.53, 123.15, 74.80, 61.69, 61.58, 53.55, 44.59, 39.35, 37.21, 32.49, 26.29, 25.01, 14.09, 14.05. HRMS (ESI-TOF) m/z calcd for C₁₆H₂₃O₆ [M + H⁺] 311.1495, found 311.1488. | >20:1 | Yellow liquid |
| 12 | Zyj06-166 | (structure) | ¹H NMR (400 MHZ, CDCl₃) δ 5.85-5.78 (m, 1H), 5.72-5.64 (m, 1H), 4.87 (s, 2H), 2.98-2.88 (m, 1H), 2.72 (dd, J = 19.3, 8.1 Hz, 1H), 2.35-2.24 (m, 3H), 2.21-2.05 (m, 2H), 1.83-1.75 (m, 1H), 1.73 (d, J = 3.7 Hz, 3H). ¹³C NMR (101 MHz, CDCl₃) δ 214.74, 144.04, 127.15, 123.16, 111.76, 75.20, 44.89, 44.59, 41.19, 32.94, 25.03, 19.66. | >20:1 | Yellow liquid |
| 13 | Zyj07-95 | (structure) | ¹H NMR (400 MHZ, CDCl₃) δ 5.80-5.72 (m, 1H), 5.70-5.62 (m, 1H), 4.35-4.24 (m, 2H), 3.89 (d, J = 0.7 Hz, 1H), 2.70-2.56 (m, 1H), 2.51-2.37 (m, 1H), 2.29 (d, J = 16.5 Hz, 1H), 2.18-1.88 (m, 6H), 1.33 (t, J = 7.0 Hz, 3H). ¹³C NMR (101 MHZ, CDCl₃) δ 169.16, 167.28, 126.36, 123.02, 95.36, 82.84, 62.78, 58.37, 41.44, 30.91, 27.60, 13.99. HRMS (ESI-TOF) m/z calcd for C₁₄H₁₉O₅ [M + H⁺] 267.1232, found 267.1231. | 114-115 | White solid |
| 14 | Zyj06-180 | (structure) | ¹H NMR (400 MHZ, CDCl₃) δ 5.80-5.75 (m, 1H), 5.67-5.51 (m, 2H), 5.09-4.86 (m, 2H), 4.33-4.19 (m, 2H), 3.72 (d, J = 73.8 Hz, 1H), 2.69-2.57 (m, 1H), 2.43-1.90 (m, 8H), 1.88-1.65 (m, 1H), 1.28 (t, J = 7.1 Hz, 6H). ¹³C NMR (101 MHz, CDCl₃) δ 168.77, 167.98, 167.24, 166.63, 137.28, 137.26, 126.94, 126.59, 122.92, 122.56, 116.49, 116.38, 96.44, 94.40, 84.42, 83.24, 62.81, 61.99, 58.33, 56.51, 47.22, 43.57, 42.46, 42.19, 37.53, 37.38, 35.95, 35.45, 32.06, 30.93, 24.65, 24.34, 14.16, 13.98. HRMS (ESI-TOF) m/z calcd for C₁₇H₂₃O₅ [M + H⁺] 307.1545, found 307.1540. | | Light yellow liquid |

TABLE 1-continued

Structure and physicochemical parameters of the 5,5,6, tricyclic spirolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 15 | Zyj06-127 | [structure] | ¹H NMR (400 MHz, CDCl₃) δ 5.76-5.66 (m, 1H), 5.61-5.55 (m, 1H), 4.29-4.13 (m, 3H), 3.61 (s, 1H), 2.71-2.56 (m, 1H), 2.51-2.40 (m, 2H), 2.27-1.87 (m, 4H), 1.27 (dt, J = 13.5, 6.8 Hz, 3H), 1.15 (s, 9H). ¹³C NMR (101 MHz, CDCl₃) δ 168.04, 167.13, 126.17, 122.64, 94.14, 84.44, 80.74, 80.58, 63.00, 57.61, 47.06, 44.50, 31.06, 26.78, 26.31, 13.98. HRMS (ESI-TOF) m/z calcd for $C_{18}H_{25}O_7$ [M − H⁻] 353.1606, found 353.1602. | | White liquid |
| 16 | Zyj06-187 | [structure] | ¹H NMR (400 MHz, CDCl₃) δ 5.78-5.68 (m, 1H), 5.62-5.55 (m, 1H), 4.27-4.06 (m, 3H), 3.57-3.44 (m, 1H), 3.29 (d, 3H), 2.69-2.54 (m, 1H), 2.51-2.35 (m, 2H), 2.31-1.95 (m, 4H), 1.27 (q, J = 7.1 Hz, 3H). ¹³C NMR (101 MHz, CDCl₃) δ 168.46, 166.91, 125.92, 122.90, 94.03, 82.19, 80.51, 62.84, 58.10, 55.93, 48.06, 45.84, 30.96, 26.36, 13.95. HRMS (ESI-TOF) m/z calcd for $C_{15}H_{21}O_6$ [M + H⁺] 297.1338, found 297.1327. | 19:1 | Light yellow liquid |
| 17 | Zyj06-113-3 | [structure] | 132-134 ¹H NMR (400 MHz, CDCl₃) δ 5.62-5.72 (m, 1H), 5.60-5.55 (m, 1H), 4.26-4.07 (m, 6H), 3.75 (d, J = 74.9 Hz, 1H), 3.39 (dd, J = 40.2, 6.1 Hz, 1H), 2.80-2.51 (m, 1H), 2.41-2.27 (m, 2H), 2.18-1.96 (m, 4H), 1.91-1.83 (m, 1H), 1.28-1.16 (m, 9H). ¹³C NMR (101 MHz, CDCl₃) δ 168.76, 168.68, 168.56, 168.22, 167.94, 167.00, 166.46, 94.95, 93.63, 83.50, 81.44, 62.73, 61.95, 61.78, 61.76, 61.66, 61.64, 58.23, 55.48, 53.64, 53.02, 46.34, 44.23, 42.76, 40.05, 39.60, 39.08, 31.05, 30.27, 26.68, 26.48, 14.15, 14.10, 14.05, 14.00, 13.95. HRMS (ESI-TOF) m/z calcd for $C_{21}H_{32}NO_9$ [M + NH₄⁺] 442.2077, found 442.2080. | 15:1 | White solid |

TABLE 1-continued

Structure and physicochemical parameters of the 5₅5ᵦ6_C tricyclic spironolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 18 | Zyj06-167 | 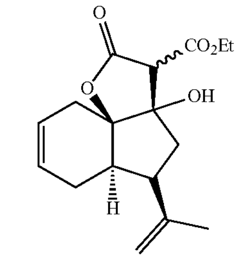 | $^1$H NMR (400 MHZ, CDCl$_3$) δ 5.85-5.75 (m, 1H), 5.71-5.65 (m, 1H), 4.83 (d, J = 8.0 Hz, 2H), 4.36-4.27 (m, 2H), 3.90 (d, J = 139.3 Hz, 1H), 2.88-2.53 (m, 2H), 2.46-2.28 (m, 2H), 2.25-2.15 (m, 2H), 2.09-1.93 (m, 3H), 1.71 (s, 3H). $^{13}$C NMR (101 MHz, CDCl$_3$) δ 167.37, 143.09, 126.32, 122.92, 112.35, 95.35, 81.83, 62.92, 58.07, 47.90, 44.12, 31.21, 26.41, 19.22, 13.98. HRMS (ESI-TOF) m/z calcd for C$_{17}$H$_{23}$O$_5$ [M + H $^+$] 307.1545, found 307.1539. | | Light yellow liquid |
| 19 | Zyj07-96 | 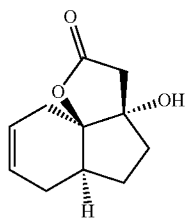 [SMILES: O=C1C[C@@]2(O)CC[C@H]3CC=CC[C@@]32O1] | 139-141 $^1$H NMR (400 MHZ, CDCl$_3$) δ 5.78-5.69 (m, 1H), 5.68-5.64 (m, 1H), 3.28 (s, 1H), 2.94 (d, J = 17.6 Hz, 1H), 2.75 (d, J= 17.6 Hz, 1H), 2.58 (d, J=18.0 Hz, 1H), 2.32-2.03 (m,4H), 2.00-1.86 (m, 3H). $^{13}$C NMR (101 MHz, CDCl$_3$) δ 174.76, 126.60, 123.02, 95.17, 81.79, 43.50, 41.82, 41.20, 30.65, 27.91, 27.60. HRMS (ESI-TOF) m/z calcd for C$_{11}$H$_{15}$O$_3$ [M + H $^+$] 195.1021, found 195.1013. | | White solid |
| 20 | Zyj06-186 | 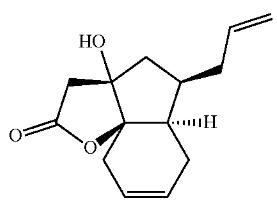 [SMILES: C=CC[C@@H]1C[C@]2(O)CC(=O)O[C@@]23CC=CC[C@H]13] | $^1$H NMR (400 MHZ, CDCl$_3$) δ 5.86-5.77 (m, 1H), 5.72-5.59 (m, 1H), 5.01-4.96 (m, 2H), 3.09 (br, 1H), 2.90 (d, J = 17.3 Hz, 1H), 2.76 (d, J = 17.4 Hz, 1H), 2.63 (d, J = 17.9 Hz, 1H), 2.39-2.11 (m, 6H), 2.10-1.95 (m, 2H), 1.87-1.70 (m, 1H). $^{13}$C NMR (101 MHz, CDCl$_3$) δ 174.34, 137.45, 126.91, 122.97, 116.26, 96.23, 82.17, 46.66, 44.01, 43.31, 37.81, 35.49, 31.63, 24.65. HRMS (ESI-TOF) m/z calcd for C$_{14}$H$_{19}$O$_3$ [M + H $^+$] 235.1334, found 235.1331. | | Light yellow liquid |
| 21 | Zyj06-189 | 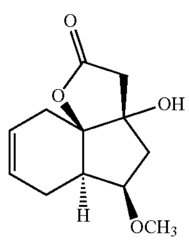 [SMILES: CO[C@@H]1C[C@]2(O)CC(=O)O[C@@]23CC=CC[C@H]13] | $^1$H NMR (400 MHz, CDCl$_3$) δ 5.81-5.76 (m, 1H), 5.69-5.65 (m, 1H), 3.60-3.54 (m, 1H), 3.36 (s, 3H), 2.90 (dd, J = 17.4, 1.9 Hz, 1H), 2.75 (d, J = 17.4 Hz, 1H), 2.68-2.56 (m, 2H), 2.49-2.42 (m, 1H), 2.29-2.00 (m, 3H), 1.93-1.87 (m, 1H). $^{13}$C NMR (101 MHz, CDCl$_3$) δ 173.41, 126.33, 122.80, 93.52, 82.97, 79.62, 58.16, 47.60, 45.76, 43.33, 30.47, 26.45. HRMS (ESI-TOF) m/z calcd for C$_{12}$H$_{17}$O$_4$ [M + H $^+$] 225.1127, found 225.1119. | >20:1 | Yellow liquid |

TABLE 1-continued

Structure and physicochemical parameters of the 5,5,6c tricyclic spirinolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 22 | Zyj06-128 | 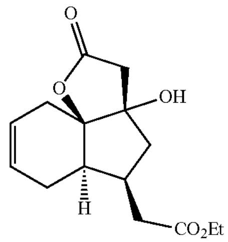 [SMILES: CCOC(=O)C[C@@H]1C[C@]2(O)CC(=O)O[C@@]23CC=CC[C@H]13] | $^1$H NMR (400 MHZ, CDCl$_3$) δ 5.80-5.71 (m, 1H), 5.70-5.62 (m, 1H), 4.12 (q, J = 7.1 Hz, 2H), 2.93 (dd, J = 17.6, 1.7 Hz, 1H), 2.77 (d, J = 17.6 Hz, 1H), 2.56 (ddd, J = 30.6, 16.8, 3.3 Hz, 2H), 2.41 (dd, J = 14.1, 7.7 Hz, 1H), 2.22 (dt, J = 26.3, 13.8 Hz, 3H), 2.15-2.00 (m, 2H), 1.77-1.67 (m, 2H), 1.26 (t, J = 7.1 Hz, 3H). $^{13}$C NMR (101 MHz, CDCl$_3$) δ 174.08, 172.67, 126.18, 123.27, 94.87, 80.98, 60.74, 48.17, 45.64, 43.25, 37.26, 30.79, 26.24, 14.20. HRMS (ESI-TOF) m/z calcd for C$_{15}$H$_{24}$NO$_5$ [M + NH$_4$ $^+$] 298.1654, found 298.1649 | >20:1 | Yellow liquid |
| 23 | Zyj06-175 | 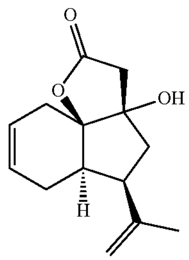 [SMILES: C=C(C)[C@@H]1C[C@]2(O)CC(=O)O[C@@]23CC=CC[C@H]13] | $^1$H NMR (400 MHZ, CDCl$_3$) δ 5.75-5.72 (m,, 1H), 5.66-5.63 (m, 1H), 4.79-4.73 (m, 2H), 2.95 (dd, J = 17.8, 2.0 Hz, 1H), 2.75 (d, J = 17.7 Hz, 1H), 2.61 (dd, J = 18.0, 1.9 Hz, 1H), 2.32-2.13 (m, 3H), 2.04-1.82 (m, 4H). $^{13}$C NMR (101 MHz, CDCl$_3$) δ 174.71, 143.57, 126.61, 123.07, 111.85, 95.40, 80.73, 48.27, 43.91, 43.58, 31.00, 26.41, 19.39, 14.13. HRMS (ESI-TOF) m/z calcd for C$_{14}$H$_{22}$NO$_3$ [M + H $^+$] 252.1600, found 252.1597. | >20:1 | Yellow liquid |
| 24 | Zyj07-29 | 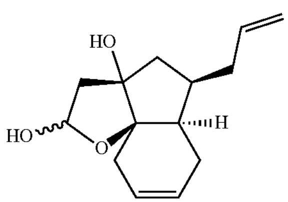 | $^1$H NMR (400 MHZ, CDCl$_3$) δ 5.76-5.73 (m, 1H), 5.69-5.57 (m, 2H), 5.40-5.30 (m, 1H), 5.02-4.85 (m, 2H), 2.51 (dd, J = 13.5, 5.8 Hz, 1H), 2.38-2.30 (m, 1H), 2.29-2.12 (m, 4H), 2.10-1.87 (m, 5H), 1.83-1.79 (m, 1H). $^{13}$C NMR (101 MHz, CDCl$_3$) δ 138.44, 127.18, 124.75, 115.48, 96.81, 90.91, 85.78, 48.16, 46.30, 44.05, 38.02, 36.00, 33.37, 24.99. HRMS (ESI-TOF) m/z calcd for C$_{14}$H$_{20}$NaO$_3$ [M + Na $^+$] 259.1310, found 259.1308. | 4.3:1 | Yellow liquid |
| 25 | Zyj07-37-1 | 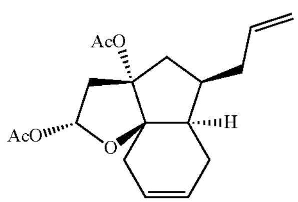 [SMILES: C=CC[C@@H]1C[C@]2(OC(C)=O)C[C@@H](OC(C)=O)O[C@@]23CC=CC[C@H]13] | $^1$H NMR (400 MHZ, CDCl$_3$) δ 5.79-5.58 (m, 3H), 5.27 (dd, J = 6.2, 3.4 Hz, 1H), 5.04-4.87 (m, 2H), 2.99-2.94 (m, 1H), 2.45-1.97 (m, 17H). $^{13}$C NMR (101 MHz, CDCl$_3$) δ 170.24, 138.41, 126.89, 124.38, 115.47, 99.11, 91.69, 91.12, 45.94, 44.82, 44.22, 38.77, 35.88, 32.93, 24.89, 21.61. HRMS (ESI-TOF) m/z calcd for C$_{18}$H$_{24}$NaO$_5$ [M + Na $^+$] 343.1521, found 343.1519. | | White liquid |

TABLE 1-continued

Structure and physicochemical parameters of the 5,5,6c tricyclic spirolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 26 | Zyj07-37-2 | (structure) | ¹H NMR (400 MHZ, CDCl₃) δ 6.22 (dd, J = 6.3, 3.6 Hz, 1H), 5.80-5.75 (m, 1H), 5.71-5.59 (m, 2H), 4.98-4.94 (m, 2H), 3.19 (dd, J = 14.8, 6.3 Hz, 1H), 2.57-2.46 (m, 1H), 2.40-1.94 (m, 17H). ¹³C NMR (101 MHz, CDCl₃) δ 170.00, 138.03, 127.05, 123.98, 115.79, 97.72, 93.52, 90.51, 45.84, 44.64, 44.16, 38.67, 35.75, 32.75, 24.68, 21.51, 21.43. HRMS (ESI-TOF) m/z calcd for C₁₈H₂₄NaO₅ [M + Na ⁺] 343.1521, found 343.1516. | | Light yellow liquid |
| 27 | Zyj07-38 | (structure) | ¹H NMR (400 MHZ, CDCl₃) δ 5.84-5.59 (m, 4H), 5.06-4.95 (m, 4H), 4.11-3.88 (m, 1H), 2.85 (dd, J = 12.3, 5.9 Hz, 1H), 2.51-2.41 (m, 2H), 2.37-2.17 (m, 5H), 2.15-1.80 (m, 8H), 1.84-1.69 (m, 1H). ¹³C NMR (101 MHz, CDCl₃) δ 170.21, 138.54, 134.05, 126.89, 124.30, 117.42, 115.53, 91.76, 90.26, 75.71, 43.39, 42.54, 41.35, 41.52, 36.25, 34.11, 24.86, 21.73. HRMS (ESI-TOF) m/z calcd for C₁₉H₂₇O₃ [M + H ⁺] 303.1960, found 303.1951. | | Light yellow liquid |
| 28 | Zyj07-98 | (structure) | ¹H NMR (400 MHZ, CDCl₃) δ 5.79-5.57 (m, 4H), 5.05-4.93 (m, 4H), 3.91-3.81 (m, 1H), 2.46-2.38 (m, 1H), 2.34-2.17 (m, 5H), 2.14-1.85 (m, 7H), 1.81-1.73 (m, 1H). ¹³C NMR (101 MHz, CDCl₃) δ 138.82, 134.28, 127.05, 124.36, 115.34, 89.15, 86.27, 74.66, 45.42, 43.73, 43.15, 41.54, 37.60, 36.52, 33.62, 24.95. HRMS (ESI-TOF) m/z calcd for C₁₇H₂₅O₂ [M + H ⁺] 261.1855, found 261.1846. | | Light yellow liquid |
| 29 | Zyj07-30 | (structure) | ¹H NMR (400 MHZ, CDCl₃) δ 5.81-5.62 (m, 3H), 5.01-4.91 (m, 2H), 3.91 (td, J = 9.0, 3.7 Hz, 1H), 3.76 (dd, J = 16.3, 8.7 Hz, 1H), 2.31-2.20 (m, 4H), 2.16-1.93 (m, 7H), 1.86-1.81 (m, 1H). ¹³C NMR (101 MHz, CDCl₃) δ 138.77, 127.30, 124.49, 115.31, 89.13, 86.40, 63.49, 45.76, 43.04, 39.23, 37.72, 36.50, 31.06, 25.01. HRMS (ESI-TOF) m/z calcd for C₁₄H₂₁O₂ [M + H ⁺] 221.1542, found 221.1541. | | White liquid |

TABLE 1-continued

Structure and physicochemical parameters of the 5₅5₆6₆ tricyclic spironolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 30 | Zyj07-102 | 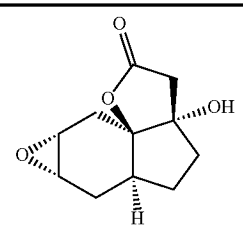 | 119-120 ¹H NMR (400 MHz, CDCl₃) δ 3.35-3.27 (m, 1H), 2.90 (dd, J = 17.8, 2.0 Hz, 1H), 2.73 (d, J = 17.8 Hz, 1H), 2.37-2.23 (m, 1H), 2.20-2.08 (m, 1H), 2.03-1.73 (m, 2H), 1.43-1.23 (m, 1H). ¹³C NMR (101 MHz, CDCl₃) δ 174.07, 93.58, 81.47, 54.20, 50.52, 43.41, 42.38, 37.53, 29.44, 27.30, 25.50. HRMS (ESI-TOF) m/z calcd for C₁₁H₁₄NaO₄ [M + Na⁺] 233.0790, found 233.0783. | | White solid |
| 31 | Zyj07-13 | 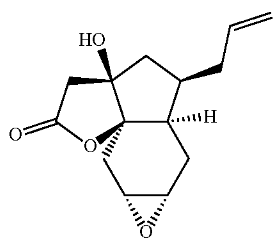 [SMILES: C=CC[C@@H]1C[C@]2(O)CC(=O)O[C@@]23C[C@H]2O[C@H]2C[C@H]13] | ¹H NMR (400 MHz, CDCl₃) δ 5.66-5.58 (m, 1H), 5.04-4.96 (m, 2H), 3.41-3.35 (m, 1H), 3.28 (dd, J = 5.1, 3.9 Hz, 1H), 2.85 (dd, J = 17.6, 1.3 Hz, 1H), 2.77 (s, 1H), 2.39 (d, J = 16.0 Hz, 1H), 2.31-2.20 (m, 3H), 2.19-2.11 (m, 2H), 2.09-1.99 (m, 2H), 1.83-1.72 (m, 1H). ¹³C NMR (101 MHz, CDCl₃) δ 173.28, 137.11, 116.51, 95.71, 82.32, 52.69, 51.53, 46.95, 43.42, 42.77, 37.22, 35.22, 29.84, 22.97 | | |
| 32 | Zyj07-64 | 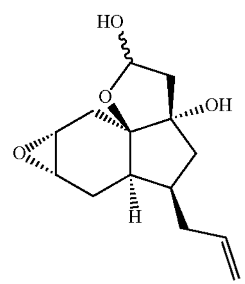 | ¹H NMR (400 MHz, CDCl₃) δ 5.68-5.55 (m, 1H), 5.36-5.34 (m, 1H), 4.95-4.90 (m, 2H), 3.32 (d, J = 2.5 Hz, 1H), 3.24-3.21 (m, 1H), 2.48 (dd, J = 13.6, 5.8 Hz, 1H), 2.25 (dd, J = 15.4, 5.3 Hz, 1H), 2.19-2.12 (m, 2H), 2.11-1.85 (m, 7H), 1.83-1.76 (m, 1H). ¹³C NMR (101 MHz, CDCl₃) δ 138.13, 115.68, 96.86, 89.83, 85.21, 54.81, 51.19, 48.01, 46.76, 39.58, 37.45, 36.18, 31.69, 23.04. HRMS (ESI-TOF) m/z calcd for C₁₄H₂₁O₄ [M + H⁺] 253.1440, found 253.1431. | | Light yellow liquid |

TABLE 1-continued

Structure and physicochemical parameters of the 5₅5₅6_C tricyclic spironolactone derivatives XI and its intermediates of the present invention

| No | Code | Structure | $^1$H NMR (δ, Solvent: CDCl$_3$); $^{13}$C NMR (100 MHz, CDCl$_3$); HRMS Mp/° C. | Dr value cis/trans | Shape |
|---|---|---|---|---|---|
| 33 | Zyj07-65-1 | (structure) | 110-112 $^1$H NMR (400 MHZ, CDCl$_3$) δ 6.20-6.17 (m, 1H), 5.65-5.52 (m, 1H), 4.97-4.89 (m, 2H), 3.32-3.27 (m, 1H), 3.18-3.15 (m, 1H), 3.11-3.05 (m, 1H), 2.24-2.14 (m, 4H), 2.12-1.98 (m, 12H), 1.95-1.87 (m, 1H). $^{13}$C NMR (101 MHz, CDCl$_3$) δ 169.99, 169.89, 137.71, 115.97, 97.33, 92.49, 89.96, 54.61, 50.61, 45.67, 45.01, 39.85, 38.19, 35.75, 31.31, 22.83, 21.42. HRMS (ESI-TOF) m/z calcd for C$_{14}$H$_{21}$O$_4$ [M + H $^+$] 253.1440, found 253.1431. | | White powder |
| 34 | Zyj07-65-2 | (structure) | $^1$H NMR (400 MHZ, CDCl$_3$) δ 6.23 (d, J = 6.2 Hz, 1H), 5.74-5.58 (m, 1H), 5.00-4.91 (m, 2H), 3.34-3.30 (m, 1H), 3.18 (dd, J = 5.1, 3.9 Hz, 1H), 2.92-2.86 (m, 1H), 2.35-2.27 (m, 3H), 2.23-2.13 (m, 5H), 2.07-1.97 (m, 8H), 1.84-1.75 (m, 1H). $^{13}$C NMR (101 MHz, CDCl$_3$) δ 169.94, 169.82, 138.09, 115.58, 96.49, 93.12, 89.02, 54.74, 50.45, 43.17, 43.07, 38.83, 37.56, 36.04, 30.66, 22.92, 21.49, 21.20. | | Light yellow liquid |
| 35 | Zyj07-67-1 | (structure) | $^1$H NMR (400 MHZ, CDCl$_3$) δ 5.80-5.61 (m, 2H), 5.12-5.05 (m, 2H), 5.02-4.94 (m, 2H), 4.00-3.92 (m, 1H), 3.40-3.34 (m, 1H), 3.23-3.21 (m, 1H), 2.84 (dd, J = 12.4, 5.9 Hz, 1H), 2.47-2.39 (m, 1H), 2.35-2.18 (m, 4H), 2.15-1.92 (m, 9H), 1.83 (dd, J = 15.4, 5.4 Hz, 1H), 1.71 (dd, J = 14.6, 8.0 Hz, 1H). $^{13}$C NMR (101 MHz, CDCl$_3$) δ 170.14, 138.19, 133.94, 117.58, 115.74, 91.09, 89.24, 75.85, 54.88, 50.77, 42.86, 41.54, 41.48, 39.20, 37.53, 32.51. HRMS (ESI-TOF) m/z calcd for C$_{19}$H$_{27}$O$_4$ [M + H $^+$] 319.1909, found 319.1989. | | Light yellow liquid |

TABLE 1-continued

Structure and physicochemical parameters of the $5,5,6_C$ tricyclic spironolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 36 | Zyj07-67-2 | 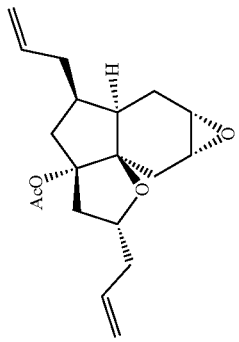 | 100-102 $^1$H NMR (400 MHZ, CDCl$_3$) δ 5.84-5.58 (m, 2H), 5.11-5.05 (m, 2H), 4.99-4.96 (m, 2H), 4.01-3.92 (m, 1H), 3.29-3.22 (m, 2H), 2.80 (dd, J = 12.3, 5.9 Hz, 1H), 2.53-2.46 (m, 1H), 2.37-2.29 (m, 2H), 2.22-1.92 (m, 12H), 1.73-1.66 (m, 1H). $^{13}$C NMR (101 MHZ, CDCl$_3$) δ 169.93, 138.14, 133.94, 117.69, 115.77, 91.75, 90.58, 76.26, 53.34, 51.37, 42.83, 42.69, 41.20, 40.70, 37.53, 35.84, 31.69, 23.08, 21.73. HRMS (ESI-TOF) m/z calcd for C$_{19}$H$_{27}$O$_4$ [M + H $^+$] 319.1909, found 319.1900. | | White solid |
| 37 | Zyj07-31-1 | 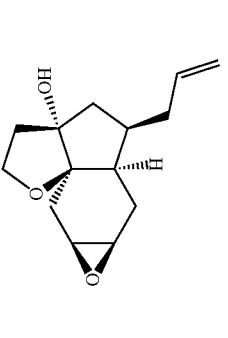 | $^1$H NMR (400 MHZ, CDCl$_3$) δ 5.73-5.60 (m, 1H), 5.01-4.91 (m, 2H), 3.89-3.83 (m, 1H), 3.77-3.71 (m, 1H), 3.36-3.28 (m, 1H), 3.23-3.15 (m, 1H), 2.24-2.16 (m, 1H), 2.14-1.91 (m,9H), 1.88-1.80 (m, 2H). $^{13}$C NMR (101 MHz, CDCl$_3$) δ 138.44, 115.49, 88.32, 85.95, 63.38, 54.77, 51.04, 46.36, 39.54, 38.81, 37.36, 36.51, 29.15, 23.08. HRMS (ESI-TOF) m/z calcd for C$_{14}$H$_{20}$NaO$_3$ [M + Na $^+$] 259.1310, found 259.1308 | | Light yellow liquid |
| 38 | Zyj07-31-2 | 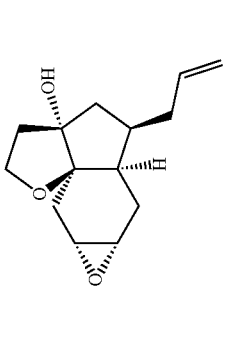 | $^1$H NMR (400 MHZ, CDCl$_3$) δ 5.75-5.63 (m, 1H), 5.00-4.96 (m, 2H), 4.01-3.95 (m, 1H), 3.76-3.70 (m, 1H), 3.29-3.22 (m, 2H), 2.26-2.11 (m, 3H), 2.10-1.93 (m, 8H), 1.84 (dd, J =15.1,3.1 Hz, 1H). $^{13}$C NMR (101 MHz, CDCl$_3$) δ 138.45, 115.54, 89.15, 86.48, 63.77, 53.53, 51.93, 46.08, 42.50, 38.46, 37.04, 36.26, 28.95, 23.22. HRMS (ESI-TOF) m/z calcd for C$_{14}$H$_{20}$NaO$_3$ [M + Na $^+$] 259.1310, found 259.1306. | | Light yellow liquid |
| 39 | Zyj07-103 | 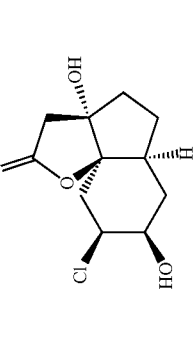 | $^1$H NMR (400 MHz, DMSO) δ 4.24 (s, 1H), 3.95 (s, 1H), 2.83 (d, J = 16.8 Hz, 1H), 2.64-2.48 (m, 1H), 2.38 (dd, J = 15.6, 4.5 Hz, 1H), 2.31-2.17 (m, 1H), 2.04-1.92 (m, 2H), 1.86-1.76 (m, 2H), 1.68-1.60 (m, 1H), 1.29-1.08 (m, 1H). $^{13}$C NMR (101 MHz, DMSO) δ 173.51, 93.57, 81.61, 69.56, 57.93, 42.21, 37.18, 31.79, 27.87, 27.33. | | Light yellow liquid |

TABLE 1-continued

Structure and physicochemical parameters of the 5,5,6, tricyclic spirnolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 40 | Zyj07-14 | 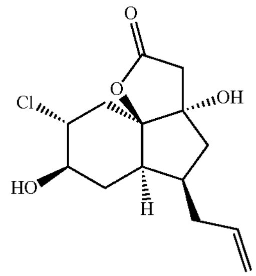 [SMILES: C=CC[C@@H]1C[C@]2(O)CC(=O)O[C@@]23C[C@@H](Cl)[C@H](O)C[C@H]13] | ¹H NMR (400 MHZ, CDCl₃) δ 5.63-5.51 (m, 1H), 4.96-4.87 (m, 2H), 4.23 (s, 1H), 4.15 (s, 1H), 2.72 (dd, J = 36.5, 16.8 Hz, 2H), 2.60-2.47 (m, 2H), 2.29-2.21 (m, 3H), 2.19-2.09 (m, 2H), 1.98 (d, J = 15.0 Hz, 1H), 1.92-1.81 (m, 2H), 1.71 (dd, J = 10.5, 3.1 Hz, 1H). ¹³C NMR (101 MHz, CDCl₃) δ 172.71, 137.30, 116.37, 95.08, 82.75, 70.66, 56.29, 46.70, 42.97, 39.25, 37.89, 35.46, 32.35, 25.75. | | Light yellow liquid |
| 41 | Zyj07-100 | 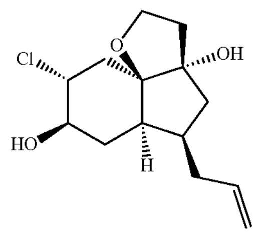 [SMILES: C=CC[C@@H]1C[C@]2(O)CCO[C@@]23C[C@@H](Cl)[C@H](O)C[C@H]13] | 134-136 ¹H NMR (400 MHZ, CDCl₃) δ 5.76-5.65 (m, 1H), 5.03-4.96 (m, 2H), 4.26-4.23 (m, 1H), 4.22-4.17 (m 1H), 4.04-3.98 (m, 1H), 3.80 (q, J = 8.8 Hz, 1H), 2.40-2.23 (m, 3H), 2.21-2.01 (m, 6H), 1.92-1.78 (m, 2H), 1.73-1.66 (m, 1H). ¹³C NMR (101 MHz, CDCl₃) δ 138.66, 115.40, 88.53, 86.73, 71.34, 63.02, 57.78, 45.61, 38.95, 37.49, 37.31, 36.69, 30.97, 25.99. HRMS (ESI-TOF) m/z calcd for C₁₄H₂₁ClNaO₃ [M + Na⁺] 295.1077, found 295.1071. | | White solid |
| 42 | Zyj07-101 | 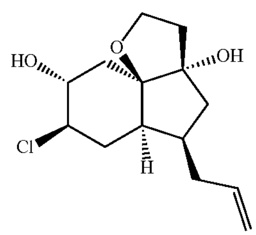 [SMILES: C=CC[C@@H]1C[C@]2(O)CCO[C@@]23C[C@@H](O)[C@H](Cl)C[C@H]13] | 143-144 ¹H NMR (400 MHZ, CDCl₃) δ 5.67-5.55 (m, 1H), 5.03 (d, J = 9.7 Hz, 1H), 4.92 (d, J = 12.6 Hz, 1H), 4.27 (d, J = 1.6 Hz, 1H), 4.07-3.93 (m, 2H), 3.69 (q, J = 8.7 Hz, 1H), 2.46-2.39 (m, 3H), 2.23-1.83 (m, 8H), 1.75-1.63 (m, 2H). ¹³C NMR (101 MHz, CDCl₃) δ 138.28, 115.66, 91.64, 86.06, 72.22, 63.96, 60.15, 45.13, 39.88, 37.88, 37.42, 36.47, 29.11, 27.11. HRMS (ESI-TOF) m/z calcd for C₁₄H₂₁ClNaO₃ [M + Na⁺] 295.1077, found 295.1071. | | White solid |

TABLE 1-continued

Structure and physicochemical parameters of the $5_a5_b6_c$ tricyclic spirnolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 43 | Zyj07-68 | 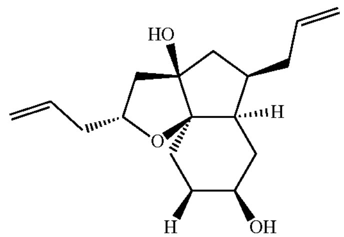 | $^1$H NMR (400 MHz, CDCl$_3$) δ 5.86-5.64 (m, 2H), 5.15-4.96 (m, 4H), 4.19 (s, 1H), 3.93-3.87 (m, 1H), 2.43-2.24 (m, 3H), 2.21-2.00 (m, 5H), 1.96-1.67 (m, 7H), 1.38-1.23 (m, 1H). $^{13}$C NMR (101 MHz, CDCl$_3$) δ 139.04, 134.58, 117.12, 115.17, 89.79, 86.34, 74.33, 66.67, 45.08, 42.86, 41.73, 40.15, 37.93, 36.29, 31.28, 28.31, 26.72. | | White liquid |
| 44 | Zyj07-69 | 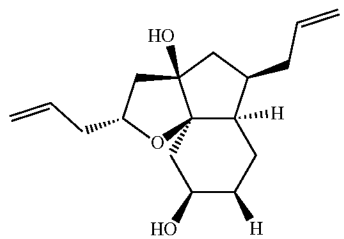 | $^1$H NMR (400 MHz, CDCl$_3$) δ 5.84-5.65 (m, 2H), 5.16-(m, 2H), 5.03-4.96 (m, 2H), 4.59 (d, J = 9.8 Hz, 1H), 4.17-4.10 (m, 1H), 3.96-3.89 (m, 1H), 2.47-2.33 (m, 2H), 2.31-2.15 (m, 3H), 2.12-1.94 (m, 3H), 1.91-1.74 (m, 5H), 1.62-1.57 (m, 2H), 1.48-1.41 (m, 1H). $^{13}$C NMR (101 MHz, CDCl$_3$) δ 138.79, 134.04, 117.67, 115.34, 92.17, 85.98, 75.20, 67.85, 47.10, 44.95, 43.64, 41.60, 38.24, 36.56, 36.19, 33.41. HRMS (ESI-TOF) m/z calcd for C$_{17}$H$_{27}$O$_3$ [M + H $^+$] 279.1960, found 279.1958 | | White liquid |
| 45 | Zyj07-33 | 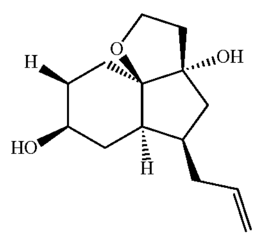 | $^1$H NMR (400 MHz, CDCl$_3$) δ 5.72-5.60 (m, 1H), 4.96-4.91 (m, 4H), 4.16-4.12 (m, 1H), 3.90-3.82 (m, 1H), 3.72-3.66 (m, 1H), 2.39-2.31 (m, 1H), 2.18-1.91 (m, 7H), 1.85-1.66 (m, 6H). $^{13}$C NMR (101 MHz, CDCl$_3$) δ 137.95, 114.11, 88.69, 85.34, 65.55, 62.13, 44.32, 38.80, 36.80, 35.46, 30.29, 27.40, 23.41, 23.32. HRMS (ESI-TOF) m/z calcd for C$_{14}$H$_{23}$O$_3$ [M + H $^+$] 239.1647, found 239.1640. | | White liquid |
| 46 | Zyj07-32 | 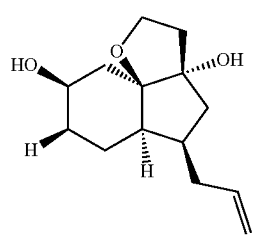 | $^1$H NMR (400 MHz, CDCl$_3$) δ 5.76-5.66 (m, 1H), 5.03-4.95 (m, 2H), 4.17-4.11 (m, 1H), 4.06-3.97 (m, 1H), 3.80-3.70 (m, 1H), 2.33-2.11 (m, 5H), 2.07-1.84 (m, 6H), 1.77-1.73 (m, 1H), 1.60-1.53 (m, 2H). $^{13}$C NMR (101 MHz, CDCl$_3$) δ 138.79, 115.27, 115.22, 91.86, 86.14, 67.94, 63.67, 46.77, 45.03, 38.08, 38.05, 36.46, 34.30, 33.36, 18.86. HRMS (ESI-TOF) m/z calcd for C$_{14}$H$_{23}$O$_3$ [M + H $^+$] 239.1647, found 239.1643. | | Yellow liquid |

TABLE 1-continued

Structure and physicochemical parameters of the 5,5,6c tricyclic spironolactone derivatives XI and its intermediates of the present invention

| No | Code | Structure | ¹H NMR (δ, Solvent: CDCl₃); ¹³C NMR Mp/° C. (100 MHz, CDCl₃); HRMS | Dr value cis/trans | Shape |
|---|---|---|---|---|---|
| 47 | Zyj07-48 | 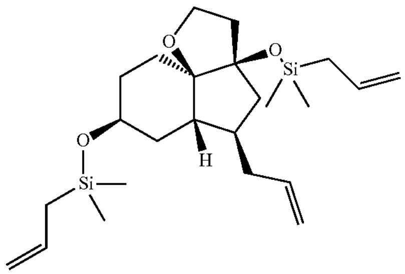 [SMILES: C=CC[C@@H]1C[C@]2(O[Si](C)(C)CC=C)CCO[C@@]23CC[C@H](O[Si](C)(C)CC=C)C[C@@H]13] | ¹H NMR (400 MHZ, CDCl₃) δ 5.86-5.61 (m, 3H), 4.96-4.82 (m, 6H), 4.10 (br, 1H), 3.88-3.84 (m, 1H), 3.71-3.65 (m, 1H), 2.43-2.35 (m, 1H), 2.17-1.90 (m, 6H), 1.78-1.56 (m, 11H). ¹³C NMR (101 MHz, CDCl₃) δ 141.25, 136.43, 136.26, 116.70, 115.34, 115.17, 93.10, 89.60, 69.10, 65.34, 47.55, 41.32, 39.79, 39.51, 38.83, 34.06, 31.19, 28.14, 27.04, 26.39, 1.89, 1.86, 0.00. | | White liquid |
| 48 | Zyj07-46 | 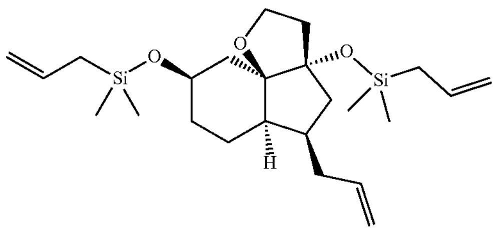 [SMILES: C=CC[C@@H]1C[C@]2(O[Si](C)(C)CC=C)CCO[C@@]23C[C@H](O[Si](C)(C)CC=C)CC[C@H]13] | ¹H NMR (400 MHZ, CDCl₃) δ 5.81-5.57 (m, 3H), 4.94-4.72 (m, 6H), 4.11-4.07 (m, 1H), 3.85-3.80 (m, 1H), 3.67-3.61 (m, 1H), 2.21-2.13 (m, 1H), 2.08-1.69 (m, 10H), 1.58-1.47 (m, 7H), 0.06-0.02 (m, 12H). ¹³C NMR (101 MHz, CDCl₃) δ 138.45, 133.25, 113.64, 112.05, 89.41, 86.88, 66.42, 62.13, 45.48, 44.65, 37.02, 36.32, 36.11, 34.31, 33.32, 25.18, 24.12, 17.89, −1.13, −2.76. | | Yellow liquid |
| 49 | Zyj07-92 | 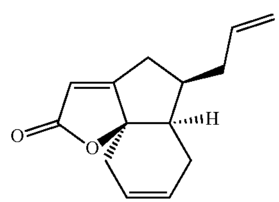 [SMILES: C=CC[C@@H]1CC2=CC(=O)O[C@@]23CC=CC[C@H]13] | ¹H NMR (400 MHZ, CDCl₃) δ 5.98 (d, J = 1.6 Hz, 1H), 5.92-5.85 (m, 1H), 5.73-5.68 (m, 1H), 5.67-5.56 (m, 1H), 5.02-4.93 (m, 2H), 3.28 (s, 1H), 2.74-2.64 (m, 3H), 2.53-2.45 (m, 1H), 2.43-2.36 (m, 1H), 2.23-2.12 (m, 2H), 2.05-1.96 (m, 1H), 1.74-1.68 (m, 1H), 1.65-1.57 (m, 1H). ¹³C NMR (101 MHz, CDCl₃) δ 179.23, 172.16, 136.04, 129.40, 124.92, 120.45, 116.71, 92.88, 45.75, 43.87, 41.08, 36.10, 30.86, 24.98. HRMS (ESI-TOF) m/z calcd for C₁₄H₁₇O₂ [M + H ⁺] 217.1229, found 217.1227. | | Yellow liquid |

TABLE 1-continued

Structure and physicochemical parameters of the 5,5,6 C tricyclic spironolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 50 | Zyj07-30-1 | 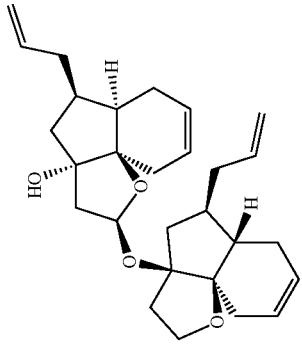 | $^1$H NMR (400 MHz, CDCl$_3$) δ 5.75-5.62 (m, 6H), 5.25-5.10 (m, 1H), 4.99-4.91 (m, 4H), 3.91-3.85 (m, 1H), 3.75-3.68 (m, 1H), 2.59-2.52 (m, 1H), 2.44-1.76 (m, 23H). $^{13}$C NMR (101 MHz, CDCl$_3$) δ 138.96, 138.73, 127.22, 127.02, 125.00, 124.16, 115.19, 98.03, 90.60, 90.22, 89.89, 85.46, 64.76, 48.15, 46.95, 43.65, 42.97, 40.78, 37.97, 37.89, 36.77, 36.70, 36.50, 31.92, 31.33, 24.97. HRMS (ESI-TOF) m/z calcd for C$_{28}$H$_{38}$NaO$_4$ [M + Na $^+$] 461.2668, found 461.2668. | | White liquid |
| 51 | Zyj07-30-2 | 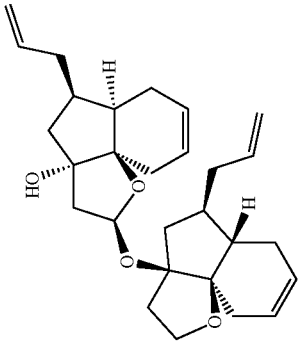 | $^1$H NMR (400 MHz, CDCl$_3$) δ 5.81-5.61 (m, 6H), 5.25-5.18 (m, 1H), 5.00-4.94 (m, 4H), 4.00-3.92 (m, 1H), 3.88-3.79 (m, 1H), 2.81-2.75 (m, 1H), 2.62-2.55 (m, 1H), 2.37-2.16 (m, 11H), 2.15-1.94 (m, 9H), 1.91-1.81 (m, 2H). $^{13}$C NMR (101 MHz, CDCl$_3$) δ 139.00, 138.75, 127.21, 124.92, 124.14, 115.22, 114.77, 99.93, 90.59, 90.54, 90.21, 85.47, 64.12, 48.89, 46.80, 43.95, 42.83, 41.74, 38.10, 37.38, 36.45, 34.97, 32.44, 30.95, 25.06, 24.99. HRMS (ESI-TOF) m/z calcd for C$_{28}$H$_{38}$NaO$_4$ [M + Na $^+$] 461.2668, found 461.2668. | | White liquid |
| 52 | Zyj07-49 | 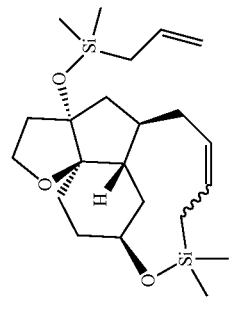 | $^1$H NMR (400 MHz, CDCl$_3$) δ 5.82-5.64 (m, 1H), 5.40-5.26 (m, 2H), 4.96-4.87 (m, 2H), 4.22 (br, 1H), 3.91-3.86 (m, 1H), 3.75-3.64 (m, 1H), 2.66-2.54 (m, 1H), 2.17-2.03 (m, 4H), 2.00-1.91 (m, 3H), 1.67-1.52 (m, 10H). $^{13}$C NMR (101 MHz, CDCl$_3$) δ 138.39, 124.05, 123.52, 113.68, 89.33, 86.38, 66.71, 62.51, 43.56, 37.61, 36.46, 36.25, 35.68, 30.87, 28.26, 23.62, 23.39, 22.82, −0.25, −0.32, −1.39, −1.91. | | Yellow liquid |

TABLE 1-continued

Structure and physicochemical parameters of the 5,5,6c tricyclic spironolactone derivatives XI and its intermediates of the present invention

| No | Code | Structure | $^1$H NMR (δ, Solvent: CDCl$_3$); $^{13}$C NMR Mp/° C. (100 MHz, CDCl$_3$); HRMS | Dr value cis/trans | Shape |
|---|---|---|---|---|---|
| 53 | Zyj07-41-2 | (structure) | $^1$H NMR (400 MHZ, CDCl$_3$) δ 5.75-5.54 (m, 3H), 5.38-5.28 (m, 1H), 4.45-4.34 (m, 1H), 2.77 (dd, J = 14.1, 8.9 Hz, 1H), 2.55-2.51 (m, 2H), 2.40-2.30 (m, 1H), 2.20-1.92 (m, 12H), 1.88-1.77 (m, 1H). $^{13}$C NMR (101 MHz, CDCl$_3$) δ 169.23, 127.35, 125.85, 125.38, 123.24, 94.75, 92.62, 74.53, 46.53, 43.91, 42.31, 37.43, 36.00, 33.63, 27.82, 21.80, 20.73. HRMS (ESI-TOF) m/z calcd for C$_{17}$H$_{23}$O$_3$ [M + H $^+$] 275.1647, found 275.1635. | | Yellow liquid |

TABLE 2

Insecticidal, fungicidal and antiviral activity determination results of the $5_A5_B6_C$ tricyclic spironolactone derivatives XI and its intermediates of the present invention

| No | Code | Mythimna separate (Walker) | Helicoverpa armigera (Hübner) | Ostrinia furnacalis | Caenorhabditis elegans | AS | BC | CA | GZ | PI | PP | PS | RC | SS | TMV inactivation |
|---|---|---|---|---|---|---|---|---|---|---|---|---|---|---|---|
| 1 | Zyj06-39 | 10 | 0 | 0 | 47 | 73 | 36 | 89 | 80 | 27 | 88 | 100 | 93 | 81 | 50 |
| 2 | Zyj06-43 | 30 | 10 | 5 | 10 | 73 | 34 | 78 | 73 | 15 | 98 | 57 | 96 | 69 | 10 |
| 3 | Zyj06-72 | 40 | 20 | 15 | 5 | 0 | 73 | 51 | 30 | 12 | 12 | 36 | 0 | 57 | 48 |
| 4 | Zyj06-80 | 0 | 0 | 0 | 8 | 0 | 20 | 14 | 20 | 25 | 18 | 16 | 16 | 33 | 41 |
| 5 | Zyj06-82 | 25 | 5 | 5 | 8 | 14 | 57 | 24 | 0 | 16 | 40 | 23 | 43 | 71 | 40 |
| 6 | Zyj06-162 | ND | ND | ND | ND | ND | ND | ND | ND | ND | ND | ND | ND | ND | ND |
| 7 | Zyj06-161 | 55 | 25 | 20 | ND | 0 | 7 | 24 | 0 | 12 | 38 | 14 | 0 | 76 | ND |
| 8 | Zyj06-177 | 0 | 0 | 0 | 60 | 12 | 48 | 46 | 0 | 11 | 11 | 19 | 61 | 78 | 38 |
| 9 | Zyj06-92-2 | 20 | 10 | 10 | 20 | 78 | 30 | 95 | 73 | 15 | 98 | 41 | 79 | 38 | 37 |
| 10 | Zyj06-111-2 | 100 | 50 | 40 | 40 | 14 | 39 | 51 | 47 | 31 | 73 | 0 | 0 | 10 | 24 |
| 11 | Zyj06-113-2 | 20 | 5 | 15 | 7 | 3 | 64 | 24 | 0 | 40 | 26 | 25 | 0 | 36 | 28 |
| 12 | Zyj06-166 | 0 | 0 | 0 | 5 | 35 | 36 | 62 | 27 | 25 | 38 | 18 | 0 | 17 | 54 |
| 13 | Zyj07-95 | 40 | 10 | 10 | ND | 68 | 77 | 84 | 53 | 29 | 98 | 57 | 82 | 64 | 82 |
| 14 | Zyj06-180 | 20 | 5 | 0 | 22 | 14 | 50 | 30 | 20 | 19 | 15 | 45 | 0 | 52 | 5 |
| 15 | Zyj06-127 | 0 | 0 | 0 | 7 | 7 | 45 | 23 | 36 | 2 | 5 | 4 | 40 | 76 | 63 |
| 16 | Zyj06-187 | 10 | 0 | 0 | 8 | 14 | 34 | 68 | 60 | 31 | 81 | 0 | 50 | 43 | 58 |
| 17 | Zyj06-113-3 | 0 | 0 | 0 | 5 | 35 | 55 | 51 | 43 | 11 | 99 | 11 | 32 | 76 | 58 |
| 18 | Zyj06-167 | ND | ND | ND | 25 | 34 | 13 | 26 | 46 | 0 | 0 | 24 | 59 | 9 | 86 |
| 19 | Zyj07-96 | 40 | 15 | 10 | 60 | 70 | 25 | 92 | 67 | 24 | 100 | 68 | 96 | 69 | 23 |
| 20 | Zyj06-186 | 0 | 0 | 0 | 15 | 7 | 49 | 46 | 21 | 4 | 11 | 6 | 41 | 66 | 63 |
| 22 | Zyj06-189 | 0 | 0 | 0 | 8 | 0 | 55 | 24 | 13 | 23 | 69 | 23 | 29 | 0 | 40 |
| 22 | Zyj06-128 | ND | ND | ND | 30 | 39 | 25 | 27 | 84 | 7 | 8 | 20 | 71 | 0 | ND |
| 23 | Zyj06-175 | ND | ND | ND | 15 | 39 | 25 | 33 | 14 | 0 | 8 | 5 | 61 | 11 | 39 |
| 24 | Zyj07-29 | 35 | 15 | 10 | 50 | 0 | 27 | 5 | 7 | 25 | 45 | 0 | 0 | 76 | 51 |
| 25 | Zyj07-37-1 | 20 | 15 | 10 | 20 | 14 | 82 | 14 | 0 | 15 | 59 | 0 | 7 | 64 | 16 |
| 26 | Zyj07-37-2 | 20 | 15 | 0 | 13 | 22 | 18 | 27 | 3 | 21 | 31 | 18 | 21 | 62 | 28 |
| 27 | Zyj07-38 | 15 | 10 | 5 | 37 | ND | ND | ND | ND | ND | ND | ND | ND | ND | 30 |
| 28 | Zyj07-98 | 0 | 0 | 0 | 25 | 73 | 55 | 78 | 53 | 17 | 96 | 27 | 82 | 55 | 71 |
| 29 | Zyj07-30 | 0 | 0 | 0 | 7 | 0 | 39 | 14 | 3 | 15 | 0 | 27 | 13 | 79 | 76 |
| 30 | Zyj07-102 | 0 | 0 | 0 | 62 | 0 | 41 | 14 | 27 | 23 | 42 | 0 | 0 | 0 | 14 |
| 31 | Zyj07-13 | ND | ND | ND | 20 | 10 | 55 | 8 | 14 | 0.00 | 30 | 6 | 43 | 83 | 11 |
| 32 | Zyj07-64 | 20 | 10 | 5 | 8 | 73 | 41 | 89 | 73 | 17 | 87 | 72 | 75 | 45 | 72 |
| 33 | Zyj07-65-1 | 25 | 10 | 5 | 12 | ND | ND | ND | ND | ND | ND | ND | ND | ND | 85 |
| 34 | Zyj07-65-2 | 30 | 10 | 5 | 17 | 0 | 41 | 24 | 0 | 25 | 12 | 0 | 7 | 24 | 29 |
| 35 | Zyj07-67-1 | 20 | 10 | 5 | 56 | 0 | 59 | 14 | 23 | 32 | 31 | 18 | 0 | 86 | 7 |
| 36 | Zyj07-67-2 | 0 | 0 | 0 | 20 | 0 | 64 | 24 | 0 | 25 | 13 | 36 | 29 | 69 | 29 |
| 37 | Zyj07-31-1 | 0 | 0 | 0 | 18 | 14 | 36 | 41 | 7 | 15 | 58 | 0 | 7 | 0 | 11 |
| 38 | Zyj07-31-2 | 40 | 0 | 0 | 8 | 22 | 18 | 27 | 3 | 21 | 31 | 18 | 21 | 62 | 15 |
| 39 | Zyj07-103 | 30 | 15 | 10 |  | 30 | 27 | 38 | 47 | 42 | 58 | 0 | 4 | 95 | 98 |
| 40 | Zyj07-14 | ND | ND | ND | 20 | 15 | 64 | 31 | 43 | 2 | 31 | 15 | 51 | 93 | ND |
| 41 | Zyj07-100 | 10 | 0 | 0 | ND | 14 | 14 | 46 | 13 | 38 | 29 | 23 | 0 | 76 | 92 |
| 42 | Zyj07-101 | 40 | 20 | 15 | ND | 5 | 64 | 14 | 3 | 65 | 69 | 0 | 29 | 74 | 82 |
| 43 | Zyj07-68 | 0 | 0 | 0 | 13 | 3 | 36 | 19 | 0 | 13 | 2 | 9 | 21 | 62 | 93 |
| 44 | Zyj07-69 | 25 | 15 | 10 | 10 | ND | ND | ND | ND | ND | ND | ND | ND | ND | 83 |
| 45 | Zyj07-33 | 40 | 15 | 10 | 27 | 24 | 52 | 46 | 27 | 16 | 60 | 27 | 41 | 31 | 9 |
| 46 | Zyj07-32 | 0 | 0 | 0 | 20 | 46 | 23 | 68 | 33 | 75 | 84 | 16 | 39 | 81 | 9 |
| 47 | Zyj07-48 | 0 | 0 | 0 | 25 | 0 | 59 | 35 | 7 | 19 | 13 | 14 | 0 | 67 | 59 |
| 48 | Zyj07-46 | 20 | 5 | 0 | 10 | 8 | 55 | 14 | 3 | 21 | 21 | 22 | 0 | 67 | 45 |
| 49 | Zyj07-92 | 20 | 0 | 0 | ND | 78 | 30 | 95 | 73 | 15 | 98 | 40 | 79 | 38 | 91 |
| 50 | Zyj07-30-1 | 0 | 0 | 0 | 5 | 14 | 5 | 41 | 0 | 21 | 83 | 22 | 0 | 95 | 8 |
| 51 | Zyj07-30-2 | 0 | 0 | 0 | 33 | 0 | 34 | 73 | 27 | 14 | 48 | 0 | 0 | 95 | 16 |
| 52 | Zyj07-49 | 20 | 0 | 0 | 15 | 89 | 34 | 89 | 87 | 16 | 96 | 45 | 96 | 60 | 28 |
| 53 | Zyj07-41-2 | 10 | 15 | 0 | 12 | 14 | 34 | 51 | 20 | 25 | 60 | 41 | 100 | 71 | 18 |
| 54 | Ryanodine | 100 | 100 | 100 | 5 | 25 | 25 | 10 | 20 | 30 | 25 | 32 | 50 | 25 | 6 |

TABLE 3

Toxicological activity determination results of the $5_A5_B6_C$ tricyclic spironolactone derivatives XI and its intermediates of the present invention against Italian honey bee

| Code | Dosage (μg a.i./bee) | Number of bee | Death number after 24 h | Death number after 48 h | Death rate after 48 h (%) |
|---|---|---|---|---|---|
| CK | 0 | 10 | 0 | 0 | 0 |
|  |  | 10 | 0 | 0 |  |
| Zyj07-41-2 | 13.5 | 10 | 0 | 0 | 0 |
|  |  | 10 | 0 | 0 |  |
| Zyj07-41-2 | 8.70 | 10 | 0 | 0 | 0 |
|  |  | 10 | 0 | 0 |  |
| Zyj07-49 | 19.8 | 10 | 0 | 0 | 0 |
|  |  | 10 | 0 | 0 |  |

TABLE 3-continued

Toxicological activity determination results of the $5_A5_B6_C$ tricyclic spironolactone derivatives XI and its intermediates of the present invention against Italian honey bee

| Code | Dosage (μg a.i./bee) | Number of bee | Death number after 24 h | Death number after 48 h | Death rate after 48 h (%) |
|---|---|---|---|---|---|
| Zyj07-49 | 6.06 | 10 | 0 | 0 | 0 |
|  |  | 10 | 0 | 0 |  |
| Zyj06-80 | 19.3 | 10 | 0 | 0 | 0 |
|  |  | 10 | 0 | 0 |  |
| Zyj06-80 | 7.63 | 10 | 0 | 0 | 0 |
|  |  | 10 | 0 | 0 |  |
| Zyj07-96 | 15.5 | 10 | 0 | 0 | 0 |
|  |  | 10 | 0 | 0 |  |
| Zyj07-96 | 9.54 | 10 | 0 | 0 | 0 |
|  |  | 10 | 0 | 0 |  |
| Zyj-7-98 | 12.0 | 10 | 0 | 0 | 0 |
|  |  | 10 | 0 | 0 |  |
| Zyj07-98 | 8.47 | 10 | 0 | 0 | 0 |
|  |  | 10 | 0 | 0 |  |
| Zyj07-31-2 | 9.36 | 10 | 0 | 1 | 10.0 |
|  |  | 10 | 0 | 1 |  |
| Zyj07-31-2 | 6.51 | 10 | 0 | 0 | 0 |
|  |  | 10 | 0 | 0 |  |
| Zyj07-48 | 19.8 | 10 | 0 | 0 | 0 |
|  |  | 10 | 0 | 0 |  |
| Zyj07-48 | 9.89 | 10 | 0 | 0 | 5.0 |
|  |  | 10 | 0 | 1 |  |
| Zyj07-37-1 | 15.3 | 10 | 0 | 0 | 0 |
|  |  | 10 | 0 | 0 |  |
| Zyj07-37-1 | 7.55 | 10 | 0 | 0 | 0 |
|  |  | 10 | 0 | 0 |  |
| Zyj07-95 | 19.9 | 10 | 0 | 0 | 0 |
|  |  | 10 | 0 | 0 |  |
| Zyj07-95 | 9.36 | 10 | 0 | 0 | 0 |
|  |  | 10 | 0 | 0 |  |
| Zyj06-177 | 9.46 | 10 | 0 | 0 | 0 |
|  |  | 10 | 0 | 0 |  |
| Zyj06-177 | 8.17 | 10 | 0 | 0 | 0 |
|  |  | 10 | 0 | 0 |  |
| Zyj06-166 | 19.7 | 10 | 0 | 1 | 10.0 |
|  |  | 10 | 0 | 1 |  |
| Zyj06-166 | 9.93 | 10 | 0 | 0 | 0 |
|  |  | 10 | 0 | 0 |  |
| Zyj07-64 | 15.5 | 10 | 0 | 0 | 10.0 |
|  |  | 10 | 1 | 2 |  |
| Zyj07-64 | 10.0 | 10 | 0 | 1 | 15.0 |
|  |  | 10 | 0 | 2 |  |
| Zyj06-113-2 | 12.6 | 10 | 0 | 1 | 15.0 |
|  |  | 10 | 0 | 2 |  |
| Zyj06-113-2 | 9.69 | 10 | 0 | 0 | 10.0 |
|  |  | 10 | 0 | 2 |  |
| Zyj07-30 | 19.8 | 10 | 0 | 1 | 5.0 |
|  |  | 10 | 0 | 0 |  |
| Zyj07-30 | 9.77 | 10 | 0 | 1 | 15.0 |
|  |  | 10 | 0 | 2 |  |
| Zyj07-32 | 10.0 | 10 | 0 | 1 | 5.0 |
|  |  | 10 | 0 | 0 |  |
| Zyj07-32 | 2.73 | 10 | 0 | 0 | 10.0 |
|  |  | 10 | 2 | 2 |  |
| Zyj06-180 | 10.6 | 10 | 1 | 1 | 5.0 |
|  |  | 10 | 0 | 0 |  |
| Dimethoate | 0.109 | 10 | 2 | — | 16.7 |
|  |  | 10 | 1 | — |  |
|  |  | 10 | 2 | — |  |
| Dimethoate | 0.166 | 10 | 5 | — | 40.0 |
|  |  | 10 | 4 | — |  |
|  |  | 10 | 3 | — |  |
| Dimethoate | 0.294 | 10 | 6 | — | 53.3 |
|  |  | 10 | 6 | — |  |
|  |  | 10 | 4 | — |  |
| Dimethoate | 0.476 | 10 | 5 | — | 70.0 |
|  |  | 10 | 7 | — |  |
|  |  | 10 | 9 | — |  |
| Dimethoate | 0.830 | 10 | 9 | — | 76.7 |
|  |  | 10 | 8 | — |  |
|  |  | 10 | 6 | — |  |
| Zyj07-92 | 14.3 | 10 | 0 | 0 | 5.0 |
|  |  | 10 | 0 | 1 |  |
| Zyj07-92 | 7.44 | 10 | 0 | 0 | 5.0 |
|  |  | 10 | 0 | 1 |  |
| Zyj07-65-1 | 18.1 | 10 | 0 | 0 | 10.0 |
|  |  | 10 | 1 | 2 |  |
| Zyj07-65-1 | 7.54 | 10 | 0 | 0 | 10.0 |
|  |  | 10 | 1 | 2 |  |
| Zyj07-69 | 9.71 | 10 | 0 | 0 | 5.0 |
|  |  | 10 | 0 | 1 |  |
| Zyj0-7-69 | 4.27 | 10 | 0 | 0 | 0 |
|  |  | 10 | 0 | 0 |  |
| Zyj07-29 | 3.68 | 10 | 0 | 0 | 5.0 |
|  |  | 10 | 0 | 1 |  |
| Zyj07-29 | 4.39 | 10 | 0 | 0 | 0 |
|  |  | 10 | 0 | 0 |  |
| Zyj07-68 | 16.1 | 10 | 0 | 0 | 0 |
|  |  | 10 | 0 | 0 |  |
| Zyj07-68 | 9.97 | 10 | 0 | 1 | 10.0 |
|  |  | 10 | 0 | 1 |  |
| Zyj07-65-2 | 10.9 | 10 | 0 | 0 | 0 |
|  |  | 10 | 0 | 0 |  |
| Zyj07-65-2 | 9.57 | 10 | 0 | 0 | 5.0 |
|  |  | 10 | 0 | 1 |  |
| Zyj06-113-3 | 15.2 | 10 | 0 | 1 | 10.0 |
|  |  | 10 | 0 | 1 |  |
| Zyj06-113-3 | 9.87 | 10 | 0 | 0 | 0 |
|  |  | 10 | 0 | 0 |  |
| Zyj06-72 | 9.05 | 10 | 0 | 0 | 0 |
|  |  | 10 | 0 | 0 |  |
| Zyj06-72 | 7.87 | 10 | 0 | 0 | 5.0 |
|  |  | 10 | 0 | 1 |  |
| Zyj06-189 | 16.4 | 10 | 0 | 0 | 0 |
|  |  | 10 | 0 | 0 |  |
| Zyj06-189 | 9.77 | 10 | 0 | 0 | 0 |
|  |  | 10 | 0 | 0 |  |
| Zyj06-187 | 10.6 | 10 | 0 | 1 | 10.0 |
|  |  | 10 | 0 | 1 |  |
| Zyj06-187 | 6.08 | 10 | 0 | 0 | 0 |
|  |  | 10 | 0 | 0 |  |
| Zyj07-30-1 | 10.6 | 10 | 0 | 0 | 5.0 |
|  |  | 10 | 0 | 1 |  |
| Zyj07-30-1 | 5.12 | 10 | 0 | 0 | 0 |
|  |  | 10 | 0 | 0 |  |
| Zyj06-127 | 7.70 | 10 | 0 | 0 | 0 |
|  |  | 10 | 0 | 0 |  |
| Zyj06-127 | 5.40 | 10 | 0 | 0 | 0 |
|  |  | 10 | 0 | 0 |  |
| Ryanodine | 3.65 | 10 | 1 | 10 | 100 |
|  |  | 10 | 5 | 10 |  |
| Ryanodine | 1.54 | 10 | 4 | 10 | 100 |
|  |  | 10 | 5 | 10 |  |
| Ryanodine | 1.19 | 10 | 2 | 8 | 90.0 |
|  |  | 10 | 1 | 10 |  |
| Ryanodine | 0.395 | 10 | 4 | 10 | 100 |
|  |  | 10 | 8 | 10 |  |
| Ryanodine | 0.275 | 10 | 2 | 7 | 85.0 |
|  |  | 10 | 1 | 10 |  |
| Ryanodine | 0.102 | 10 | 1 | 6 | 65.0 |
|  |  | 10 | 0 | 7 |  |
| Ryanodine | $8.80 \times 10^{-3}$ | 10 | 6 | 4 | 30.0 |
|  |  | 10 | 4 | 2 |  |
| Ryanodine | $7.08 \times 10^{-3}$ | 10 | 0 | 0 | 0 |
|  |  | 10 | 0 | 0 |  |

INDUSTRIAL PRACTICALITY

The present invention relates to a $5_A5_B6_C$ tricyclic spironolactone derivative. The $5_A5_B6_C$ tricyclic spironolactone derivative provided by the present invention, accordingly, is a compound with a formula XI of:

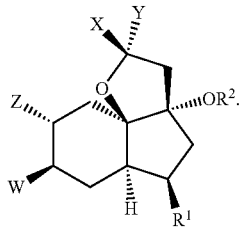

XI

The present invention also relates to its preparation method and its applications in the areas of insecticide, nematicide, fungicide and anti-viral agent. The $5_A5_B6_C$ tricyclic spironolactone derivatives in present invention are high-performance, broad-spectrum, low-toxicity and low-ecological risk compounds with excellent economic values and a wide range of applications in the areas of agriculture, horticulture, forestry and health.

What is claimed is:

1. A $5_A5_B6_C$ tricyclic spironolactone derivative with a formula shown as XI:

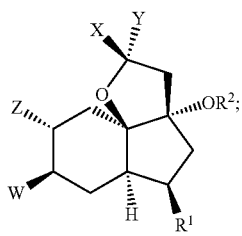

XI wherein: $R^1$ is hydrogen, allyl, propargyl, Ac, AcO, t-BuOO—, methoxy, $CH(CO_2Et)_2$, —$CH_2CO_2Et$ or isopropenyl;
$R^2$ is hydrogen, allyl, propargyl, Ac, AcO, t-BuOO—, methoxy, —$CH_2CO_2Et$ or isopropenyl;
X is hydrogen, hydroxyl, OAc, allyl, or propargyl;
Y is hydrogen, hydroxyl, OAc, allyl, or propargyl;

is C=O or C=S; Z is hydrogen, hydroxyl, or chlorine;
W is hydrogen, hydroxyl, or chlorine;
$R^1$ and W constitute

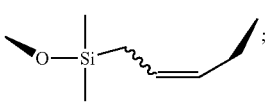

and $R^2$ and W constitute

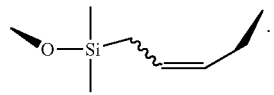

2. A pesticide composition, comprising a 5A5B6C tricyclic spironolactone derivative XI as an active ingredient, solid or liquid adjuvants, and surfactants, wherein the $5_A5_B6_C$ tricyclic spironolactone derivative XI has a formula shown as:

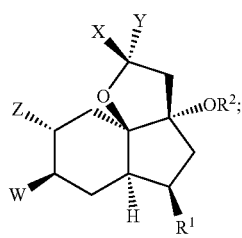

XI wherein: $R^1$ is hydrogen, allyl, propargyl, Ac, AcO, t-BuOO—, methoxy, $CH(CO_2Et)_2$, —$CH_2CO_2Et$ or isopropenyl,
$R^2$ is hydrogen, allyl, propargyl, Ac, AcO, t-BuOO—, methoxy, —$CH_2CO_2Et$ or isopropenyl;
X is hydrogen, hydroxyl, OAc, allyl, or propargyl;
Y is hydrogen, hydroxyl, OAc, allyl, or propargyl;

is C=O or C=S; Z is hydrogen, hydroxyl, or chlorine;
W is hydrogen, hydroxyl, or chlorine;
$R^1$ and W constitute

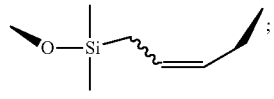

and
$R^2$ and W constitute

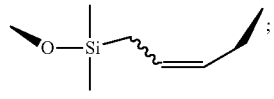

wherein:
a mass percentage of the active ingredient is 0.1%-99%,
a mass percentage of the solid or liquid adjuvants is 99.9%-1%, and
a mass percentage of the surfactants is 0-25%;
the $5_A5_B6_C$ tricyclic spironolactone derivative XI is able to kill insects, kill nematodes, kill funguses and resist viruses; and
the viruses comprise a tobacco mosaic virus.

* * * * *